US010174069B2

(12) United States Patent
Field et al.

(10) Patent No.: US 10,174,069 B2
(45) Date of Patent: Jan. 8, 2019

(54) VIRUS DETECTION

(71) Applicant: ICENI DIAGNOSTICS LIMITED, Norwich (GB)

(72) Inventors: Rob Field, Norfolk (GB); Martin Rejzek, Norfolk (GB); Abdul Rashid, Norfolk (GB); David Andrew Russell, Norfolk (GB); Maria Jose Marin Altaba, Norfolk (GB)

(73) Assignee: ICENI DIAGNOSTICS LIMITED, Norwich (GB)

( * ) Notice: Subject to any disclaimer, the term of this patent is extended or adjusted under 35 U.S.C. 154(b) by 25 days.

(21) Appl. No.: 14/906,436

(22) PCT Filed: Jul. 3, 2014

(86) PCT No.: PCT/GB2014/052026
§ 371 (c)(1),
(2) Date: Jan. 20, 2016

(87) PCT Pub. No.: WO2015/011441
PCT Pub. Date: Jan. 29, 2015

(65) Prior Publication Data
US 2016/0185814 A1      Jun. 30, 2016

(30) Foreign Application Priority Data

Jul. 24, 2013   (GB) .................................. 1313201.4

(51) Int. Cl.
*C07H 23/00* (2006.01)
*C07H 15/04* (2006.01)
*G01N 33/569* (2006.01)
*G01N 33/58* (2006.01)

(52) U.S. Cl.
CPC ............. *C07H 23/00* (2013.01); *C07H 15/04* (2013.01); *G01N 33/56983* (2013.01); *G01N 33/587* (2013.01); *G01N 2333/11* (2013.01); *G01N 2400/10* (2013.01)

(58) Field of Classification Search
None
See application file for complete search history.

(56) References Cited

U.S. PATENT DOCUMENTS

2008/0194801 A1    8/2008  Swanson et al.

OTHER PUBLICATIONS

Rahman et al. Glycobiology, vol. 23, pp. 495-504, 2013.*
Suenaga et al., Biosensors and Bioelectronics vol. 32, Issue 1, Feb. 15, 2012, pp. 195-201.*
Feng et al., Antiviral Chem and Chemo vol. 23, pp. 59-65, year 2013.*
Earle et al., "Chemoenzymatic synthesis of a trimeric ganglioside GM3 analogue", Carbohydrate Research 301:1-4 (1997).
Gamblin et al., "Influenza hemagglutinin and neuraminidase membrane glycoproteins", Journal of Biological Chemistry, 285(37):28403-28409 (2010).
Lin et al., "Evolution of the receptor binding properties of the influenza A(H3N2) hemagglutinin", PNAS, 109(52):21474-21479 (2012).
Marin et al., "Glyconanoparticles for the plasmonic detection and discrimination between human and avian influenza virus", Org. Biomol. Chem., 11(41):7101 (2013).
Papin et al., "Fast access to Robust C-Sialoside multimers", Chem. Eur. J., 15(1):53-57 (2009).
Rahman et al., "Inhibitory effects and specificity of synthetic sialyldendrimers toward recombinant human cytosolic sialidase 2 (NEU2)", Glycobiology, 23(4):495-504 (2013).
Sliedregt et al., "Design and synthesis of a multivalent homing device for targeting to murine CD22", Bioorganic & Medicinal Chemistry 9(1):85-97 (2001).
Veeneman et al., "Synthesis of sialic acid-lipid conjugates and their neuritogenic effects on N1E.115 neuroblastoma cells", Bioorganic & Medicinal Chemistry Letters, 5(1):9-14 (1995).
Yu et al., "Recognition between a divalent sialyl molecule and wheat germ agglutinin", Tetrahedron Letters, 50(45):6130-6132 (2009).

* cited by examiner

*Primary Examiner* — Shanon A. Foley
*Assistant Examiner* — Myron G Hill
(74) *Attorney, Agent, or Firm* — Nixon Peabody LLP; Mark J. FitzGerald; Teresa A. Ptashka

(57) ABSTRACT

The invention provides methods and materials for use in the detection of influenza viruses which utilise a nanoparticle, for example gold nanoparticle, probe comprising a plurality of glycoconjugate ligands, each glyconjugate ligand (GL) having a plurality of sialic-acid containing recognition group (Y) coupled to the nanoparticle via a multivalent core (X), wherein the multivalent core (X) is a trivalent core, whereby there are 3 recognition groups per ligand, wherein the recognition groups on the bioconjugate specifically bind to the hemagglutinin on the target influenza virus. The probes may include further ligands bound to the nanoparticle which do not bind specifically to an influenza virus—for example polyethylene glycol groups. These can modulate density of the glycoconjugate ligand on the surface of the nanoparticle. Binding of probes is detected by a plasmonic signal which is specific to the influenza virus.

34 Claims, 12 Drawing Sheets

Figure 1:
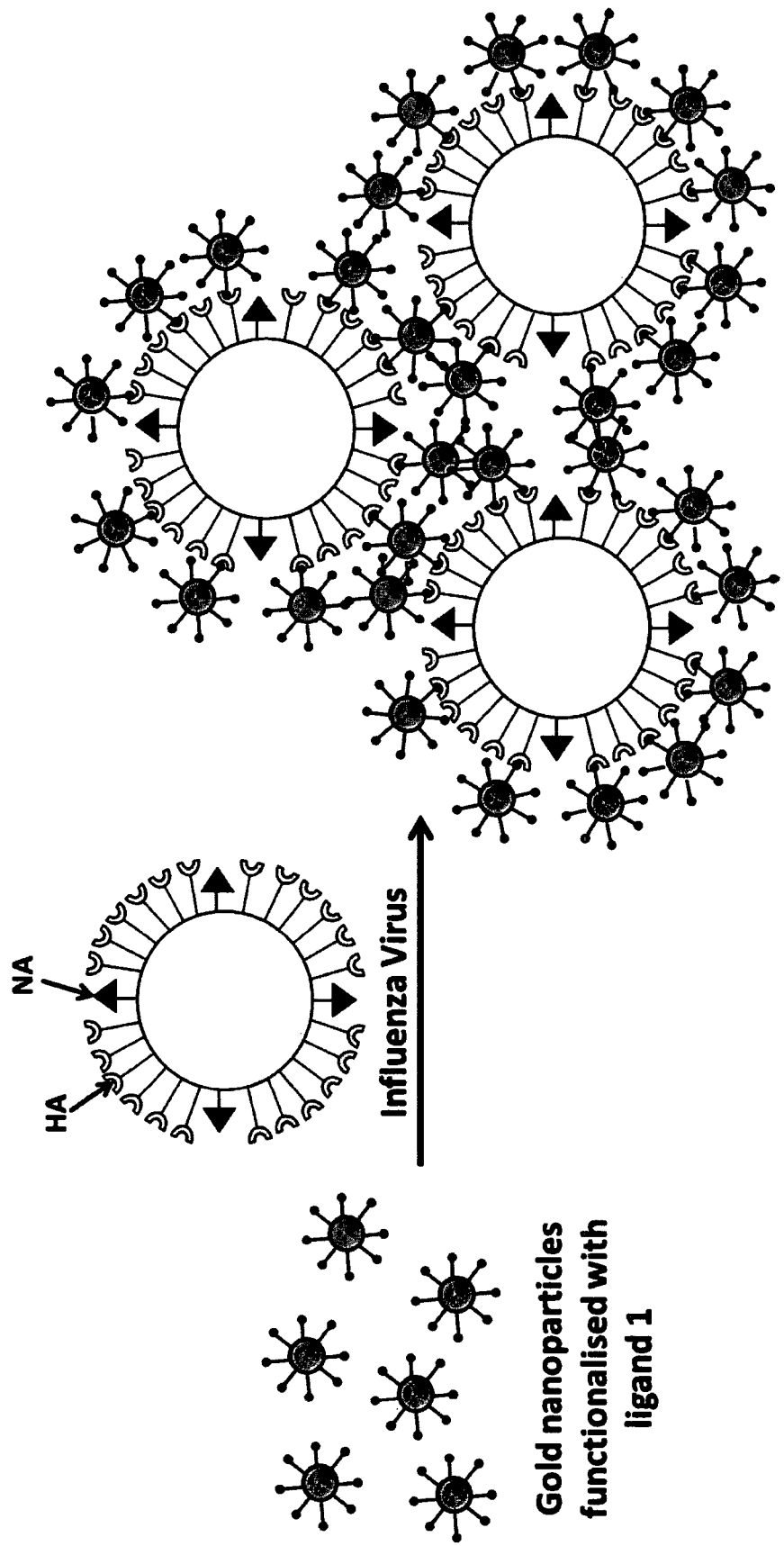

Figure 6
a) 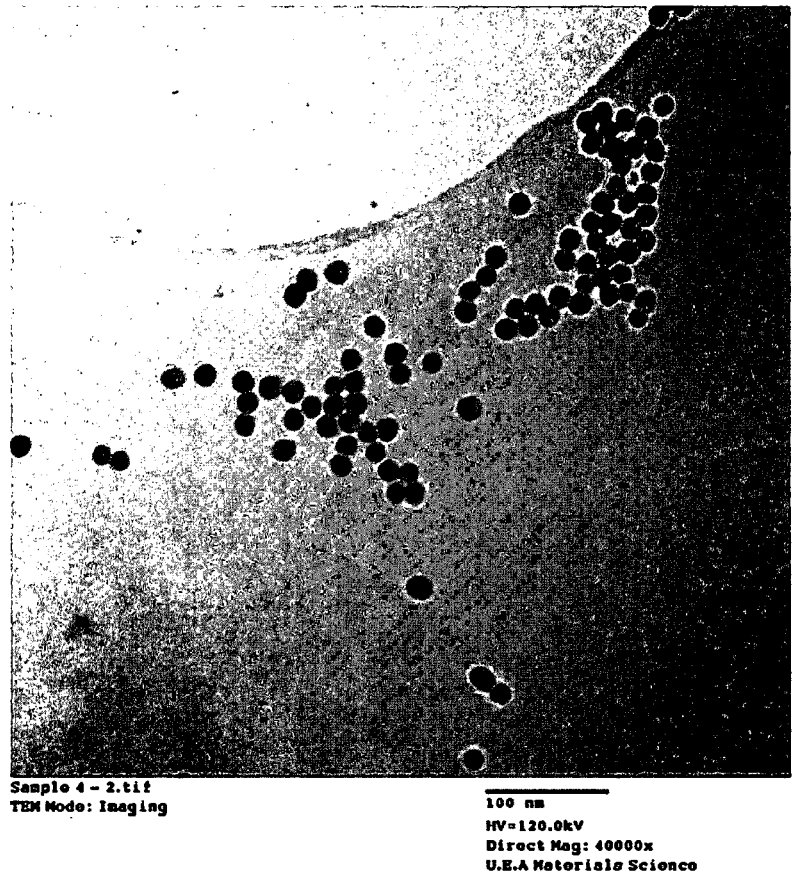
b) 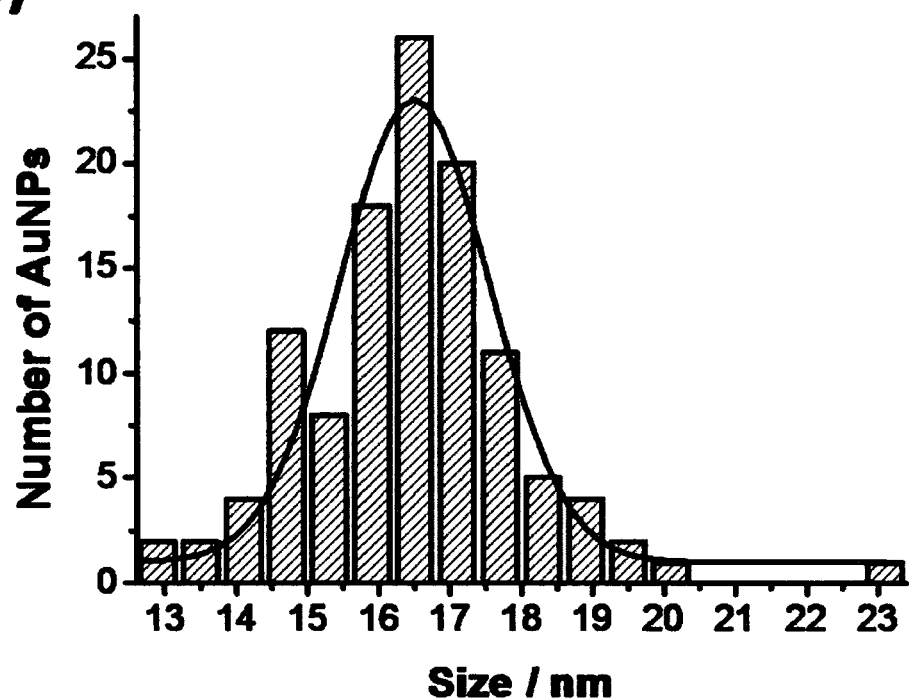

Figure 9
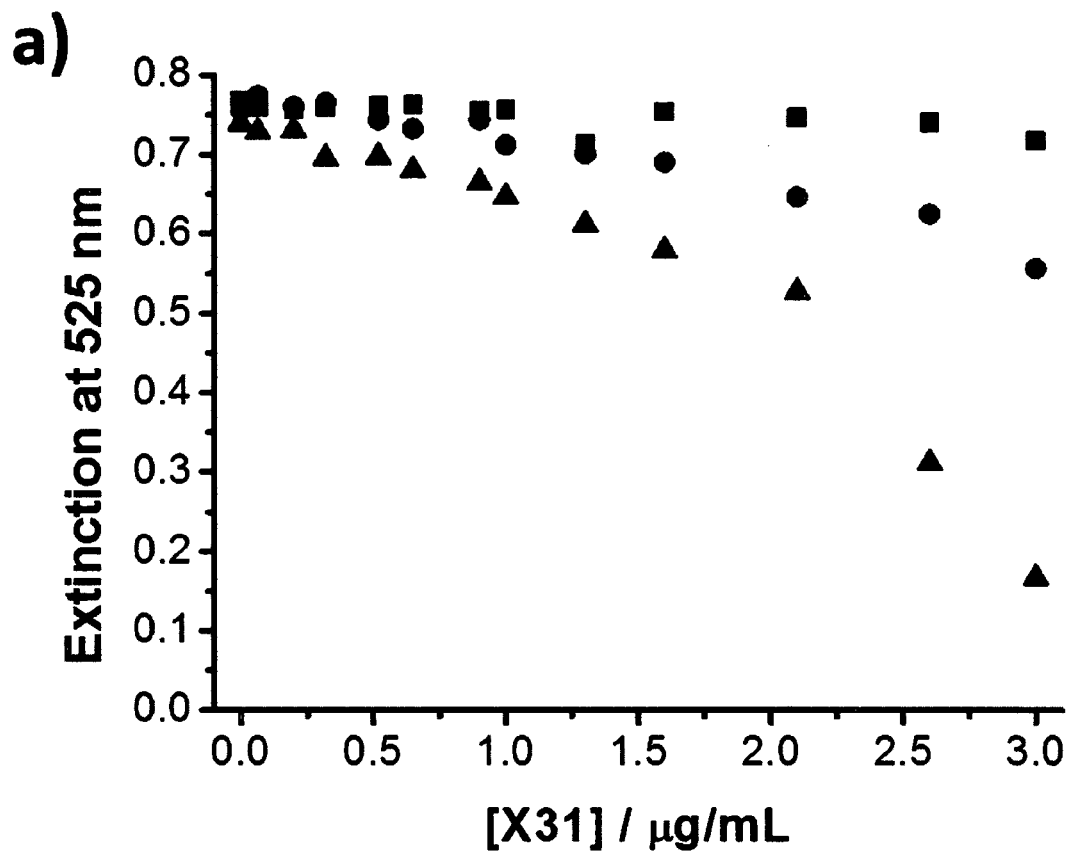
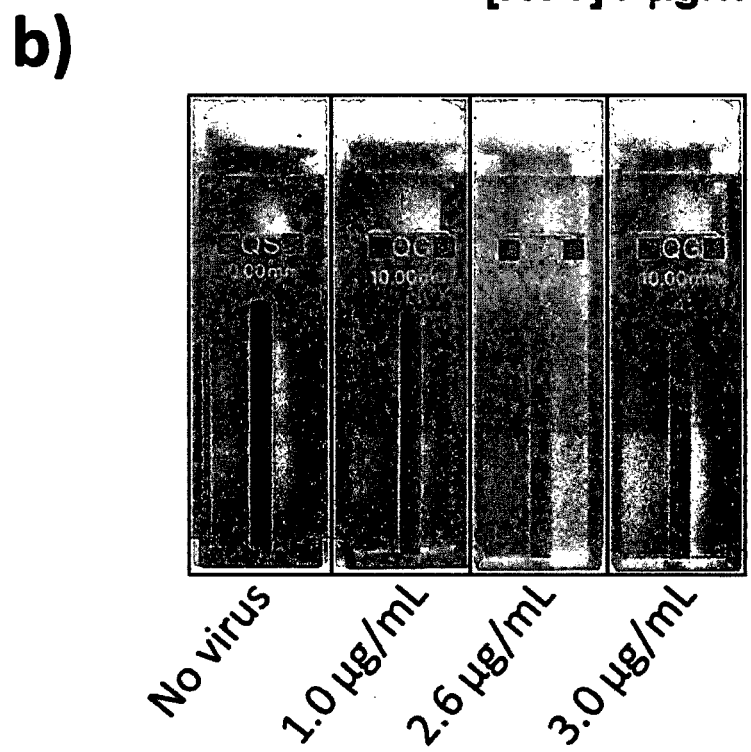

VIRUS DETECTION

This application is a 35 U.S.C. § 371 National Phase Entry Application of International Application No. PCT/GB2014/052026 filed Jul. 3, 2014, which designates the U.S., and which claims the benefit of GB Application No. 1313201.4 filed Jul. 24, 2013, the contents of each of which are incorporated herein by reference in their entirety.

TECHNICAL FIELD

The present invention relates generally to methods and materials for use in the detection of influenza viruses.

BACKGROUND ART

Seasonal influenza is the cause of tens to hundreds of thousands of human deaths each year.[1] However, of particular concern is the threat of a pandemic caused by the influenza virus crossing from animal species. A recent example of such an influenza pandemic is the influenza A (H1N1) 'swine flu' outbreak of 2009 which caused high morbidity and, in some cases, severe disease and mortality.

The influenza virus has two types of surface glycoproteins, haemagglutinin (HA) and neuraminidase (NA). The HA recognizes sialic acids present on the surface of host cells and binds to these carbohydrates in order to infect the cell and the NA releases progeny virus from the infected cell.[2] Measures to prevent a new influenza virus pandemic involve both vaccination and antiviral drugs, the latter ideally administered within 48 h of the infection.[3]

The effective use of antivirals requires rapid and early diagnosis. Current methods for the detection of influenza include: molecular identification of influenza isolates including reverse-transcription PCR, immunofluorescence antibody staining, virus isolation in cell culture or in embryonated chicken eggs, and serological diagnosis by haemagglutination inhibition or by microneutralization.[3b] All of these methods are time-consuming, taking several hours or even days for results to be obtained, and also require specialist equipment and trained analysts.

Gold nanoparticles (ca. 16 nm in diameter) in aqueous suspension exhibit an intense red color due to their surface plasmon absorption band. This optical property is distance-dependent and upon aggregation of the metal nanoparticles the solution changes color. The color change, readily observed with the naked eye, is due to the coupling interactions between the surface plasmon fields of the particles. Gold nanoparticle-based colorimetric assays have been reported [4] for the detection of a variety of species, including oligonucleotides, metal ions, anions, small organic molecules and proteins, a field reviewed recently by Rotello et al.[5] By functionalizing metal nanoparticles with specifically synthesized carbohydrate ligands, glyconanoparticles can be created.[6] Glyconanoparticle-based colorimetric assays have been used for the detection of lectins, calcium ions, and cholera toxin.[7]

Gold nanoparticles have been used for the inhibition of influenza virus. Papp et al. employed 14 nm gold nanoparticles functionalized with a sialic-acid-terminated glycerol dendron to inhibit X31 influenza virus (a reassortant H3N2 influenza virus carrying the HA and NA genes of A/Aichi/2/68).[8] In addition, gold nanoparticles coated with a phosphonate ester analogue of the influenza therapeutic Oseltamivir,[9] with mercaptoethanesulfonate and mercaptosuccinic acid,[10] and gold nanorods functionalized with ssRNA[11] have also been used for the inhibition of influenza virus.

Gold nanoparticles have also been used for the detection of influenza virus. Influenza A/Puerto Rico/8/34 (PR8) (H1N1) virus has been detected using antibody-functionalized gold nanoparticles and dynamic light scattering.[12] Gold nanoparticles functionalized with a chemically unmodified monomer of sialic acid have been used to colorimetrically detect influenza B viruses of the B/Victoria and B/Yamagata lineages through the interaction between the sialic acid and the HA on the virus.[13]

US 2008/0194801 relates to a reportedly novel library of compounds comprising a spacer with an attachment element on one terminus and a recognition element on the other terminus. The library of compounds can be attached to a solid support and used in sensors and biosensors.

WO 2011/130332 relates to glycan arrays that bind specific target HAs and are reported to detect and distinguish between various sub-types and strains of influenza virus. Methods for using the glycan arrays with assays using nanoparticle amplification technique are also reportedly disclosed.

WO2008/123844 relates to a method and system for detecting magnetic nanoparticles include measuring a magneto-optical enhancement of TP the plasmon absorption in the optical response.

US 2012/0015344 relates to a particulate composition formed from a conductive polymer bound to magnetic nanoparticles. The particulate composition can be formed into a biologically enhanced, electrically active magnetic (BEAM) nanoparticle composition by further including a binding pair member (e.g., an antibody or a fragment thereof that specifically recognizes a virus strain or a virus surface protein) bound to the conductive polymer of the particulate composition. Notwithstanding the above it can be seen that a rapid, diagnostic test that is simple to perform, works on unpurified samples, and is ideally able to discriminate between human influenza and emerging animal strains, such as the avian H5N1 'bird flu' virus that has generated considerable concern following its re-emergence in 2003-2004 or the avian H7N9 transmitted to humans in 2013, would provide a contribution to the art.

DISCLOSURE OF THE INVENTION

The present inventors have developed glyconanoparticles which include a novel glycoconjugate which presents an influenza-specific sialic acid moiety that can discriminate between influenza virus strains by virtue of its structure and the sialic acid linkage specificity of the corresponding HAs. These glyconanoparticles can be used to specifically and rapidly detect influenza viruses. Preferred glycoconjugates are trivalent, which format provides improved binding and specificity properties, and may better interact with the HA[15]. The inventors have demonstrated that ligands which present a sialic acid α2,6 galactose recognition group can be used to specifically detect human influenza virus. In other embodiments sialic acid α2,3 galactose sequences may be used to preferentially bind avian influenza virus[14].

The invention therefore provides methods of detecting influenza virus, as well as related materials and processes for producing the same.

Thus in one aspect of the present invention there is provided a method for specifically detecting a target influenza virus in a sample, which method comprises:

(a) providing a nanoparticle probe comprising a plurality of glycoconjugate ligands, each ligand having more than one sialic-acid containing recognition group (Y) coupled to the nanoparticle via a multivalent core, wherein the recognition group (Y) on the bioconjugate specifically binds to the hemagglutinin on the target influenza virus;

(b) contacting the nanoparticle probe and the sample under conditions effective to specifically bind the hemagglutinin of the target influenza virus to the recognition group (Y); wherein said specific binding generates a detectable plasmonic signal which is specific to the influenza virus;

(c) detecting the signal generated in step b).

Preferably the target influenza virus is a human influenza virus, and the signal generated in (c) is different to the signal generated by an avian influenza virus. However other specificities may be provided as described below.

"Different" in this context means readily distinguishable under the conditions used in (c) e.g. when compared using equivalent samples under comparable conditions. Preferably the signal generated by the non-target influenza virus is less than <50%, 40%, 30%, 20%, 10%, 5% of the signal generated by the target virus. "Signal" in this context relates to the changes (shift or intensity) of the surface plasmon absorption band. As shown in the Examples below, preferred nanoparticle probes specific for human influenza virus (tested using X31) target showed negligible changes in the plasmonic signal in the presence of an avian virus.

In preferred embodiments each glycoconjugate ligand comprises a trivalent core, whereby there are 3 recognition groups (Y) per ligand.

Thus each glycoconjugate ligand (GL) may be of the formula:

$$-\!\!\!\{\!\!-L-X-\![Y]_m$$

wherein:

Y is a sialic-acid containing recognition group;

In a preferred embodiment, Y terminates with the α-anomer of a sialic acid moiety, and the sialic acid moiety is bound to a pyranose monosaccharide unit (e.g., galactose) through a 2,6 glycosidic bond. Preferably the sialic acid moiety and monosaccharide are thio linked.

Y may further comprise a spacer moiety 'Z' which connects the sialic acid containing moiety to the core group X. This may comprise, for example, an alkylene or alkenylene group which may include amine, amide, ether, ester or thioester linkages, and optionally be interrupted by one or more heteroatoms and/or rings, including aromatic rings (e.g. benzene, pyridine or 1,2,3-triazole), which rings are optionally substituted.

m≥1 e.g. 3.

X is a preferably multivalent core moiety; this spaces group Y from the particle, and spaces the sialic-acid moieties in Y apart to optimise binding;

X may comprise groups as defined in 'Z'. It may comprise a multivalent carbon atom ("tripodal core") to which three Y recognition groups are linked (e.g. via $X^L$ groups):

$$Y\diagdown_{X^{L1}}\overset{\overset{Y}{\underset{|}{X^{L2}}}}{\diagup}_{X^{L3}}\diagup Y$$

$X^{L1}$, $X^{L2}$ and $X^{L3}$ may be, for example, —CH$_2$—O—CH$_2$—.

In preferred embodiments the anomeric centre of the sialic acid moiety or moieties of the Y groups are separated from the single multivalent core carbon atom by 20 to 30 bond lengths (e.g., 22 to 25 bond lengths) or 1.5 to 3 nm (e.g., 2 to 2.5 nm).

L is a linking moiety e.g. a thiolinkage; this facilitates attachment of the GL to the nanoparticle.

Processes for making the GL compounds described herein are also provided.

Nanoparticles useful in the practice of the invention include those known in the art for use in other nanoparticle probes and will be made of metal (e.g., gold, silver, platinum, cobalt), semiconductor (e.g., Si, CdSe, CdS, and CdS or CdSe coated with ZnS), core shell particles (e.g., gold coated silver particles), alloy particles (e.g. silver and gold alloy), magnetic (e.g., cobalt), and non-metallic (e.g. silicon) colloidal materials. Core shell particles are described in PCT applications PCT/US01/50825, and PCT/US02/16382, as well as in U.S. Pat. Nos. 7,147,687 and 7,238,172. Other nanoparticles composed of materials e.g. that have an affinity for thiol groups may also be used.

The nanoparticle is preferably a gold nanoparticle.

The size of the nanoparticles is preferably from about 5 nm to about 150 nm (mean diameter), more preferably from about 5 to about 50 nm, most preferably from about 10 to about 30 nm.

In these embodiments, the diameter of the nanoparticle may be, for example, 3 nm or greater, 3.5 nm or greater, 4 nm or greater, or 4.5 nm or greater.

In these embodiments, the diameter of the nanoparticle may be, for example, 10 nm or less, 15 nm or less, 20 nm or less, 30 nm or less, 40 nm or less, 50 nm or less, 75 nm or less, 100 nm or less.

The gold nanoparticle may have a diameter in the range of, for example, 3.5 nm to 15 nm, 3.5 to 20 nm, 3.5 to 40 nm, 3.5 nm to 50 nm, 3.5 nm to 75 nm, 3.5 nm to 100 nm.

A preferred diameter is c.16 nm e.g. 12, 13, 14, 15, 16, 17, 18, 19, or 20 nm.

Preferably the nanoparticle is a gold nanoparticle of around 16 nm diameter.

Each nanoparticle probe will generally have multiple glycoconjugate ligands attached, spread over the surface of the nanoparticle.

For example, the mean number of GL compounds per nanoparticle may be 5, 10, 25, 50, 100, or 200.

In some embodiments, the probe has one or more other ligands bound to the nanoparticle, in addition to the glycoconjugate ligands. A further ligand which does not bind specifically to influenza virus may be used to modulate density of the glycoconjugate ligand on the surface of the nanoparticle to optimise binding and specificity.

In one embodiment, the probe comprises polyethylene glycol (PEG), e.g. a thiolated PEG, bound to the solid support.

In one such embodiment, the polyethylene glycol is $H(OCH_2)_4S$—, bound to the nanoparticle through the sulphur atom.

In one embodiment, the probe comprises a phase transfer reagent bound to the solid support.

In one such embodiment, the phase transfer reagent is tetraoctylammonium halide, e.g., tetraoctylammonium bromide (TOAB)

The molar ratio of glycoconjugate ligand:further ligand (e.g. PEG) may be, for example, Between 10:10 and 90:10. Preferably the further ligand is in excess.

Non-limiting example ratios are 1:99; 5:95; 10:90; 25:75; 50:50; 75:25: or 90:10.

In a preferred embodiment, the ratio of glycoconjugate ligand:further ligand is between 15:85 and 35:65 e.g. between 20:80 and 30:70 e.g. about 25:75.

Preferably the detectable signal is a color change, which may be observable with the naked eye.

Preferably said specific binding in step (b) causes aggregation of the nanoparticles, wherein said aggregation generates or contributes to the detectable plasmonic signal.

Preferably the detectable signal is generated within 60, 50, 40, 30, 20, 10 or 5 mins.

The methods of the present invention can be used with little or no sample preparation. They can be used, for example, for detecting influenza viruses and/or virus particles in samples of animals and/or humans like swabs, faeces and blood, in environmental samples. In one embodiment, the methods of the present invention are used for detecting influenza viruses and/or virus particles in sputum or saliva samples of animals and/or humans.

Preferably the nanoparticle probes are utilised in an aqueous suspension.

Thus in one aspect, the present invention relates to a virus-detection solution, comprising an aqueous suspension of a glycoconjugate described above, bound to nanoparticles.

In one embodiment, the concentration of glycoconjugate-covered nanoparticles in the virus-detection solution is 0.05 nM to 10 nM, for example, 0.1 nM to 7.0 nM, or 1 nM to 5 nM.

In one embodiment, a sample of interest is added directly (neat) to the virus-detection solution. In another embodiment, a sample of interest is diluted prior to being added to the virus-detection solution.

In use the observation of a detectable plasmonic signal e.g. color change can be assessed using methods known in the art for other nanoparticle probes. Such an assessment with the naked eye can be made more readily against a background of a contrasting color. For instance, when gold nanoparticles are used, the observation of a color change is facilitated by spotting a sample of the hybridization solution on a solid white surface (such as silica or alumina TLC plates, filter paper, cellulose nitrate membranes, and nylon membranes, preferably a nylon membrane) and allowing the spot to dry. In the presence of the target virus the solution or spot may change from pink/red to a more blue spot.

The color change may be quantitated by recording the plate image with an optical scanning device such as a flatbed scanner or CCD camera, and analyzing the amount and type of color of each individual spot. Alternatively, a color filter (e.g. red filter) may be used to filter out specific colors so that the signal intensity of each spot may be recorded and analyzed.

Substrates which allow or facilitate observation of the detectable change may be used as is known in the art. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates).

Following detection via the methods described herein, samples may be subject to confirmatory tests like reverse transcription polymerase chain reaction.

In other aspects of the invention, the glycoconjugate ligands can be attached to different (non-nanoparticle) solid supports. The term "solid support" refers to a material having a rigid or semi-rigid surface which a compound of the present invention can bond to.

Such supports will preferably take the form of small beads, pins/crowns, laminar surfaces, pellets, disks.

The solid support may be part of detection system e.g. based on surface plasmon resonance, or surface enhanced Raman spectroscopy.

In other aspects of the invention, the glycoconjugate ligands can be attached to a fluorescent nanoparticle, e.g., a quantum dot, a fluorescently-tagged polymer bead, a fluorescently-tagged silica bead (e.g., silica nanoparticle) or a fluorescently-tagged magnetic bead (e.g., magnetic nanoparticle). It will be understood that any discussion herein with respect to gold nanoparticles, should be taken to apply mutatis mutandis to these other solid substrates, unless context demands otherwise.

Some preferred embodiments of the nanoparticle probes will now be discussed:

As explained above, in their broadest sense the nanoparticle probes of the present invention comprise:
- a plurality of optionally multi-valent glycoconjugate ligands,
- each ligand having at least one sialic-acid containing recognition group (Y),
- wherein Y is coupled to the nanoparticle via a core, which is optionally multivalent for Y.

In use, the recognition group (Y) on the bioconjugate specifically binds to the hemagglutinin on a target influenza virus, which specific binding generates a detectable plasmonic signal which is specific to the influenza virus.

The nanoparticle probes comprise a glycoconjugate ligand (GL) attached to a nanoparticle, wherein each GL compound comprises 1 or more, preferably 2, most preferably 3 sialic-acid containing recognition groups (Y), as shown in of formula (I):

(I)

The GL may be of the formula (II):

(II)

wherein:
Y is a sialic-acid containing recognition group;
m≥1 e.g. 1, 2, 3, or 4.
X is a core moiety; this spaces group Y from the particle, and where X is multivalent, spaces the sialic-acid moieties in Y apart;
L is a linking moiety; this facilitates attachment of the GL to the nanoparticle.

In one embodiment m is 3 to 6.
In one embodiment m is 3 to 5.
In one embodiment m is 3 or 4.
In a preferred embodiment, m is 3.

The sialic-acid containing recognition group, Y, comprises a sialic acid moiety attached to one or more monosaccharide units, with the monosaccharide units being attached to the core, X, by a bond or by a spacer moiety.

In a preferred embodiment, Y terminates with the α-anomer of a sialic acid moiety, and the sialic acid moiety is bound to a pyranose monosaccharide unit (e.g., galactose) through a 2,3 glycosidic bond.

In a preferred embodiment, Y terminates with the α-anomer of a sialic acid moiety, and the sialic acid moiety is bound to a pyranose monosaccharide unit (e.g., galactose) through a 2,6 glycosidic bond.

In a preferred embodiment, the anomeric centre of the sialic acid moiety is separated from the multivalent centre of the core moiety X by 20 to 30 bond lengths (e.g., 22 to 25 bond lengths). This is described in more detail hereinafter.

In a preferred embodiment, the anomeric centre of the sialic acid moiety is separated from the core moiety X by 1.5 to 3 nm (e.g., 2 to 2.5 nm).

In one embodiment, each sialic-acid containing recognition group Y is independently a moiety of the following formula:

(III)

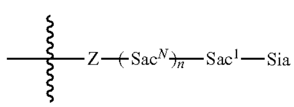

wherein:

Sia is a sialic acid moiety;

$Sac^1$ is a sialic-acid-attached monosaccharide-unit;

$Sac^N$ is a monosaccharide unit;

Z is a spacer moiety, or a single bond;

n≥0; and the wavy line 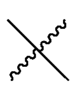 indicates the point of attachment to X.

In one embodiment, Y has a relative molecular weight of less than 5,000.

In one embodiment, Y has a relative molecular weight of less than 3,000.

In one embodiment, Y has a relative molecular weight of less than 2,000.

In one embodiment, Y has a relative molecular weight of less than 1,000.

In one embodiment, each core moiety, X, is attached to more than one type of sialic-acid containing recognition group, Y (e.g., sialic-acid containing recognition groups with different Sia, $Sac^1$, $Sac^N$, Z and or n). For example, the GL compound may have two different types of sialic-acid containing recognition group: $Y^1$ and $Y^2$, or three different types of sialic-acid containing recognition group: $Y^1$, $Y^2$ and $Y^3$.

However, in a preferred embodiment, each core moiety, X, is attached to only one type of sialic-acid containing recognition group, Y (i.e., all recognition groups have the same Sia, $Sac^1$, $Sac^N$, Z and n).

The sialic acid moiety, "Sia", is a moiety which is related to neuraminic acid, which has the following formula:

(IV)

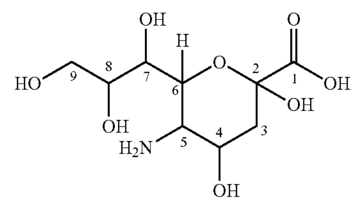

More specifically, the sialic acid moiety is a moiety of the following formula:

(V)

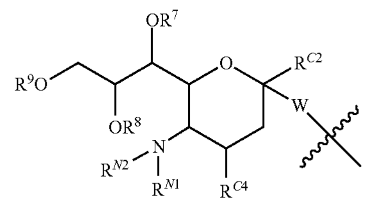

or a salt thereof;

wherein:

—W is S or C;

—$R^{C2}$ is $C(=O)OR^1$; $P(=O)(OR^{P1})(OR^{P2})$; or $S(=O)_2OR^{S1}$;

—$R^{C4}$ is $OR^4$ or $NR^{N4}R^{N5}$;

—$R^1$ is H or $R^{A1}$;

—$R^4$ is H or $R^{A4}$;

—$R^7$ is H or $R^{A7}$;

—$R^8$ is H or $R^{A8}$;

—$R^9$ is H or $R^{A9}$;

—$R^{N4}$ is H or $C_{1-6}$ alkyl;

—$R^{N5}$ is H; $C_{1-6}$ alkyl; $C(=NH)(NH_2)$ or $C(=O)C_{1-6}$ alkyl;

—$R^{A1}$ is $C_{1-6}$ alkyl;

—$R^{A4}$ is $C_{1-6}$ alkyl; $C(=O)C_{1-6}$ alkyl; $P(=O)(OR^{P1})(OR^{P2})$; or $S(=O)_2OR^{S1}$;

—$R^{A7}$ is $C_{1-6}$ alkyl; $C(=O)C_{1-6}$ alkyl; $P(=O)(OR^{P1})(OR^{P2})$; or $S(=O)_2OR^{S1}$;

—$R^{A8}$ is $C_{1-6}$ alkyl; $C(=O)C_{1-6}$ alkyl; $P(=O)(OR^{P1})(OR^{P2})$; or $S(=O)_2OR^{S1}$;

—$R^{A9}$ is $C_{1-6}$ alkyl; $C(=O)C_{1-6}$ alkyl; $P(=O)(OR^{P1})(OR^{P2})$; or $S(=O)_2OR^{S1}$;

—$R^{P1}$ is H or $C_{1-6}$ alkyl;

—$R^{P2}$ is H or $C_{1-6}$ alkyl;

—$R^{S1}$ is H or $C_{1-6}$ alkyl;

—$R^{N1}$ is H or $C_{1-6}$ alkyl;

—$R^{N2}$ is H; $C_{1-6}$ alkyl or $C(=O)R^{NN2}$;

—$R^{NN2}$ is $C_{1-6}$ alkyl or $CH_2OR^{NNN2}$;

—$R^{NN2}$ is H; $R^{NNN2}$ or C(=O)$R^{NNNN2}$;
—$R^{NNNN2}$ is $C_{1-6}$ alkyl; and
the wavy line

indicates the point of attachment to $Sac^1$.

wherein:
—W is S;
and $R^1$, $R^4$, $R^7$, $R^8$, $R^9$, $R^{N1}$, $R^{N2}$ and

are as defined above.

Examples of suitable moieties of formulae (V) and (VI) include, for example, the moieties shown in Table I.

TABLE I

Examples of sialic acid moieties falling within formulae (V) and (VI)

| Name | Abbreviation | Formula | Formula Reference |
|---|---|---|---|
| N-acetylneuraminic acid | Neu5Ac | 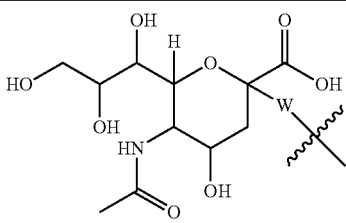 | (Sia-1) |
| N-glycolylneuraminic acid | Neu5Gc | 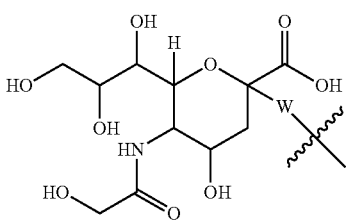 | (Sia-2) |
| N-acetyl-9-O-acetylneuraminic acid | 9-O-acetyl Neu5Ac | 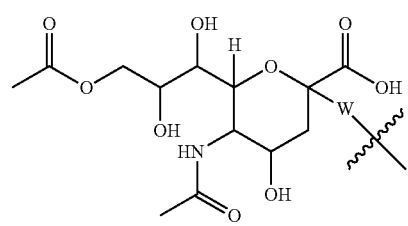 | (Sia-3) |

The term "$C_{1-6}$ alkyl" as used herein, pertains to a monovalent moiety obtained by removing a hydrogen atom from a carbon atom of a saturated hydrocarbon compound having from 1 to 6 carbon atoms. For groups with more than 3 carbon atoms, the group can be linear or branched.

In a preferred embodiment, the sialic acid moiety is a moiety of the following formula:

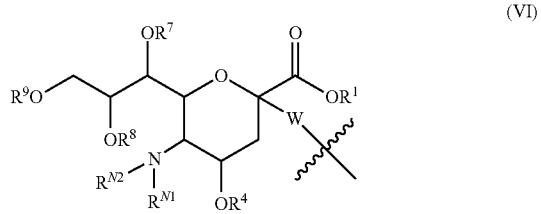

(VI)

or a salt thereof;

In one embodiment, Sia is a moiety of formula (Sia-1), (Sia-2), or (Sia-3).

In one embodiment, Sia is a moiety of formula (Sia-1) or (Sia-2).

In one embodiment, Sia is a moiety of formula (Sia-1).

Note that the Sia moiety of formula (V) above has at least six chiral centres, specifically, the carbon atoms marked with an asterisk (*) in the following formula. Each of the carbon atoms at these positions may be in either (R) or (S) configuration. Unless otherwise stated, a reference to one enantiomer/diastereomer is intended to be a reference to both enantiomers/all diastereomers.

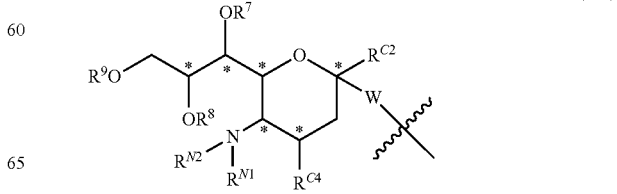

(VII)

In one embodiment, the sialic acid moiety is of the following formula:

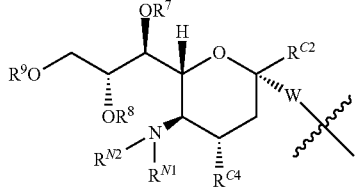
(VIII)

Note that this moiety can exist in two anomeric forms, designated alpha (α) and beta (β), as shown in the following formulae. "Anomers" are stereoisomers of a cyclic saccharide that differ only in their configuration at the hemiacetal or hemiketal carbon. The hemiacetal or hemiketal carbon of such molecules is known as the "anomeric carbon" or "anomeric centre". In the following formulae, the anomeric carbon/centre is marked with an asterisk (*).

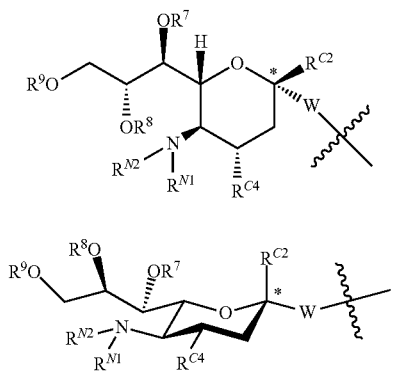

α-anomer

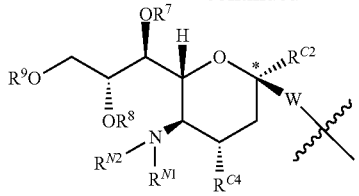

β-anomer

In the α-anomer the $R^{C2}$ group (e.g., $COOR^1$) is in the axial position. In the β-anomer the $R^{C2}$ group (e.g., $COOR^1$) is in the equatorial position.

In one embodiment, the sialic acid moiety Sia is the α-anomer.

In a preferred embodiment, the sialic acid moiety Sia is the α-anomer of a compound of formula (VI); that is, a moiety of formula (IX),

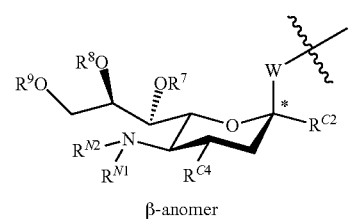
(IX)

Examples of sialic moieties falling within formula (IX) include, for example, the moieties shown in Table II.

TABLE II

Examples of sialic acid moieties falling within formula (IX)

| Name | Abbreviation | Formula | Formula Reference |
|---|---|---|---|
| N-acetylneuraminic acid | Neu5Ac | 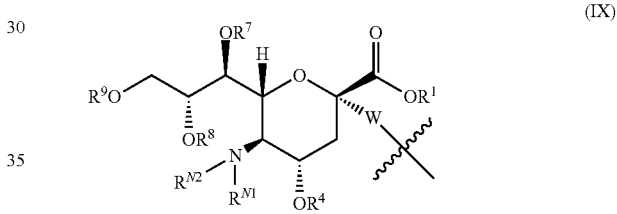 | (Sia-1a) |
| N-glycolylneuraminic acid | Neu5Gc | | (Sia-2a) |

TABLE II-continued

Examples of sialic acid moieties falling within formula (IX)

| Name | Abbreviation | Formula | Formula Reference |
|---|---|---|---|
| N-acetyl-9-O-acetylneuraminic acid | 9-O-acetyl Neu5Ac | [structure] | (Sia-3a) |

In one embodiment, Sia is a moiety of formula (Sia-1a), (Sia-2a), or (Sia-3a).

In one embodiment, Sia is a moiety of formula (Sia-1a) or (Sia-2a).

In one embodiment, Sia is a moiety of formula (Sia-1a).

In a preferred embodiment, Sia is a moiety of the following formula (X)

[structure]

In another preferred embodiment, Sia is a moiety of the following formula:

(XI)

[structure]

W

In one embodiment, W is S.
In one embodiment, W is C.

$R^{C2}$

In one embodiment, $R^{C2}$ is C(=O)OR$^1$.
In one embodiment, $R^{C2}$ is P(=O)(OR$^{P1}$)(OR$^{P2}$).
In one embodiment, $R^{C2}$ is S(=O)$_2$OR$^{S1}$.

$R^{C4}$

In one embodiment, $R^{C4}$ is OR$^4$.
In one embodiment, $R^{C4}$ is NR$^{N4}$R$^{N5}$.

$R^1$

In one embodiment, $R^1$ is H.
In one embodiment, $R^1$ is R$^{41}$.

$R^4$

In one embodiment, $R^4$ is H.
In one embodiment, $R^4$ is R$^{44}$.

$R^7$

In one embodiment, $R^7$ is H.
In one embodiment, $R^7$ is R$^{47}$.

$R^8$

In one embodiment, $R^8$ is H.
In one embodiment, $R^8$ is R$^{48}$.

$R^9$

In one embodiment, $R^9$ is H.
In one embodiment, $R^9$ is R$^{49}$.

$R^{N4}$

In one embodiment, $R^{N4}$ is H.
In one embodiment, $R^{N4}$ is $C_{1-6}$ alkyl.
In one embodiment, $R^{N4}$ is methyl, ethyl, i-propyl, n-propyl, t-butyl, i-butyl, s-butyl or n-butyl.
In one embodiment, $R^{N4}$ is methyl, ethyl, i-propyl, or n-propyl.
In one embodiment, $R^{N4}$ is methyl or ethyl.
In one embodiment, $R^{N4}$ is methyl.

$R^{N5}$

In one embodiment, $R^{N5}$ is H.
In embodiment, $R^{N5}$ is $C_{1-6}$ alkyl.
In one embodiment, $R^{N5}$ is methyl, ethyl, i-propyl, n-propyl, t-butyl, i-butyl, s-butyl or n-butyl.
In one embodiment, $R^{N5}$ is methyl, ethyl, i-propyl, or n-propyl.
In one embodiment, $R^{N5}$ is methyl or ethyl.
In one embodiment, $R^{N5}$ is methyl.
In one embodiment, $R^{N5}$ is C(=NH)(NH$_2$).
In one embodiment, $R^{N5}$ is C(=O)$C_{1-6}$ alkyl.
In one embodiment, $R^{N5}$ is C(=O)Me, C(=O)Et, C(=O)$^i$Pr, C(=O)$^n$Pr, C(=O)$^t$Bu, C(=O)$^i$Bu, C(=O)$^s$Bu, or C(=O)$^n$Bu.
In one embodiment, $R^{N5}$ is C(=O)Me, or C(=O)Et.
In one embodiment, $R^{N5}$ is C(=O)Me.

$R^{41}$

In one embodiment, $R^{41}$ is $C_{1-6}$ alkyl.
In one embodiment, $R^{41}$ is methyl, ethyl, i-propyl, n-propyl, t-butyl, i-butyl, s-butyl or n-butyl.
In one embodiment, $R^{41}$ is methyl, ethyl, i-propyl, or n-propyl.
In one embodiment, $R^{41}$ is methyl or ethyl.
In one embodiment, $R^{41}$ is methyl.

$R^{44}$

In one embodiment, $R^{44}$ is $C_{1-6}$ alkyl.
In one embodiment, $R^{44}$ is methyl, ethyl, i-propyl, n-propyl, t-butyl, i-butyl, s-butyl or n-butyl.
In one embodiment, $R^{44}$ is methyl, ethyl, i-propyl, or n-propyl.
In one embodiment, $R^{44}$ is methyl or ethyl.
In one embodiment, $R^{44}$ is methyl.
In one embodiment, $R^{44}$ is C(=O)$C_{1-6}$ alkyl.

In one embodiment, $R^{A4}$ is C(=O)Me, C(=O)Et, C(=O), $^iPr$, C(=O)$^nPr$, C(=O)$^tBu$, C(=O)$^iBu$, C(=O)$^sBu$, or C(=O)$^nBu$.
In one embodiment, $R^{A4}$ is C(=O)Me, or C(=O)Et.
In one embodiment, $R^{A4}$ is C(=O)Me.
$R^{A7}$
In one embodiment, $R^{A7}$ is $C_{1-6}$ alkyl.
In one embodiment, $R^{A7}$ is methyl, ethyl, i-propyl, n-propyl, t-butyl, i-butyl, s-butyl or n-butyl.
In one embodiment, $R^{A7}$ is methyl, ethyl, i-propyl, or n-propyl.
In one embodiment, $R^{A7}$ is methyl or ethyl.
In one embodiment, $R^{A7}$ is methyl.
In one embodiment, $R^{74}$ is C(=O)$C_{1-6}$ alkyl.
In one embodiment, $R^{A7}$ is C(=O)Me, C(=O)Et, C(=O), $^iPr$, C(=O)$^nPr$, C(=O)$^tBu$, C(=O)$^iBu$, C(=O)$^sBu$, or C(=O)$^nBu$.
In one embodiment, $R^{A7}$ is C(=O)Me, or C(=O)Et.
In one embodiment, $R^{A7}$ is C(=O)Me.
$R^{A8}$
In one embodiment, $R^{A8}$ is $C_{1-6}$ alkyl.
In one embodiment, $R^{A8}$ is methyl, ethyl, i-propyl, n-propyl, t-butyl, i-butyl, s-butyl or n-butyl.
In one embodiment, $R^{A8}$ is methyl, ethyl, i-propyl, or n-propyl.
In one embodiment, $R^{A8}$ is methyl or ethyl.
In one embodiment, $R^{A8}$ is methyl.
In one embodiment, $R^{A8}$ is C(=O)$C_{1-6}$ alkyl.
In one embodiment, $R^{A8}$ is C(=O)Me, C(=O)Et, C(=O), $^iPr$, C(=O)$^nPr$, C(=O)$^tBu$, C(=O)$^iBu$, C(=O)$^sBu$, or C(=O)$^nBu$.
In one embodiment, $R^{A8}$ is C(=O)Me, or C(=O)Et.
In one embodiment, $R^{A8}$ is C(=O)Me.
$R^{A9}$
In one embodiment, $R^{A9}$ is $C_{1-6}$ alkyl.
In one embodiment, $R^{A9}$ is methyl, ethyl, i-propyl, n-propyl, t-butyl, i-butyl, s-butyl or n-butyl.
In one embodiment, $R^{A9}$ is methyl, ethyl, i-propyl, or n-propyl.
In one embodiment, $R^{A9}$ is methyl or ethyl.
In one embodiment, $R^{A9}$ is methyl.
In one embodiment, $R^{A9}$ is C(=O)$C_{1-6}$ alkyl.
In one embodiment, $R^{A9}$ is C(=O)Me, C(=O)Et, C(=O), $^iPr$, C(=O)$^nPr$, C(=O)$^tBu$, C(=O)$^iBu$, C(=O)$^sBu$, or C(=O)$^nBu$.
In one embodiment, $R^{A9}$ is C(=O)Me, or C(=O)Et.
In one embodiment, $R^{A9}$ is C(=O)Me.
$R^{P1}$
In one embodiment, $R^{P1}$ is $C_{1-6}$ alkyl.
In one embodiment, $R^{P1}$ is methyl, ethyl, i-propyl, n-propyl, t-butyl, i-butyl, s-butyl or n-butyl.
In one embodiment, $R^{P1}$ is methyl, ethyl, i-propyl, or n-propyl.
In one embodiment, $R^{P1}$ is methyl or ethyl.
In one embodiment, $R^{P1}$ is methyl.
$R^{P2}$
In one embodiment, $R^{P2}$ is $C_{1-6}$ alkyl.
In one embodiment, $R^{P2}$ is methyl, ethyl, i-propyl, n-propyl, t-butyl, i-butyl, s-butyl or n-butyl.
In one embodiment, $R^{P2}$ is methyl, ethyl, i-propyl, or n-propyl.
In one embodiment, $R^{P2}$ is methyl or ethyl.
In one embodiment, $R^{P2}$ is methyl.
$R^{S1}$
In one embodiment, $R^{S1}$ is $C_{1-6}$ alkyl.
In one embodiment, $R^{S1}$ is methyl, ethyl, i-propyl, n-propyl, t-butyl, i-butyl, s-butyl or n-butyl.

In one embodiment, $R^{S1}$ is methyl, ethyl, i-propyl, or n-propyl.
In one embodiment, $R^{S1}$ is methyl or ethyl.
In one embodiment, $R^{S1}$ is methyl.
$R^{N1}$
In one embodiment, $R^{N1}$ is H.
In one embodiment, $R^{N1}$ is $C_{1-6}$ alkyl.
In one embodiment, $R^{N1}$ is methyl, ethyl, i-propyl, n-propyl, t-butyl, i-butyl, s-butyl or n-butyl.
In one embodiment, $R^{N1}$ is methyl, ethyl, i-propyl, or n-propyl.
In one embodiment, $R^{N1}$ is methyl or ethyl.
In one embodiment, $R^{N1}$ is methyl.
$R^{N2}$
In one embodiment, $R^{N2}$ is H.
In one embodiment, $R^{N2}$ is $C_{1-6}$ alkyl.
In one embodiment, $R^{N2}$ is methyl, ethyl, i-propyl, n-propyl, t-butyl, i-butyl, s-butyl or n-butyl.
In one embodiment, $R^{N2}$ is methyl, ethyl, i-propyl, or n-propyl.
In one embodiment, $R^{N2}$ is methyl or ethyl.
In one embodiment, $R^{N2}$ is methyl.
In one embodiment, $R^{N2}$ is C(=O)$R^{NN2}$.
$R^{NN2}$
In one embodiment, $R^{NN2}$ is $C_{1-6}$ alkyl.
In one embodiment, $R^{NN2}$ is methyl, ethyl, i-propyl, n-propyl, t-butyl, i-butyl, s-butyl or n-butyl.
In one embodiment, $R^{NN2}$ is methyl, ethyl, i-propyl, or n-propyl.
In one embodiment, $R^{NN2}$ is methyl or ethyl.
In one embodiment, $R^{NN2}$ is methyl.
In one embodiment, $R^{NN2}$ is $CH_2OR^{NNN2}$.
$R^{NNN2}$
In one embodiment, $R^{NNN2}$ is H.
In one embodiment, $R^{NNN2}$ is $R^{NNNN2}$.
In one embodiment, $R^{NNN2}$ is C(=O)$R^{NNNN2}$.
$R^{NNNN2}$
In one embodiment, $R^{NNNN2}$ is methyl, ethyl, i-propyl, n-propyl, t-butyl, i-butyl, s-butyl or n-butyl.
In one embodiment, $R^{NNNN2}$ is methyl, ethyl, i-propyl, or n-propyl.
In one embodiment, $R^{NNNN2}$ is methyl or ethyl.
In one embodiment, $R^{NNNN2}$ is methyl.
The sialic acid moiety, Sia, is attached to a monosaccharide unit, $Sac^1$, which is a pyranose-based monosaccharide.
It may be related, for example, to the pyranose form of a cyclic aldohexose, which has the following formula:

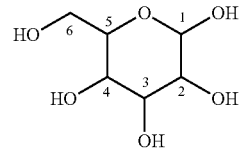

(XII)

In one embodiment, the monosaccharide unit $Sac^1$ is a compound of the following formula:

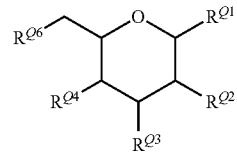

(XIII)

wherein;
one of $R^{Q1}$, $R^{Q2}$, $R^{Q3}$, $R^{Q4}$, and $R^{Q6}$ is a bond to W of the sialic acid moiety;
at least one or $R^{Q1}$, $R^{Q2}$, $R^{Q3}$, $R^{Q4}$, and $R^{Q6}$ is R' or OR', where:
R' is a bond to Z when n=0;
R' is a bond to $Sac^N$ when n>0;
and the remaining $R^{Q1}$, $R^{Q2}$, $R^{Q3}$, $R^{Q4}$, and $R^{Q6}$ are selected from the following groups:
$R^{Q1}$ is $OR^{QQ1}$ or $NHC(=O)R^{QQQ1}$;
$R^{Q2}$ is $OR^{QQ2}$ or $NHC(=O)R^{QQQ2}$;
$R^{Q3}$ is $OR^{QQ3}$ or $NHC(=O)R^{QQQ3}$;
$R^{Q4}$ is $OR^{QQ4}$ or $NHC(=O)R^{QQQ4}$;
$R^{Q6}$ is $OR^{QQ6}$ or $NHC(=O)R^{QQQ6}$;
$R^{QQ1}$ is H or $R^{QQQ1}$;
$R^{QQ2}$ is H or $R^{QQQ2}$;
$R^{QQ3}$ is H or $R^{QQQ3}$;
$R^{QQ4}$ is H or $R^{QQQ4}$;
$R^{QQ6}$ is H or $R^{QQQ6}$;
$R^{QQQ1}$ is $C_{1-6}$ alkyl;
$R^{QQQ2}$ is $C_{1-6}$ alkyl;
$R^{QQQ3}$ is $C_{1-6}$ alkyl;
$R^{QQQ4}$ is $C_{1-6}$ alkyl; and
$R^{QQQ6}$ is $C_{1-6}$ alkyl.

Note that this monosaccharide unit can exist in two anomeric forms, designated alpha (α) and beta (β). In the alpha anomeric form, the $R^{Q1}$ attached to anomeric carbon C-1 is cis to the group attached to C-5. In the beta anomeric form, $R^{Q1}$ attached to anomeric carbon C-1 is trans to the group attached to C-5.

Also note that the $Sac^1$ moiety of formula (XIII) above has at least five chiral centres, specifically, the carbon atoms at positions 1, 2, 3, 4, and 5, which are each marked with an asterisk (*) in the following formula. Each of the carbon atoms at these positions may be in either (R) or (S) configuration. Unless otherwise stated, a reference to one enantiomer/diastereomer is intended to be a reference to both enantiomers/all diasteromers.

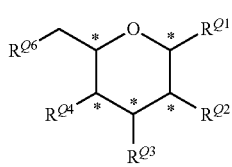

(XIV)

Suitable monosaccharide units include pyranose forms of, for example:
allose (All);
altrose (Alt);
galactose (Gal);
glucose (Glc);
gulose (Gul);
idose (Ido);
mannose (Man);
talose (Tal);
glucuronic acid; or
galacturonic acid;
and N-acetylated aminodeoxy derivatives thereof.

In a preferred embodiment, $Sac^1$ is a D-galactose unit. In other words, in a preferred embodiment, $Sac^1$ has the following formula:

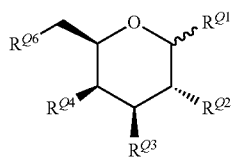

(XV)

In a particularly preferred embodiment, $Sac^1$ is the β-anomer of a galactose unit.

The monosaccharide unit $Sac^1$ is bonded to group W of the sialic acid moiety through a glycosidic bond. When W is S, this corresponds to an S-glycosidic bond. When W is C, this corresponds to a C-glycosidic bond.

It is possible for any of groups $R^{Q1}$, $R^{Q2}$, $R^{Q3}$, $R^{Q4}$, and $R^{Q6}$, to be a bond to group W of the sialic acid moiety, as shown in Table III.

TABLE III

| Bonding of $Sac^1$ to Sia, where ⤳⤲ indicates the point of attachment to W of Sia | | |
|---|---|---|
| Group corresponding to a bond to Sia | Nomenclature for type of bond | Formula |
| $R^{Q1}$ | 2.1 | |
| $R^{Q2}$ | 2.2 | |
| $R^{Q3}$ | 2.3 | |
| $R^{Q4}$ | 2.4 | |
| $R^{Q6}$ | 2.6 | |

$R^{Q1}$

In one embodiment, $R^{Q1}$ is a bond to W of the sialic acid moiety.

In one embodiment, $R^{Q1}$ is R'.
In one embodiment, $R^{Q1}$ is OR'.
In one embodiment, $R^{Q1}$ is $OR^{QQ1}$.
In one embodiment, $R^{Q1}$ is $NHC(=O)R^{QQQ1}$.

$R^{Q2}$

In one embodiment, $R^{Q2}$ is a bond to W of the sialic acid moiety.

In one embodiment, $R^{Q2}$ is R'.
In one embodiment, $R^{Q2}$ is OR'.
In one embodiment, $R^{Q2}$ is $OR^{QQ2}$.
In one embodiment, $R^{Q2}$ is $NHC(=O)R^{QQQ2}$.

$R^{Q3}$

In one embodiment, $R^{Q3}$ is a bond to W of the sialic acid moiety.

In a preferred embodiment, $Sac^1$ is a D-galactose unit linked to Sia through a 2,3 bond. In such an embodiment, $Sac^1$ has the following formula:

(XVI)

where indicates the point of attachment to W of Sia.

In a particularly preferred embodiment, $Sac^1$ is a D-galactose unit linked to Sia through an α-2,3 bond. In other words, Sia is an α-anomer, and is bonded to a D-galactose unit through a 2,3 glycosidic bond. In such an embodiment, Sia-$Sac^1$ are of the following formula:

(XVII)

In these preferred embodiments, it is preferred that the D-galactose unit is the β-anomer.

In one embodiment, $R^{Q3}$ is R'.
In one embodiment, $R^{Q3}$ is OR'.
In one embodiment, $R^{Q3}$ is $OR^{QQ3}$.
In one embodiment, $R^{Q3}$ is $NHC(=O)R^{QQQ3}$.

$R^{Q4}$

In one embodiment, $R^{Q4}$ is a bond to W of the sialic acid moiety.

In one embodiment, $R^{Q4}$ is R'.
In one embodiment, $R^{Q4}$ is OR'.
In one embodiment, $R^{Q4}$ is $OR^{QQ4}$.
In one embodiment, $R^{Q4}$ is $NHC(=O)R^{QQQ4}$.

$R^{Q6}$

In one embodiment, $R^{Q6}$ is a bond to W of the sialic acid moiety.

In a preferred embodiment, $Sac^1$ is a D-galactose unit linked to Sia through a 2,6 bond. In such an embodiment, $Sac^1$ has the following formula:

(XVIII)

where indicates the point of attachment to W of Sia.

In a particularly preferred embodiment, $Sac^1$ is a D-galactose unit linked to Sia through an α-2,6 bond. In other words, Sia is an α-anomer, and is bonded to a D-galactose unit through a 2,6 glycosidic bond. In such an embodiment, Sia-$Sac^1$ are of the following formula:

(XIX)

In these preferred embodiments, it is preferred that the D-galactose unit is the β-anomer.

In one embodiment, $R^{Q6}$ is R'.
In one embodiment, $R^{Q6}$ is OR'.
In one embodiment, $R^{Q6}$ is $OR^{QQ6}$.
In one embodiment, $R^{Q6}$ is $NHC(=O)R^{QQQ6}$.

$R^{QQ1}$

In one embodiment, $R^{QQ1}$ is H.
In one embodiment, $R^{QQ1}$ is $R^{QQQ1}$.

$R^{QQ2}$

In one embodiment, $R^{QQ2}$ is H.
In one embodiment, $R^{QQ2}$ is $R^{QQQ2}$.

$R^{QQ3}$

In one embodiment, $R^{QQ3}$ is H.
In one embodiment, $R^{QQ3}$ is $R^{QQQ3}$.

$R^{QQ4}$

In one embodiment, $R^{QQ4}$ is H.
In one embodiment, $R^{QQ4}$ is $R^{QQQ4}$.

$R^{QQ6}$

In one embodiment, $R^{QQ6}$ is H.
In one embodiment, $R^{QQ6}$ is $R^{QQQ6}$.

$R^{QQQ1}$

In one embodiment, $R^{QQQ1}$ is methyl, ethyl, i-propyl, n-propyl, t-butyl, i-butyl, s-butyl or n-butyl.
In one embodiment, $R^{QQQ1}$ is methyl, ethyl, i-propyl, or n-propyl.
In one embodiment, $R^{QQQ1}$ is methyl or ethyl.
In one embodiment, $R^{QQQ1}$ is methyl.

$R^{QQQ2}$

In one embodiment, $R^{QQQ2}$ is methyl, ethyl, i-propyl, n-propyl, t-butyl, i-butyl, s-butyl or n-butyl.
In one embodiment, $R^{QQQ2}$ is methyl, ethyl, i-propyl, or n-propyl.
In one embodiment, $R^{QQQ2}$ is methyl or ethyl.
In one embodiment, $R^{QQQ2}$ is methyl.

$R^{QQQ3}$

In one embodiment, $R^{QQQ3}$ is methyl, ethyl, i-propyl, n-propyl, t-butyl, i-butyl, s-butyl or n-butyl.
In one embodiment, $R^{QQQ3}$ is methyl, ethyl, i-propyl, or n-propyl.
In one embodiment, $R^{QQQ3}$ is methyl or ethyl.
In one embodiment, $R^{QQQ3}$ is methyl.

$R^{QQQ4}$

In one embodiment, $R^{QQQ4}$ is methyl, ethyl, i-propyl, n-propyl, t-butyl, i-butyl, s-butyl or n-butyl.
In one embodiment, $R^{QQQ4}$ is methyl, ethyl, i-propyl, or n-propyl.
In one embodiment, $R^{QQQ4}$ is methyl or ethyl.
In one embodiment, $R^{QQQ4}$ is methyl.

$R^{QQQ6}$

In one embodiment, $R^{QQQ6}$ is methyl, ethyl, i-propyl, n-propyl, t-butyl, i-butyl, s-butyl or n-butyl.
In one embodiment, $R^{QQQ6}$ is methyl, ethyl, i-propyl, or n-propyl.
In one embodiment, $R^{QQQ6}$ is methyl or ethyl.
In one embodiment, $R^{QQQ6}$ is methyl.

$Sac^N$

The compound may include additional monosaccharide units, $Sac^N$, in addition to the sialic-acid-attached monosaccharide unit, $Sac^1$.

The number of $Sac^N$ units present is determined by the integer n.

In one embodiment, n is 0 to 10.
In one embodiment, n is 0 to 8.
In one embodiment, n is 0 to 6.
In one embodiment, n is 0 to 5.
In one embodiment, n is 0 to 4.
In one embodiment, n is 0 to 3.
In one embodiment, n is 0 to 2.
In one embodiment, n is 0 or 1.
In one embodiment, n is 0 (i.e., no $Sac^N$ are present).
In one embodiment, n ≥1 (i.e., one or more $Sac^N$ are present). For example, n may be 1 to 10, 1 to 8, 1 to 6, 1 to 5, 1 to 4, 1 to 3, or 1 to 2.
In one embodiment, n is 1 (i.e., one $Sac^N$ unit is present). In such an embodiment, $Sac^1$ and $Sac^N$ form a disaccharide.

Suitable monosaccharide units include pyranose forms of, for example:
allose (All);
altrose (Alt);
galactose (Gal);
glucose (Glc);
gulose (Gul);
idose (Ido);
mannose (Man);
talose (Tal);
glucuronic acid; or
galacturonic acid;
as well as derivatives thereof (e.g., deoxy and aminodeoxy derivatives thereof, and ester-, amide- and acetyl-functionalised versions of any of the foregoing).

In one embodiment, $Sac^N$ is selected from one of the monosaccharide units shown in Table IV:

TABLE IV

Suitable $Sac^N$ units

| Name | Abbreviation | Formula | Formula Reference |
|---|---|---|---|
| D-galactose | Gal | 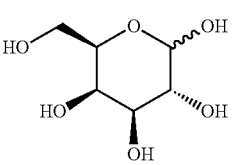 [SMILES: OC[C@H]1OC(O)[C@H](O)[C@@H](O)[C@H]1O] | (Sac-1) |
| α-D-galactose | α-Gal | 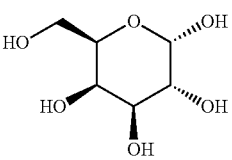 | (Sac-1a) |
| β-D-galactose | β-Gal | 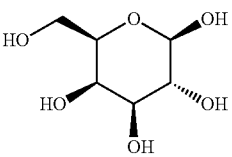 [SMILES: OC[C@H]1O[C@@H](O)[C@H](O)[C@@H](O)[C@H]1O] | (Sac-1b) |
| D-glucose | Glc | 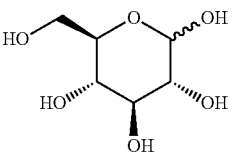 | (Sac-2) |
| α-D-glucose | α-Glc | 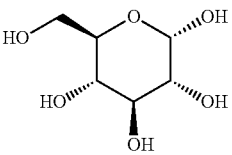 | (Sac-2a) |
| β-D-glucose | β-Glc | 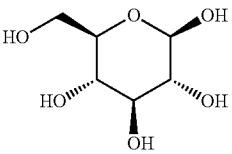 | (Sac-2b) |

In one embodiment $Sac^1$ is bound to a monosaccharide unit of formula (Sac-2b).

Examples of suitable monosaccharide moieties based on N-acetylated aminodeoxy aldohexoses are shown in Table V:

TABLE V

Suitable Sac$^N$ units

| Name | Abbreviation | Formula | Formula Reference |
|---|---|---|---|
| N-acetyl-galactosamine | GalNac | [structure] | (Sac-5) |
| α-N-acetyl-galactosamine | α-GalNAc | [structure] | (Sac-5a) |
| β-N-acetyl-galactosamine | β-GalNac | [structure] | (Sac-5b) |
| N-acetyl-glucosamine | GlcNac | [structure] | (Sac-6) |
| α-N-acetyl-glucosamine | α-GlcNAc | [structure] | (Sac-6a) |
| β-N-acetyl-glucosamine | β-GlcNAc | [structure] | (Sac-6b) |

In one embodiment, Z is a single bond.

However, in a preferred embodiment, Z is a spacer moiety.

The spacer moiety is a bifunctional or multifunctional moiety which is used to link the core moiety to Sac$^1$ (when n=0) or Sac$^N$ (when n>0).

Advantageously, the spacer moiety allows the length, composition and rigidity of the sialic-acid containing recognition group, Y to be modified. This permits the sialic-acid containing recognition groups to be presented to the binding sites of haemagglutinin whilst minimising strain in the glycoconjugate ligand compound.

In one embodiment, Z is a $C_{1-20}$ alkylene group (e.g., a $C_{1-15}$ or $C_{1-10}$ alkylene group).

The term "$C_{1-20}$ alkylene", as used herein, pertains to a bidentate moiety obtained by removing two hydrogen atoms, either both from the same carbon atom, or one from each of two different carbon atoms, of a saturated hydrocarbon compound having from 1 to 20 carbon atoms (unless otherwise specified), which may be aliphatic or alicyclic.

In one embodiment, the alkylene group is a linear aliphatic alkylene group.

In one embodiment, Z is a $C_{1-20}$ alkenylene group having 1 to 3 carbon-carbon double bonds (e.g., a $C_{1-15}$ or $C_{1-10}$ alkenylene group).

The term "$C_{1-20}$ alkenylene having 1 to 3 carbon-carbon double bonds", as used herein, pertains to a bidentate moiety obtained by removing two hydrogen atoms, either both from the same carbon atom, or one from each of two different carbon atoms, of a hydrocarbon compound having from 1 to 20 carbon atoms (unless otherwise specified) and one to three carbon-carbon double bonds, which may be aliphatic or alicyclic.

In one embodiment, Z is a $C_{1-20}$ alkynylene group having 1 to 3 carbon-carbon triple bonds (e.g., a $C_{1-15}$ or $C_{1-10}$ alkynylene group).

The term "$C_{1-20}$ alkynylene having 1 to 3 carbon-carbon double bonds", as used herein, pertains to a bidentate moiety obtained by removing two hydrogen atoms, either both from the same carbon atom, or one from each of two different carbon atoms, of a hydrocarbon compound having from 1 to 20 carbon atoms (unless otherwise specified) and one to three carbon-carbon triple bonds, which may be aliphatic or alicyclic.

The Z groups may optionally include one or more amine, amide, ether, ester or thioester linkages.

The Z groups above may be optionally interrupted by one or more heteroatoms and/or aromatic rings (e.g. benzene, pyridine, or 1,2,3-triazole) which rings are optionally substituted.

In one embodiment, Z comprises an alkylene or alkenylene group which optionally includes one or more amine, amide, ether, ester or thioester linkages, and optionally is interrupted by one or more heteroatoms (e.g., O, S, N) and/or aromatic rings (e.g., pyridine, benzene, 1,2,3-triazole).

In one embodiment, Z comprises a triazole group.

In one embodiment, Z comprises an amide linkage.

In one embodiment, Z is a $C_{1-20}$ amine group (e.g., a $C_{1-15}$ or $C_{1-10}$ amine group).

In one embodiment, Z is a $C_{1-20}$ amide group (e.g., a $C_{1-15}$ or $C_{1-10}$ amide group).

In one embodiment, Z is a $C_{1-20}$ ether group (e.g., a $C_{1-15}$ or $C_{1-10}$ ether group, or a $C_{1-20}$, $C_{1-15}$ or $C_{1-10}$ polyether group).

In one embodiment, Z is a $C_{1-20}$ ester group (e.g., a $C_{1-15}$ or $C_{1-10}$ ester group).

In one embodiment, Z is a $C_{1-20}$ thioether group (e.g., a $C_{1-15}$ or $C_{1-10}$ thioether group, or a $C_{1-20}$, $C_{1-15}$ or $C_{1-10}$ polythioether group).

In one embodiment, Z includes a first functional group, $A^1$, which connects Z to X.

In one embodiment, $A^1$ is selected from:

-a $C_{6-10}$ arylene group;

-a $C_{5-10}$ heteroarylene group;

—C(═O)NH—;

—C(═O)O—;

—NHC(═O)—;

—OC(═O)—;

—OC(═O)O—;

—NHC(═O)O—;

—OC(═O)NH—;

—NHC(═O)NH—;

—C(═O)NHC(═O)—;

—C(═O)—;

In one embodiment, $A^1$ is a $C_{6-10}$ arylene group or a $C_{5-10}$ heteroarylene group.

In one embodiment, $A^1$ is a $C_{5-10}$ heteroarylene group.

In one embodiment, $A^1$ is a group obtained by CLICK chemistry.

In one embodiment, $A^1$ is a group obtained by 1,3-dipolar cycloaddition.

In one embodiment, $A^1$ is a 1,2,3-triazole group. For example, $A^1$ may be a group having the following formula:

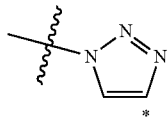
(XX)

wherein the wavy line

indicates the point of attachment to the rest of Z, and the asterisk * indicates the carbon to which X is attached.

Such a group can be obtained through Huisgen cycloaddition between an azide group and an alkyne group.

In one embodiment, Z includes a second functional group, $A^2$, which connects Z to $Sac^1$ (when n is 0) or $Sac^N$ (when n>0).

In one embodiment, $A^2$ is selected from
-a $C_{6-10}$ arylene group;
-a $C_{5-10}$ heteroarylene group;
—$R^{A2}$C(=O)NH—;
—$R^{A2}$C(=O)O—;
—$R^{A2}$NHC(=O)—;
—$R^{A2}$OC(=O)—;
—$R^{A2}$OC(=O)O—;
—$R^{A2}$NHC(=O)O—;
—$R^{A2}$OC(=O)NH—;
—$R^{A2}$NHC(=O)NH—;
—$R^{A2}$C(=O)NHC(=O)—;
—$R^{A2}$C(=O)—;
—$R^{A2}$S—;
—$R^{A2}$S—S—; or
—$R^{A2}$=N—NH—;
wherein $R^{A2}$ is H or $C_{1-6}$ alkylene.

In one embodiment, $A^2$ is —$R^{A2}$NH(C=O)— and $R^{A2}$ is $C_{1-6}$ alkylene.

In one embodiment, $A^2$ is —$R^{A2}$NH(C=O)— and $R^{A2}$ is —CH$_2$—, —C$_2$H$_4$—, —C$_3$H$_6$—, or —C$_4$H$_8$—.

In one embodiment, $A^2$ is —$R^{A2}$NH(C=O)— and $R^{A2}$ is —C$_3$H$_6$—.

In one embodiment, Z is a moiety having the following formula:

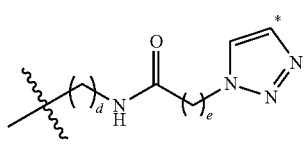
(XXI)

wherein:
d is 1 to 6;
e is 1 to 6; and
the wavy line

indicates the point of attachment to $Sac^1$ or $Sac^N$, and the asterisk * indicates the carbon to which X is attached.

In one embodiment, d is 3 and e is 5.

The core moiety X is a group to which the sialic-acid containing recognition groups, Y, are attached.

In one embodiment, X is a $C_{1-30}$ group to which Y is attached (e.g., a $C_{1-20}$ group, or a $C_{1-15}$ group).

In one embodiment, X is a $C_{1-30}$ alkylene group (e.g., a $C_{1-20}$ alkylene group or a $C_{1-15}$ alkylene group).

In one embodiment, X is a $C_{1-30}$ alkenylene group, the group having 1 to 3 carbon-carbon double bonds (e.g., a $C_{1-20}$ alkenylene group or a $C_{1-15}$ alkenylene group).

In one embodiment, X is a $C_{1-30}$ alkynylene group, the group having 1 to 3 carbon-carbon triple bonds (e.g., a $C_{1-20}$ alkynylene group or a $C_{1-15}$ alkynylene group).

In one embodiment, X is a $C_{1-30}$ amine group (e.g., a $C_{1-20}$ or $C_{1-15}$ amine group).

In one embodiment, X is a $C_{1-30}$ amide group (e.g., a $C_{1-20}$ or $C_{1-15}$ amide group).

In one embodiment, X is a $C_{1-30}$ ether group (e.g., a $C_{1-20}$ or $C_{1-15}$ ether group, or a $C_{1-30}$, $C_{1-20}$ or $C_{1-15}$ polyether group).

In one embodiment, X is a $C_{1-30}$ ester group (e.g., a $C_{1-12}$ or $C_{1-15}$ ester group).

In one embodiment, X is a $C_{1-30}$ thioether group (e.g., a $C_{1-20}$ or $C_{1-15}$ thioether group, or a $C_{1-30}$, $C_{1-20}$ or $C_{1-15}$ polythioether group).

The X groups above are optionally interrupted by one or more heteroatoms (e.g., O, S, N), aromatic rings (e.g., benzene, pyridine or 1,2,3-triazole), or other functional groups (e.g., —C(=O)NH—; —C(=O)O—; —NHC(=O)—; —OC(=O)—; —OC(=O)O—; —NHC(=O)O—; —OC(=O)NH—; —NHC(=O)NH—; —O(=O)NHC(=O)—; —C(=O)—; —S—S—; or =N—NH—).

In a preferred embodiment, three Y recognition groups are linked to a single carbon atom on the core moiety, as shown in the following formula:

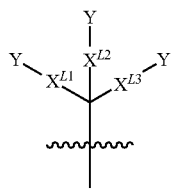
(XXII)

wherein:
$X^{L1}$, $X^{L2}$ and $X^{L3}$ are linking groups, and the wavy line

indicates the point of attachment to the rest of X.

In one embodiment, $X^{L1}$, $X^{L2}$ and $X^{L3}$ are, $R^{X1}OR^{X2}$, $R^{X1}NHR^{X2}$ or $R^{X1}SR^{X2}$, where $R^{X1}$ is a bond or $C_{1-6}$ alkylene and $R^{X2}$ is a bond or $C_{1-6}$ alkylene.

In one embodiment, three Y recognition groups are linked (e.g. via $X^L$ groups) to the same single multivalent carbon atom ("tripodal core") of the core moiety, and the anomeric centre of the sialic acid moiety is separated from said single carbon atom by 20 to 30 bond lengths (e.g., 22 to 25 bond lengths).

In one embodiment, three Y recognition groups are linked to the single carbon atom on the core moiety, and the anomeric centre of the sialic acid moiety is separated from said single carbon atom by 1.5 to 3 nm (e.g., 2 to 2.5 nm).

In one embodiment, X is a moiety having the following formula:

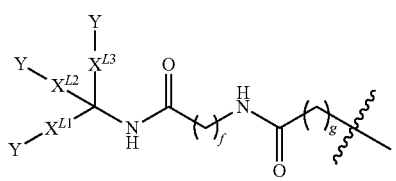

(XXIII)

wherein:

$X^{L1}$, $X^{L2}$ and $X^{L3}$ are linking groups;

f is 1 to 6;

g is 1 to 6; and and the wavy line

indicates the point of attachment to L.

In one embodiment, f is 4 and g is 3.

In one embodiment, $X^{L1}$, $X^{L2}$ and $X^{L3}$ are —CH$_2$—O—CH$_2$— or —CH$_2$—S—CH$_2$—.

In a preferred embodiment, X is a moiety of the following formula:

(XXIV)

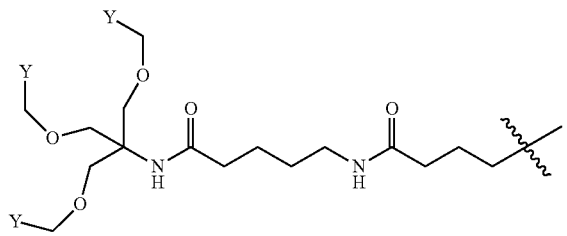

The linking moiety L, comprises a functional group which attaches the core moiety X to the nanoparticle.

In one embodiment, L is a sulphur atom, S, which binds to the nanoparticle, i.e., a moiety of the following formula:

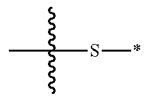

(XXV)

wherein the wavy line

indicates the point of attachment to X and the asterisk * indicates the point of attached to nanoparticle O.

In one embodiment, L is derived from a 1,2-dithiolane. For example, in one embodiment, L is a moiety of the following formula:

(XXVI)

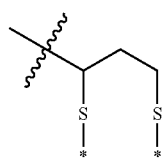

wherein the wavy line

indicates the point of attachment to X and the asterisk * indicates the point of attached to nanoparticle O.

For example, L may be derived from the 1,2-dithiolane group of thioctic acid (lipoic acid) or thioctic acid amide, or derivatives thereof.

In a preferred embodiment, the conjugate is of formula (I):

(I)

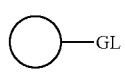

wherein:

O is a nanoparticle; and

GL is a glycoconjugate ligand compound of formula (II):

(II)

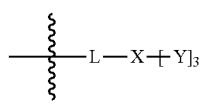

Y is a sialic-acid containing recognition group of formula (III):

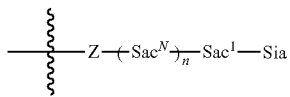

(III)

Where n=0, and Sia-Sac¹ together form a sialic acid α2,6 or α2,3 galactosyl moiety e.g. of formula (XXVII) or (XXVIII):

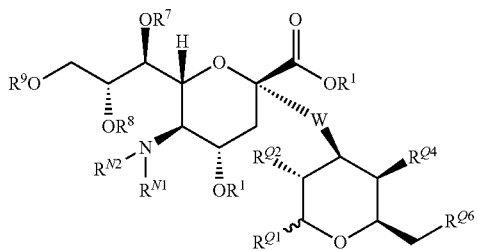

(XXVII)

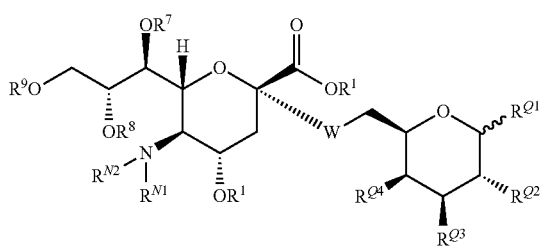

(XXVIII)

W is S;

$R^1$, $R^4$, $R^{N1}$, $R^7$, $R^8$ and $R^9$ are H;

$R^{Q1}$ is OR';

$R^{Q2}$, $R^{Q3}$, $R^{Q4}$ and $R^{Q8}$ are OH;

$R^{N2}$ is C(=O)$R^{NN2}$;

wherein n, $R^{NN2}$, R', Z, X and L are as defined above.

In this preferred embodiment, it is preferred that O in formula (I) is a gold nanoparticle.

In this preferred embodiment, it is preferred that:

Z is a moiety of formula (XXI):

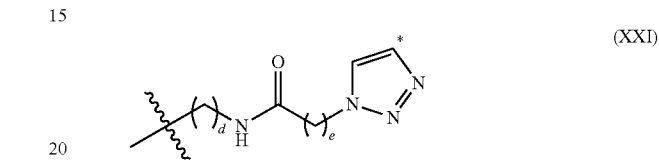

(XXI)

X is a moiety of formula (XXIII):

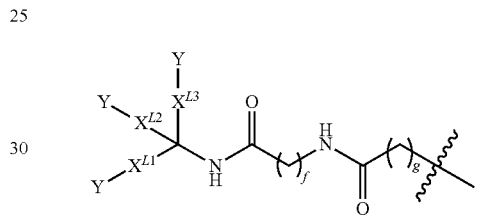

(XXIII)

L is S;

and n, W, d, e, f, g, $X^{L1}$, $X^{L2}$ and $X^{L3}$ are as defined above.

In this preferred embodiment, it is preferred that n is 0.

In this preferred embodiment, it is preferred that d is 3 and e is 5.

In this preferred embodiment, it is preferred that f is 5 and g is 4.

In this preferred embodiment, it is preferred that $X^{L1}$, $X^{L2}$ and $X^{L3}$ are —CH₂—O—CH₂.

In this preferred embodiment, it is preferred that the conjugate additionally comprises polyethylene glycol, preferably at an HB to PEG ratio of 25:75.

In a preferred embodiment, the glycoconjugate ligand has the following formula:

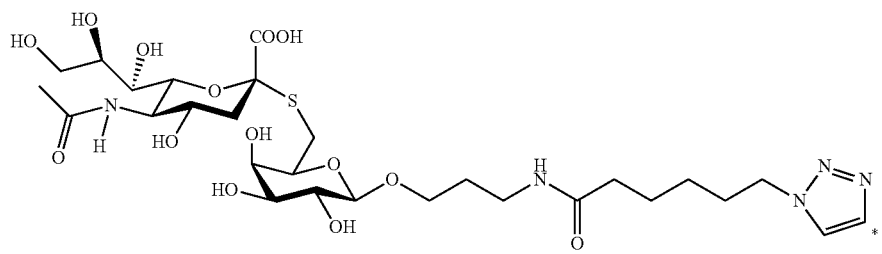

where the asterisk (*) indicates the carbon atom to which X is attached.

In a preferred embodiment, the conjugate has the following formula:

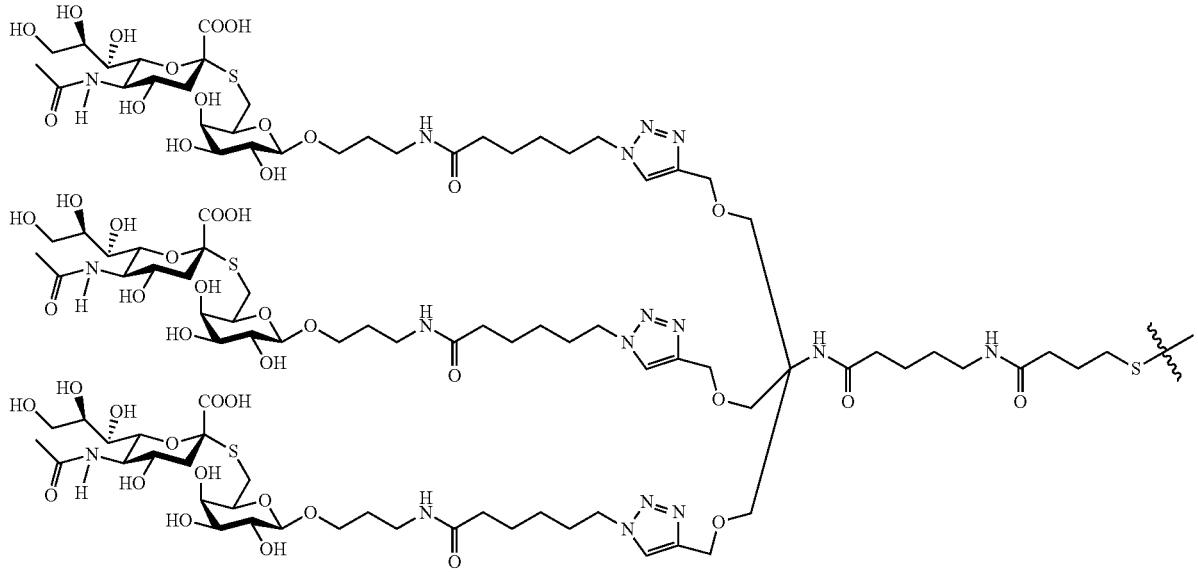

The present invention also relates to glycoconjugate ligand compounds which can be attached to a nanoparticle to make nanoparticle probes, and precursors of such compounds. Thus, in a further aspect, the present invention relates to a glycoconjugate ligand compound of the following formula:

(XXIX)

wherein:

X, Y and m are as defined above.

In a further aspect, the present invention relates to a glycoconjugate ligand compound of the following formula:

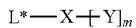
(XXX)

wherein:

X, Y, and m are as defined above; and

L* is a linking moiety, for attaching the compound to a nanoparticle.

The linking moiety L*, comprises a functional group which can attach the core moiety X to a nanoparticle.

In one embodiment, L is a thiol group (e.g., SH).

Unless otherwise specified, included in the above are the well-known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR$^a$R$^b$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

The nanoparticle probes described herein form one aspect of the present invention, as do kits comprising them.

Glycoconjugates of the present invention may be prepared using conventional methods known in the art, or by adapting conventional methods known in the art in conventional ways.

The synthesis of a sialic-acid containing recognition group with an S-glycosidic bond (W=S) is described below. Sialic-acid containing recognition groups with C-glycosidic bonds (W=C) can be made using, for example, the methods described in Glycoscience: Chemistry and Chemical Biology (for example, in the section entitled "C-Oligosaccharide synthesis"[31]), and Sodeoka[32].

Synthesis of sialic acid moieties where $R^{C4}$ is —NR$^{N4}$R$^{N5}$ can be made using, for example, the methods described in Vonitzstein[33].

Synthesis of sialic acid moieties where $R^{C2}$ is P(=O)(OR$^{P1}$)(OR$^{P2}$) can be made using, for example, methods analogous to those described in Stanley[34].

In a further aspect, the present invention relates to methods of making a glycoconjugate as described above.

In one embodiment, the method of making a glycoconjugate comprises:

(i) creating a sialic-acid containing recognition group (Y) for binding HA by attaching one or more monosaccharide units to a sialic acid;

(ii) attaching three or more sialic-acid containing recognition groups (Y) to a core moiety (X) comprising a linking moiety (L);

A probe of the present invention may be provided by:

(iii) attaching the glycoconjugate ligand compound to a nanoparticle, via a linker moiety (L).

In one embodiment, the step of creating group Y includes the step of reacting the monosaccharide units with a spacer moiety (Z).

In one embodiment, step (i) involves forming an α-2,3 glycosidic bond between sialic acid and one of the one or more monosaccharide units.

In one embodiment, step (i) involves forming an α-2,6 glycosidic bond between sialic acid and one of the one or more monosaccharide units.

In one embodiment, the step of attaching three or more glycoconjugate ligands to a core moiety includes carrying out a 1,3 dipolar cycloaddition.

In one embodiment, the 1,3 dipolar cycloaddition involves cycloaddition of a propargyl-ether-moiety and an azide moiety.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups defined above are specifically embraced by the present invention and are disclosed herein just as if each and every combination was individually and explicitly disclosed, to the extent that such combinations embrace glycoconjugates that are stable glycoconjugates (i.e., can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

FIGURES

FIG. 1. Schematic representation of the aggregation of the glyconanoparticles in the presence of the influenza virus. The trivalent ligand 1 on the surface of the gold nanoparticles binds to the haemagglutinin on the surface of the virus inducing aggregation.

Figure 2:
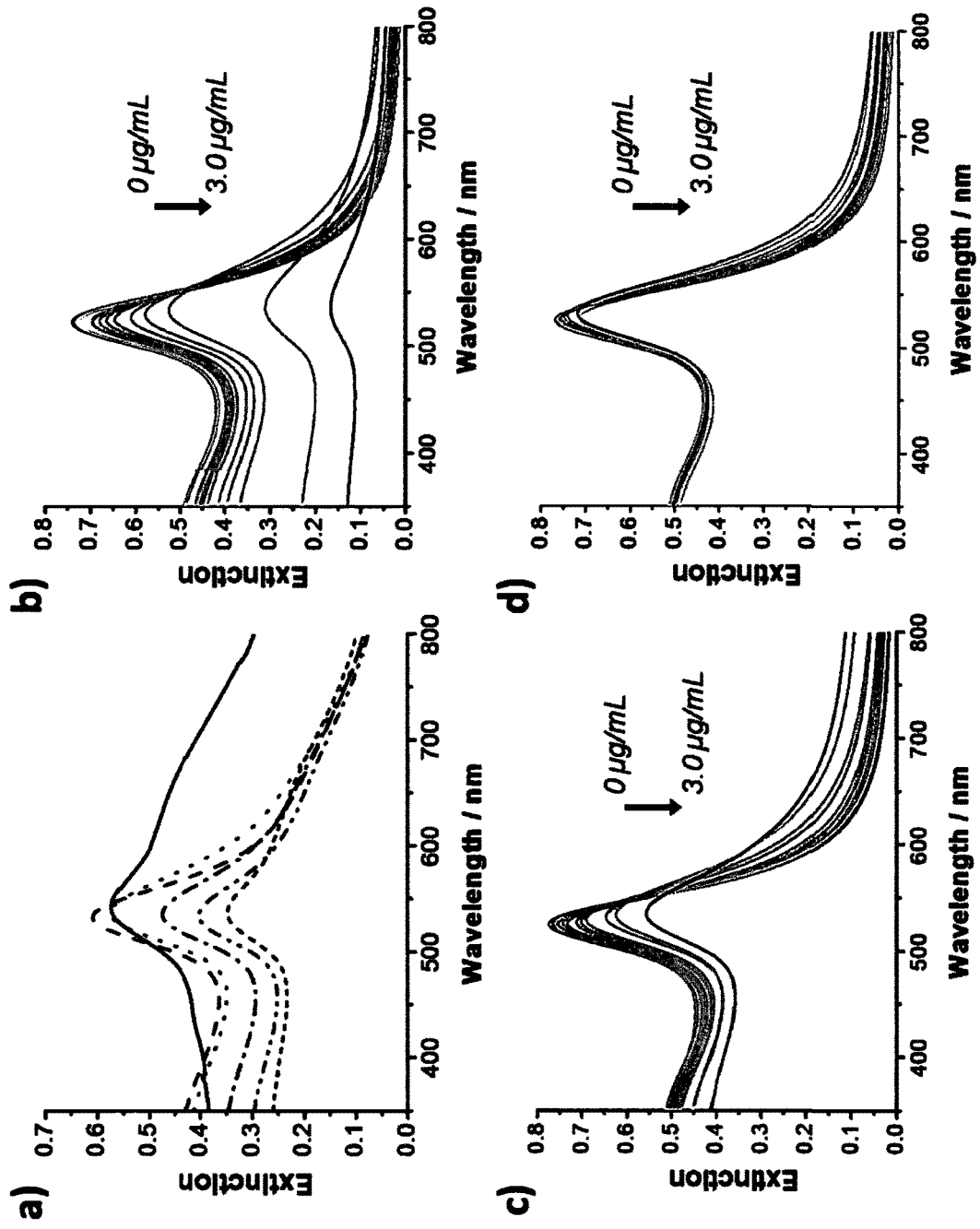

FIG. 2. a) UV-Vis extinction spectra of gold nanoparticles functionalised with citrate only (——) and with trivalent ligand 1:PEG ratio of: 2:98 (••••••) 5:95 (—•—), 10:90 (—••—), 25:75 (—) and 50:50 (---) measured 240 min after addition of influenza virus X31 (2.55 µg/mL). Variation of the UV-Vis extinction spectrum of gold nanoparticles functionalised with: b) trivalent ligand 1:PEG (25:75), c) monovalent ligand 3:PEG (25:75) and d) PEG, following addition of increasing concentrations of purified influenza virus X31 (from 0 (black) to 3.0 (dark grey) µg/mL); measurements were made 30 min following virus addition.

Figure 3:
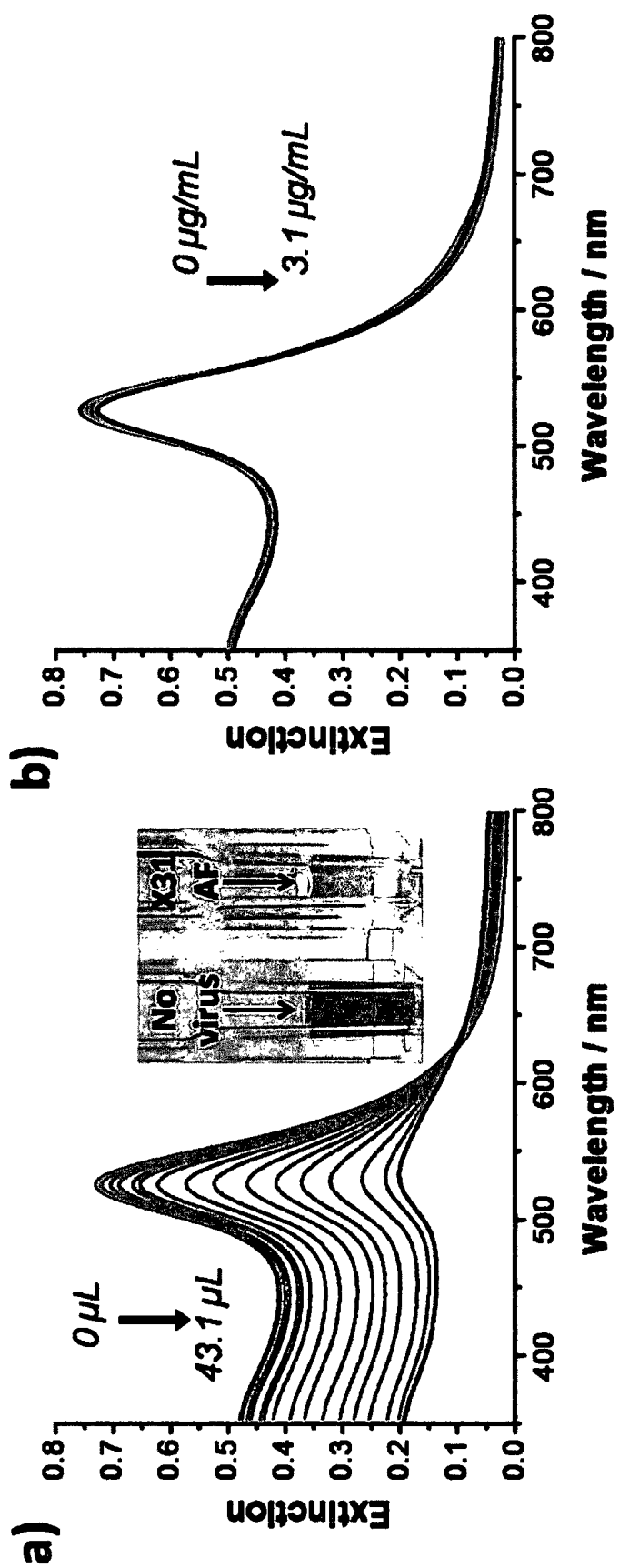

FIG. 3. UV-Vis spectra of: a) trivalent ligand 1:PEG (25:75) functionalised gold nanoparticles following addition of increasing volumes of influenza AF X31 (H3N2) (from 0 (black) to 43.1 (dark grey) µL), inset: cuvettes containing trivalent ligand 1:PEG (25:75) functionalised gold nanoparticles before (left) and following (right) addition of AF X31 (43.1 µL); and b) trivalent ligand 1:PEG (25:75) functionalised gold nanoparticles following addition of increasing concentrations of avian virus RG14 (H5N1) (from 0 (black) to 3.1 (dark grey) µg/mL).

Figure 4:
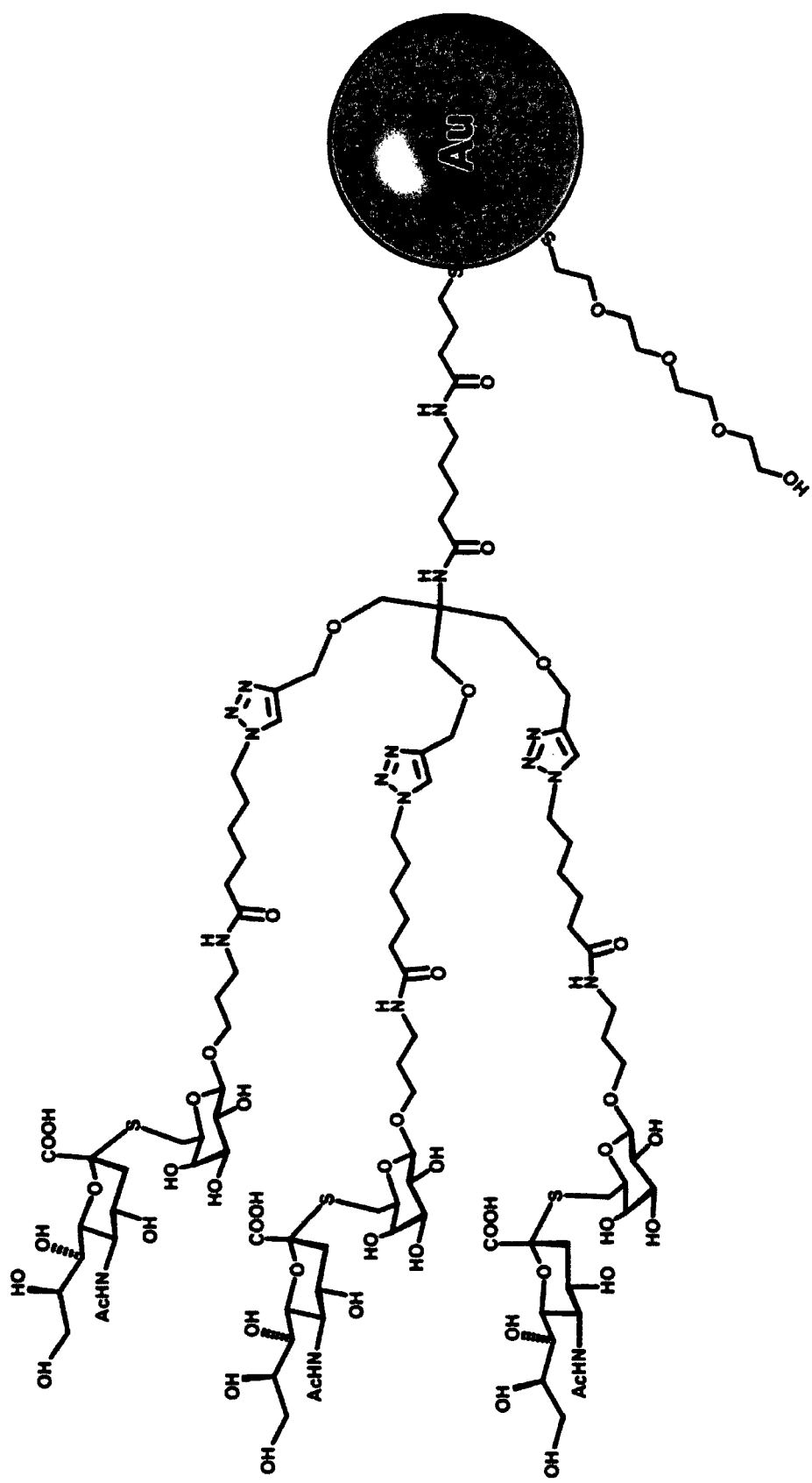

FIG. 4. Schematic representation of trivalent ligand 1:PEG functionalized gold nanoparticles: gold nanoparticles functionalized with trivalent ligand 1 and PEG ligand 2.

Figure 5:
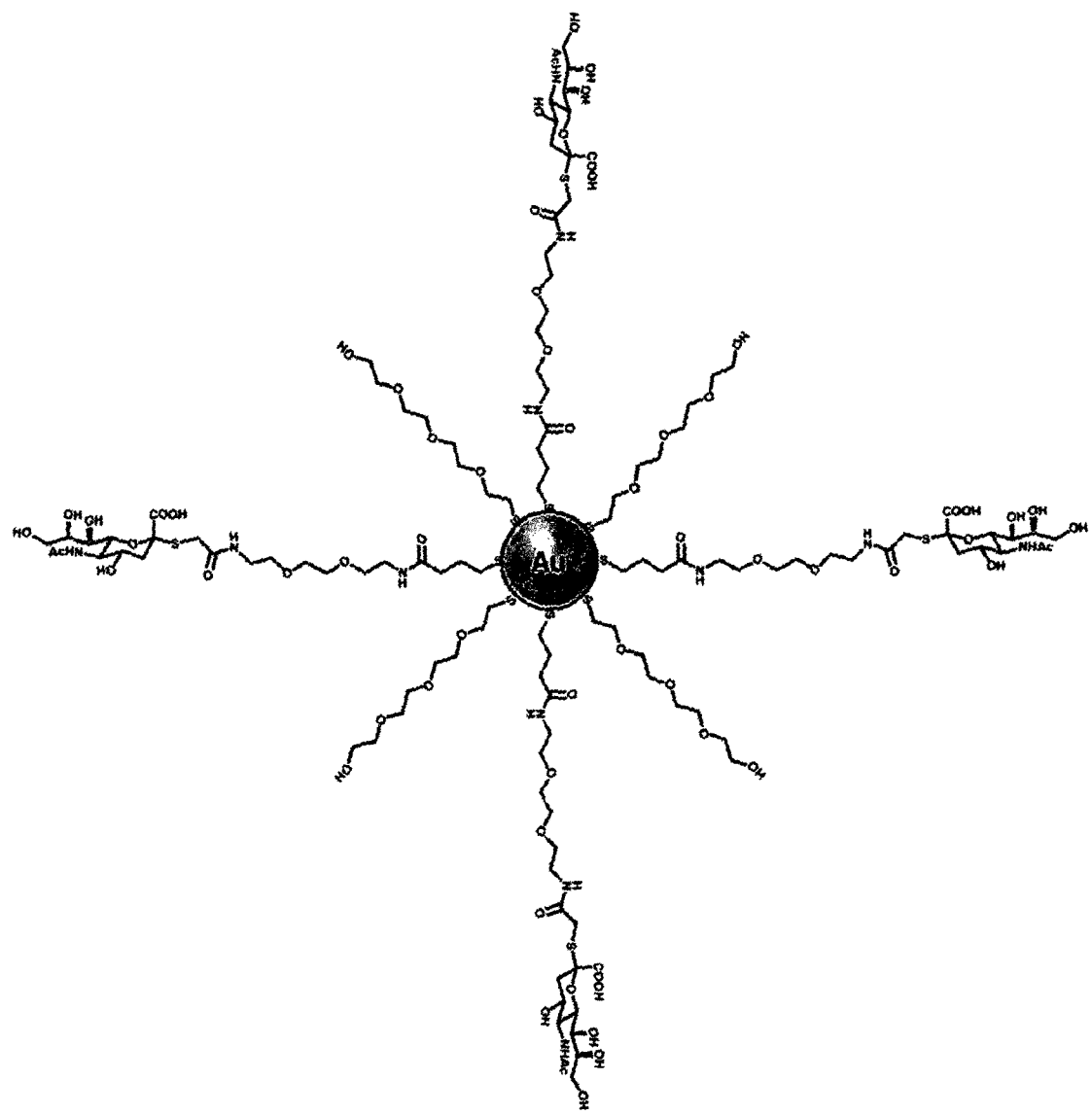

FIG. 5. Schematic representation of monovalent ligand 3:PEG functionalized gold nanoparticles: gold nanoparticles functionalized with monovalent ligand 3 and PEG ligand 2.

FIG. 6. a) Transmission electron micrograph (TEM) of a sample of trivalent ligand 1:PEG (50:50) functionalized gold nanoparticles (the scale bar represents 100 nm) and b) size distribution of the trivalent ligand 1:PEG (50:50) functionalized gold nanoparticles with a median value of 16.4±1.6 nm (n=116 nm)

Figure 7:
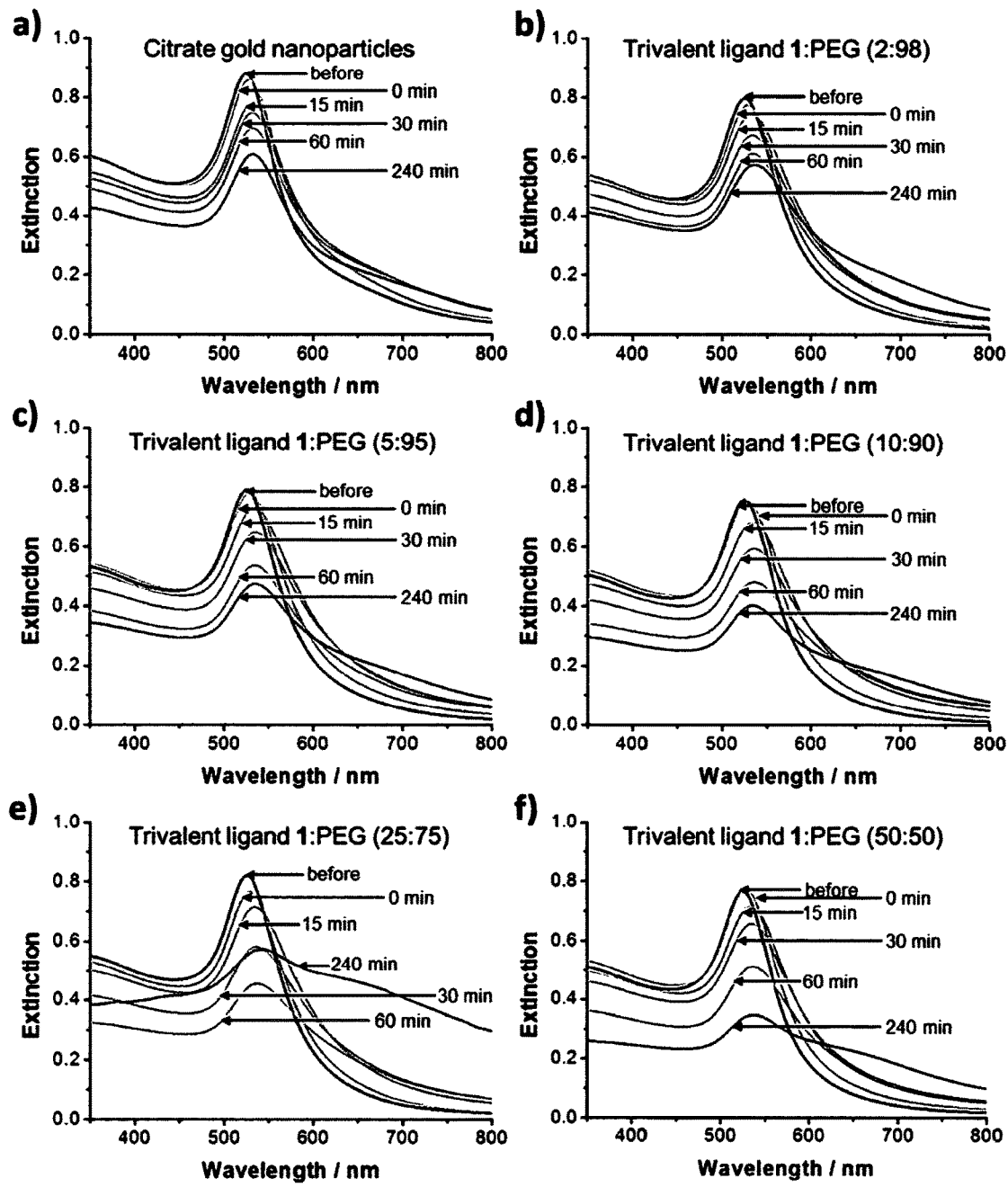

FIG. 7. Optimised trivalent ligand 1:PEG functionalisation ratio. UV-Vis spectra of different samples of functionalised gold nanoparticles before (black) and 0 min, 15 min, 30 min, 60 min and 240 min (dark grey) after addition of virus X31 (2.55 µg/mL). The different stabilised gold nanoparticles are: a) citrate coated gold nanoparticles and b)-f) trivalent ligand 1:PEG functionalised gold nanoparticles with trivalent ligand 1:PEG ratios: b) 2:98, c) 5:95, d) 10:90, e) 25:75 and f) 50:50.

Figure 8:
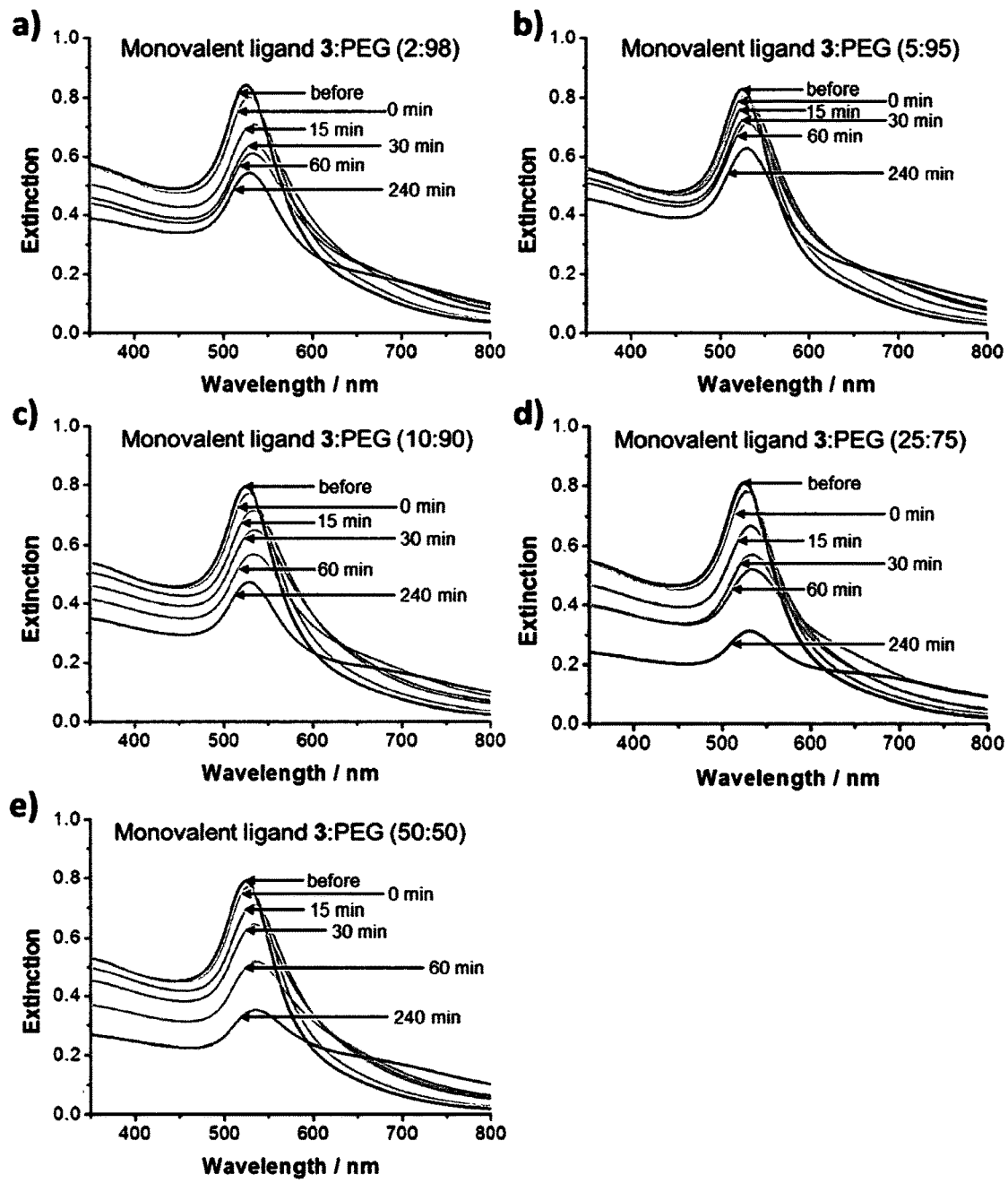

FIG. 8. Optimised monovalent ligand 3:PEG functionalisation ratio. UV-Vis spectra of different samples of functionalised gold nanoparticles before (black) and 0 min, 15 min, 30 min, 60 min and 240 min (dark grey) after addition of virus X31 (2.55 µg/mL). The different functionalised gold nanoparticles are monovalent ligand 3:PEG functionalised gold nanoparticles with monovalent ligand 3:PEG ratios: a) 2:98, b) 5:95, c) 10:90, d) 25:75 and e) 50:50.

FIG. 9. Comparison of trivalent ligand 1:PEG (25:75), monovalent ligand 3:PEG (25:75) and PEG functionalised gold nanoparticles. a) Extinction intensity at 525 nm of trivalent ligand 1:PEG (25:75) (▲), monovalent ligand 3:PEG (●) and PEG (■) functionalised gold nanoparticles with varying concentrations of virus X31; and b) cuvettes containing trivalent ligand 1:PEG (25:75) functionalised gold nanoparticles with different concentrations of virus X31. The extinction intensity was measured 30 min after addition of the virus.

Figure 10:
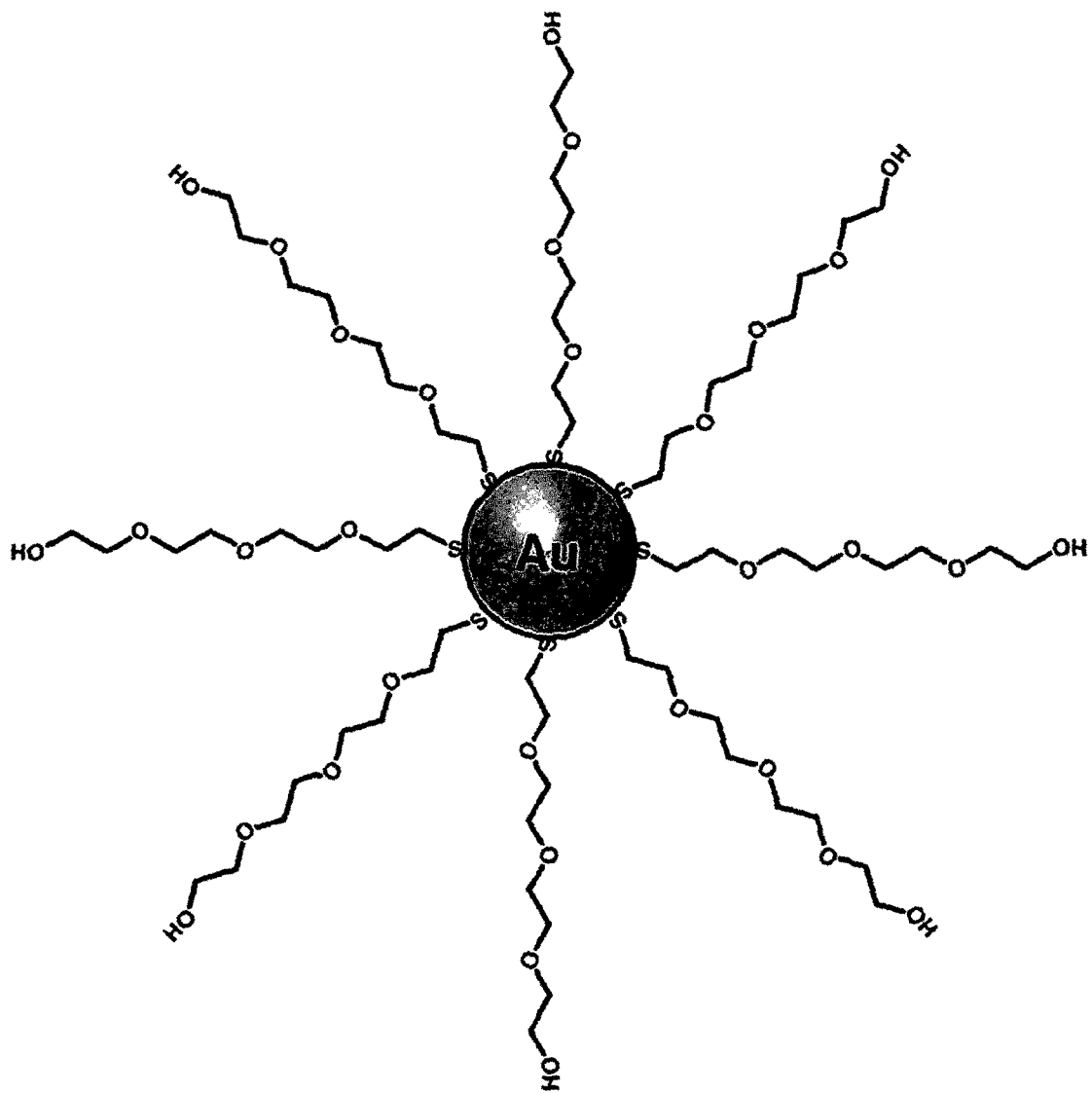

FIG. 10. Schematic representation of PEG functionalized gold nanoparticles: gold nanoparticles functionalized with PEG ligand 2.

Figure 11:
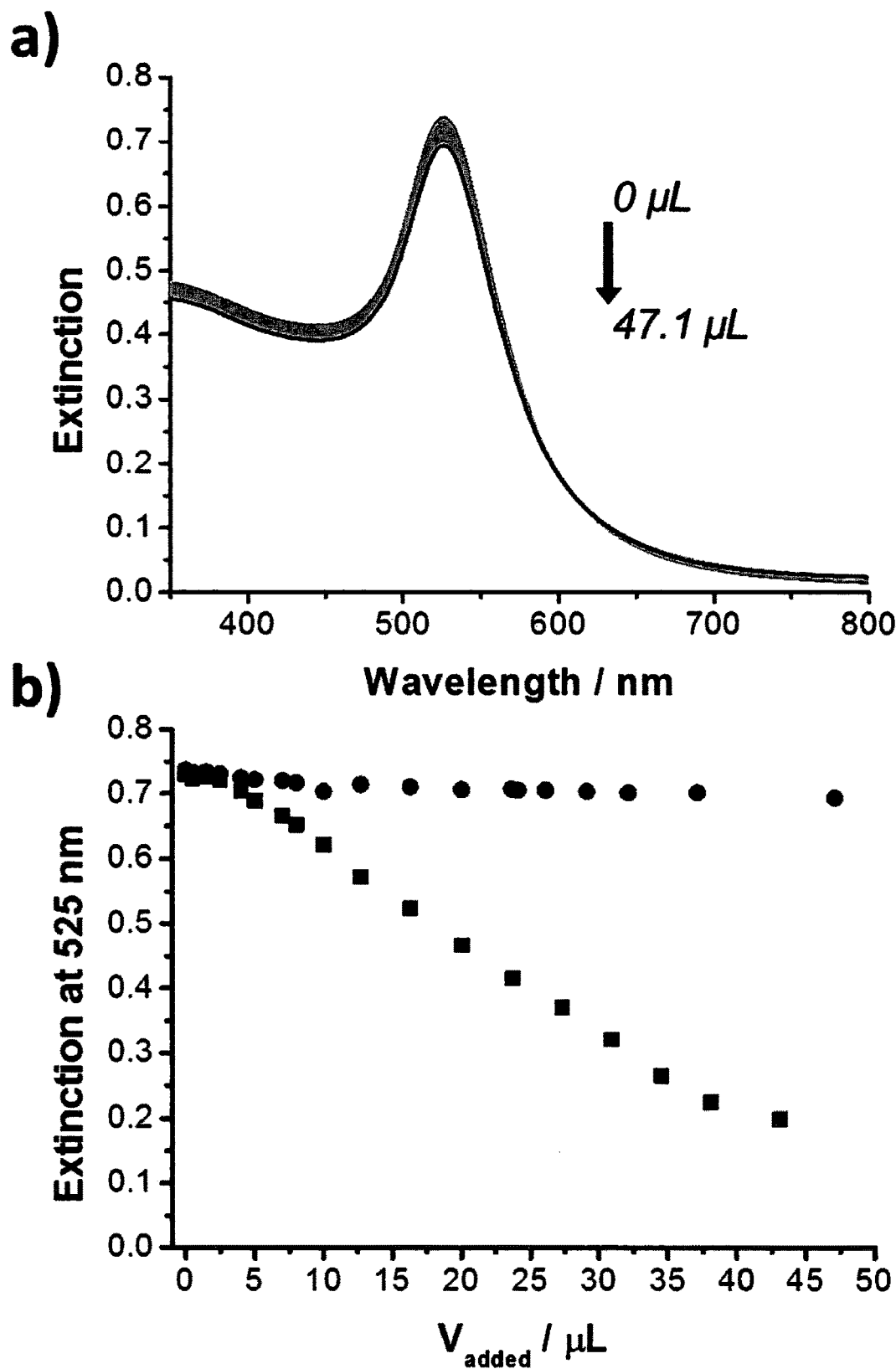

FIG. 11. Dilution effect control. a) Variation of the UV-Vis spectrum of trivalent ligand 1:PEG (25:75) functionalised gold nanoparticles with varying volumes (from 0 (black) to 47.1 (dark grey) μL) of Tris buffer and b) extinction intensity at 525 nm of trivalent ligand 1:PEG (25:75) functionalised gold nanoparticles with varying volumes of X31 virus from allantoic fluid (■) and with varying volumes of Tris buffer (●). The extinction intensity was measured 30 min after addition of the virus.

Figure 12:
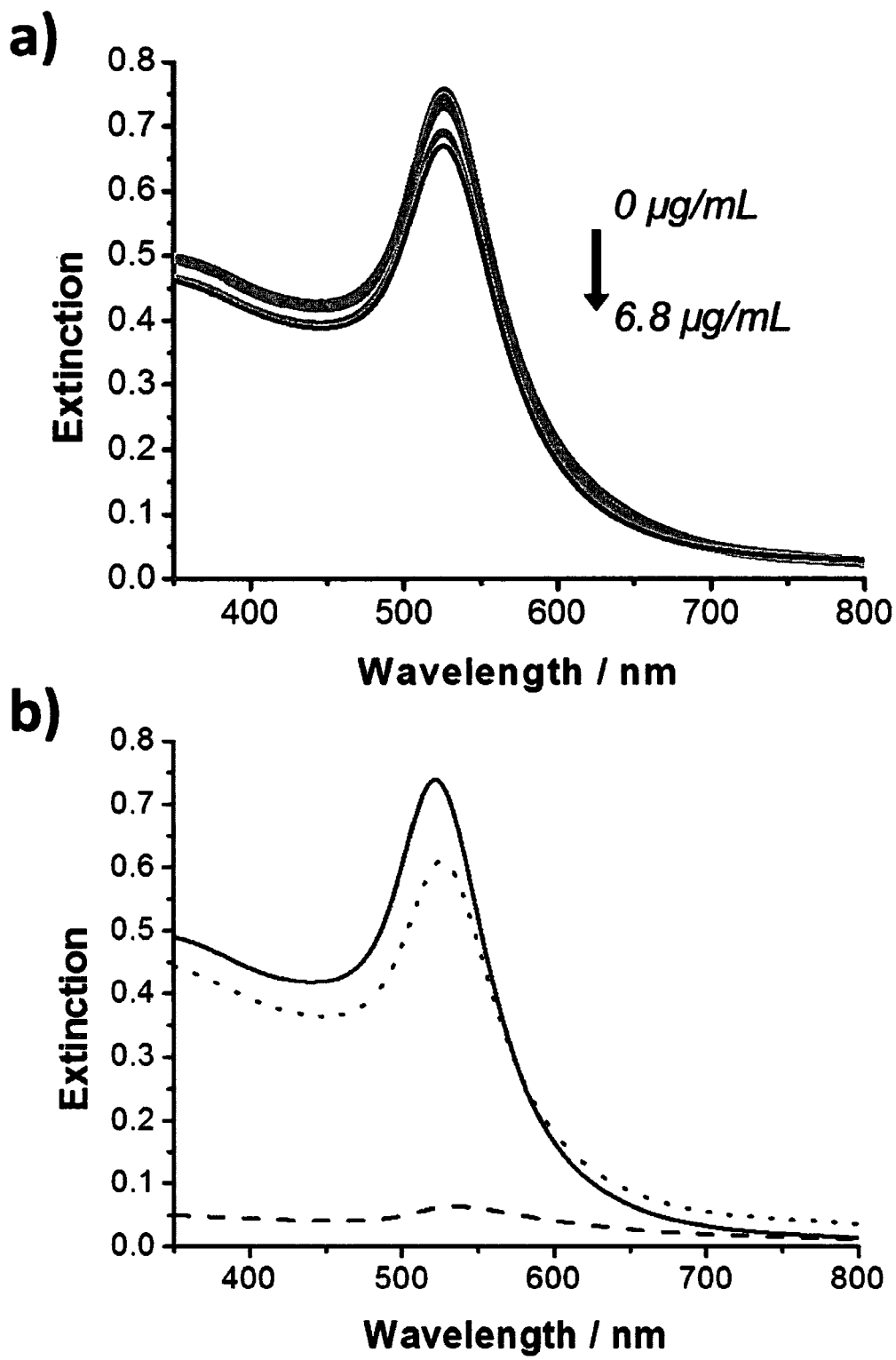

FIG. 12. UV-Vis spectra of: a) trivalent ligand 1:PEG (25:75) functionalised gold nanoparticles following addition of increasing concentrations (from 0 (black) to 6.8 (dark grey) μg/mL) of RG14 (H5N1) (the UV-Vis spectrum was measured 30 min after addition of each virus concentration); and b) trivalent ligand 1:PEG (25:75) functionalised gold nanoparticles before (—) and 6 days after addition of the avian RG14 (H5N1) (••••••) and human X31 (H3N2) (---) influenza viruses (6.8 μg/mL).

EXAMPLES

Example 1

Glyconanoparticles Presenting a Trivalent α2,6-Thio-Linked Sialic Acid can Detect Strains of Human Influenza within 30 Mins in a Simple Colorimetric Assay A schematic representation of the aggregation of the glyconanoparticles in the presence of the influenza virus is shown schematically in FIG. 1.

A comparison between gold nanoparticles functionalized with the trivalent ligand 1 and particles functionalized with a monovalent α-thio-linked sialic acid (monovalent ligand 3, FIG. 5) confirmed that the trivalent ligand 1 provided significantly superior results for the detection of the human influenza virus.

To show the utility of the trivalent ligand 1:PEG (25:75) functionalized gold nanoparticles for unpurified samples, the particles were used to detect the X31 virus from allantoic fluid (AF) at clinically relevant concentrations. Importantly, the α2,6-binding trivalent sialic acid glyconanoparticles were shown to specifically detect human rather than avian influenza virus.

Scheme 1. Synthesis of trivalent sialic acid derivative (trivalent ligand 1).

-continued

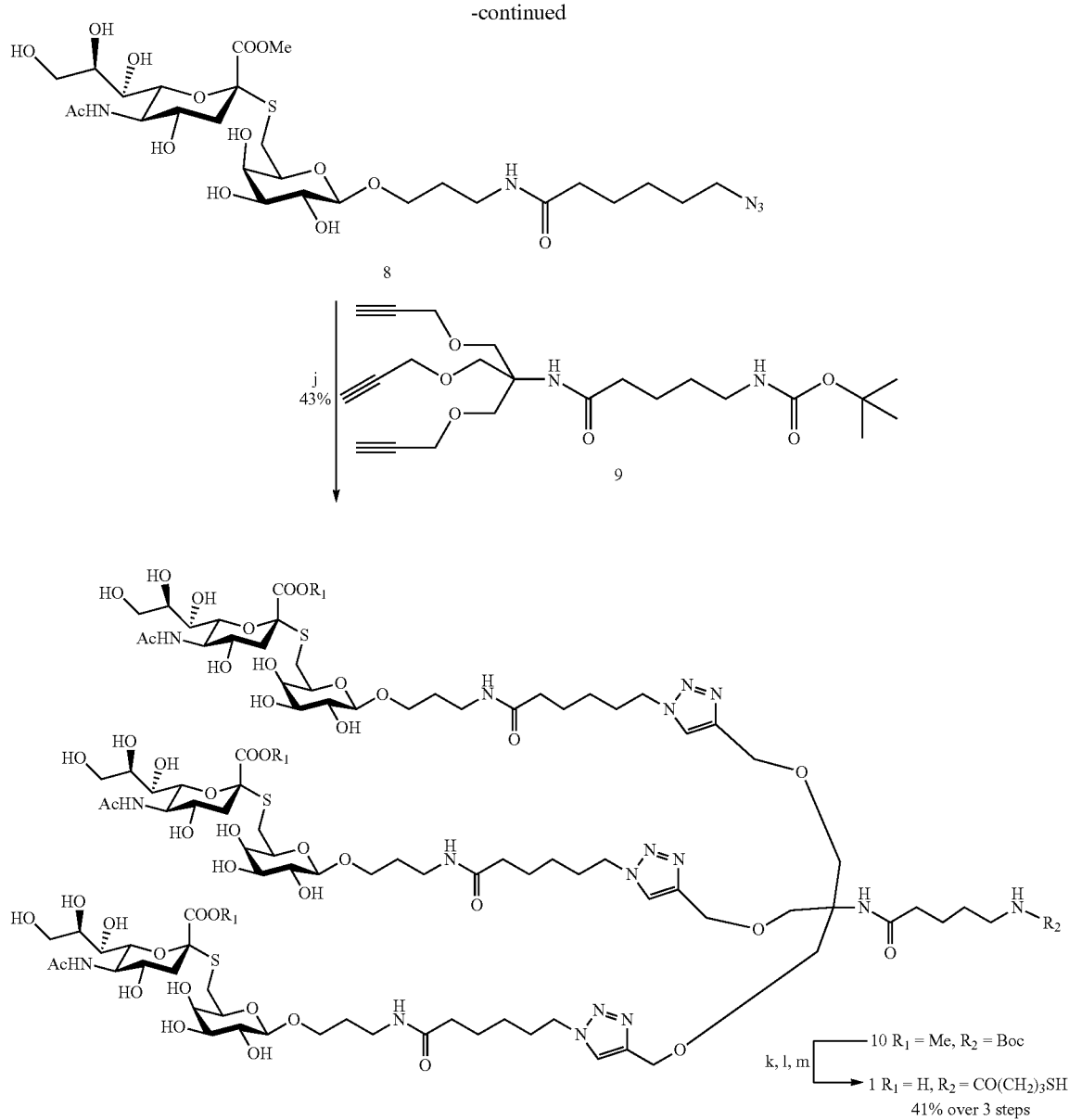

Reagents and conditions: a) 10% Pd—C, EtOAc; b) Azidohexanoic acid NHS ester, $Et_3N$, $CH_2Cl_2$; c) NaOMe—MeOH; d) TBDMS—Cl/DMF; e) $Ac_2O$/Pyr; f) 10% TFA in 80% aq. AcOH; g) $Tf_2O$/Pyr; h) $Et_2NH$/DMF; i) NaOMe/MeOH; j) $CuSO_4$—NaAsc—tBuOH/$H_2O$ 1:1; k) 1M aq. NaOH; l) 80% aq. TFA; and m) γ-thiobutyrolactone/DTT/0.5M aq. $NaHCO_3$/EtOH 1.5:1.

Analysis of the crystal structures of influenza virus HA suggests a distance of ca. 4 nm between the carbohydrate binding sites of the HA monomers within the HA trimer complex.[8, 16] To present 3 ligands to the 3 HA binding sites without introducing strain into the system, tether lengths of ca. 2-2.5 nm (22-25 bond lengths) between the sialic acid anomeric centre and the middle of the tripodal core are required. Based on these distance considerations, trivalent ligand 1 was synthesized as outlined in Scheme 1. To facilitate the later optimization of ligand presentation, a modular synthetic approach based on dipolar cycloaddition click chemistry[17] was devised that enabled modification of tether length, composition and rigidity. A related synthetic approach to divalent sialic acid has been previously reported by Kale et al.[18] Briefly, known azidopropyl galactoside 4 was reduced and acylated with known 6-azidohexanoic acid NHS ester.[19] Protecting groups were manipulated, via tert-butyldimethylsilyl (TBDMS) ether 5, to provide access to the unstable triflate 6, which reacted directly with known sialic acid thioacetate 7[20] in order to access a chemically and biologically stable thioglycoside.[21] The resulting α2,6-thio-linked sialic acid derivative 8 was subjected to $Cu^I$-catalysed 1,3-dipolar cycloaddition[17a, 22] with tripropargyl ether 9, which was prepared through standard transformation of known N-Boc-tri-O-propargyl-trishydroxymethyl-aminomethane.[23] Global deprotection of trivalent compound 10 and finally derivatization of the resulting primary amine with thiobutyrolactone gave the trivalent α2,6-thio-linked sialic acid (trivalent ligand 1) for immobilization on gold nanoparticles.

Scheme 2. Synthesis of monovalent ligand 3.

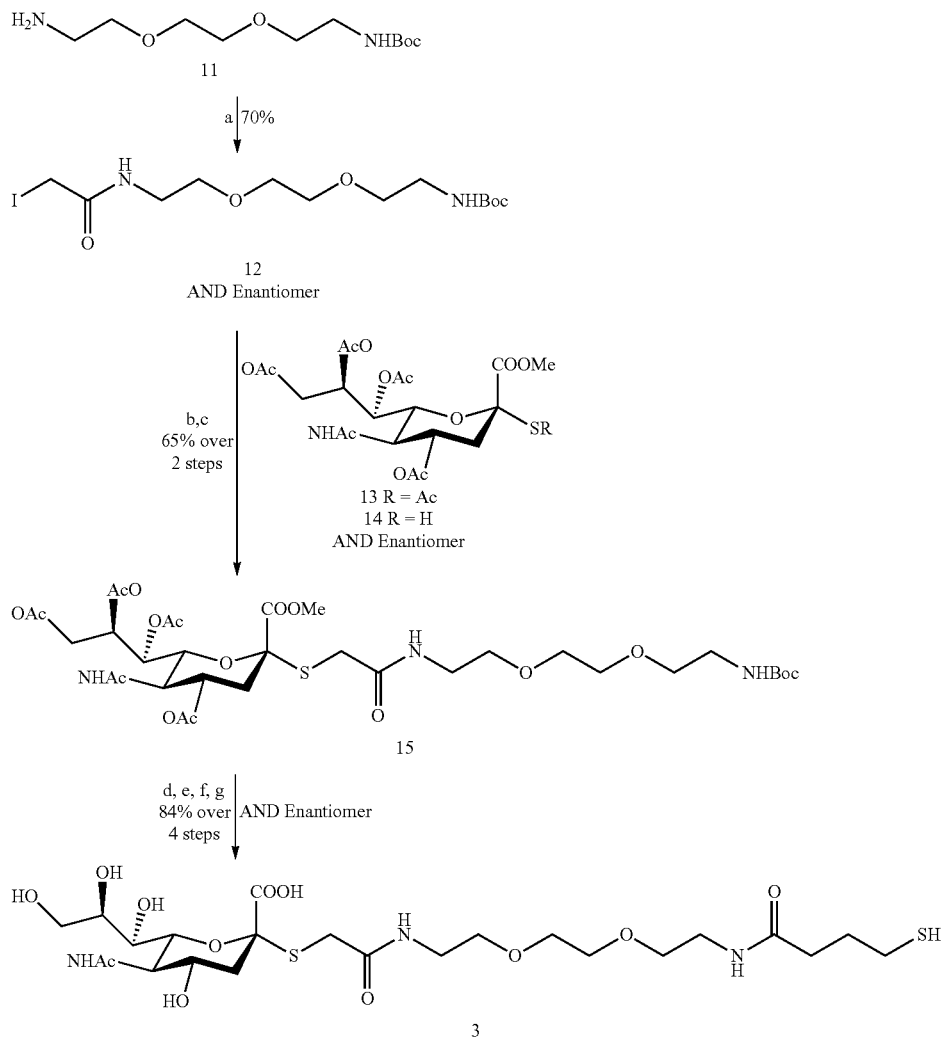

Reagents and conditions a) iodoacetic anhydride, Et₂O; b) 1. NaOMe/MeOH, -40° C. 2. Amberlite IR-120 (H⁺), -40° C.; c) 12, DIPEA, DCM; d) NaOMe/MeOH, r.t e) 1. 1M NaOH, r.t.; f) TFA, DCM, r.t g) γ-thiobutyrolactone, aq. NaHCO₃EtOH. DTT, 50° C.

The synthesis of the monovalent ligand 3 is detailed in Scheme 2. The aliphatic side chain of the alkyl thioglycoside of monovalent ligand 3 was synthesised starting from N-Boc-2,2'-(ethylenedioxy)bis(ethylamine) (11) prepared from the corresponding diamine following a published procedure.[25] The mono-N-Boc-protected diamine 11 was then reacted with iodoacetic anhydride to give the corresponding iodoacetamide 12 in 70% yield. Compound 12 was then used for the formation of the thioglycoside 15. The synthesis of monovalent ligand 3 started with the known α-thioacetate 13[26,27]. Subsequent chemoselective de-S-acetylation under low-temperature Zemplén conditions followed by low temperature quenching by acidic (H⁺) resin generated α-configured Neu5Ac thiol 14,[27,28] which was used directly in the next step. Alkylation of the thiol 14 with iodoacetamide 12 in dichloromethane in the presence of Hunig's base[29] gave thioglycoside 15 in 65% yield over two steps. Global deprotection[29] and subsequent reaction of the free amine with γ-thiobutyrolactone in a buffered (pH~9.0) ethanolic solution[30] afforded the sodium salt of 3, which upon acidification gave the desired alkyl monovalent ligand 3 in 84% yield over 4 steps. Starting from sialic acid, the desired monovalent ligand 3, was prepared in 10 synthetic steps with a 34% overall yield.

The synthesis of the gold nanoparticles (ca. 16 nm diameter) was achieved using citrate as both the reducing agent and the stabilizer of the gold core.[24] Citrate-reduced gold nanoparticles were functionalized with a mixed monolayer (FIG. 4) consisting of the thiolated trivalent α2,6-linked sialic acid (trivalent ligand 1) and a thiolated polyethylene glycol derivative (PEG ligand 2).

To establish whether the binding of the influenza virus to the trivalent ligand 1 on the surface of the gold nanoparticles was affected by ligand density, varying ratios of the trivalent ligand 1:PEG (50:50, 25:75, 10:90, 5:95 and 2:98) were used to functionalize the particles. TEM images of the functionalized gold nanoparticles showed disperse nanoparticles with an average size of 16.4±1.6 nm (FIG. 6). The nanoparticle solutions, with varying ligand density, were all deep red in color and exhibited a surface plasmon absorption band at ca. 525 nm. The surface plasmon absorption band was red-shifted by ca. 5 nm, as compared to that observed for the citrate-coated nanoparticles, due to the assembly of the monolayer on the gold surface. Human influenza virus X31 (2.55 µg/mL) was added to the various trivalent ligand 1:PEG functionalized gold nanoparticles. Citrate coated gold nanoparticles were used as a control. The UV-Vis extinction spectrum of each sample was measured before and 0, 15, 30, 60 and 240 min after addition of the virus (FIG. 7). The greatest change in the surface plasmon absorption band was observed when the nanoparticles functionalized with trivalent ligand 1:PEG of a ratio 25:75 interacted with the human influenza virus X31 for 240 min (FIG. 2a). The UV-Vis spectrum in FIG. 2a highlights the broadening of the surface plasmon absorption band of the 25:75 ratio trivalent ligand 1:PEG gold nanoparticles indicating significant interaction with the influenza virus. The same experiment was performed using gold nanoparticles functionalized with different ratios of monovalent ligand 3:PEG ligand 2 (50:50, 25:75, 10:90, 5:95 and 2:98). The results obtained suggest that a 25:75 ratio of the monovalent ligand 3:PEG was also the optimum ligand density (FIG. 8).

The optimized glyconanoparticles were used to colorimetrically detect increasing concentrations of the X31 influenza virus. As shown in FIG. 2b, upon addition of the human influenza virus X31 the surface plasmon absorption band red-shifted (from 525 to 536 nm) and decreased in intensity with increasing concentration of the virus (FIG. 2b and FIG. 9a). The results suggest that the influenza virus induces aggregation of the glyconanoparticles as schematically shown in FIG. 1. The aggregation of the optimized glyconanoparticles was spectroscopically measured 30 min following addition of increasing virus concentration. Changes of the surface plasmon absorption band due to the addition of the virus led to changes of solution color, from the initial deep red to lighter red (FIG. 9b). A comparison of the binding affinity of the trivalent ligand 1:PEG (25:75) and monovalent ligand 3:PEG (25:75) functionalized gold nanoparticles towards human influenza virus X31 was made. The addition of human influenza virus X31 to a solution of the monovalent ligand 3:PEG (25:75) functionalized gold nanoparticles produced a small decrease and red-shift (from 525 to 534 nm) of the surface plasmon absorption band intensity with an increase in the extinction at ca. 620 nm (FIG. 2c and FIG. 9a). These results indicate the initiation of the aggregation of the nanoparticles. However, a significantly greater concentration of virus was required when the monovalent ligand 3 was used to produce the same change of the extinction spectrum as that observed with the trivalent ligand 1:PEG functionalized gold nanoparticles. The control experiment of gold nanoparticles functionalized only with PEG ligand 2 (FIG. 10) induced negligible changes of the extinction spectrum following addition of increasing concentrations of the influenza virus X31 (FIG. 2d and FIG. 9a). These results highlight the increased affinity of the trivalent sialic acid ligand 1:PEG glyconanoparticles towards the human influenza virus X31 as compared to the monovalent sialic acid ligand 3:PEG functionalized particles. Further, the control experiments show that the presence of a sialic acid derivative is essential to bind the glyconanoparticles to the virus via HA binding sites to facilitate colorimetric detection of the virus.

To mimic clinical samples of unknown concentration and purity, colorimetric detection of the human influenza virus X31 from influenza allantoic fluid (AF) was achieved using the trivalent ligand 1:PEG (25:75) functionalized gold nanoparticles. The addition of increasing volumes of X31 influenza AF to a sample of the functionalized gold nanoparticles induced the aggregation of the optimised glyconanoparticles. Upon increasing volume of the X31 influenza AF, a decrease in the extinction intensity of the surface plasmon absorption band at ca. 525 nm with a consequent solution color change from deep red to colorless was observed (FIG. 3a). A control experiment, with increasing volumes of Tris buffer added to the trivalent ligand 1:PEG (25:75) functionalized gold nanoparticles, confirmed that the changes observed were due to the presence of the X31 AF and not to a dilution effect (FIG. 11).

The primary intention of synthesising the α2,6-configured trivalent sialic acid functionalized gold nanoparticles was to create sensors that would discriminate between human and avian influenza virus. Trivalent ligand 1 was synthesised containing three α2,6-thio-linked sialic acids. Human influenza virus binds preferentially to α2,6 residues while avian influenza virus binds to α2,3 residues.[14] Consequently, the optimized glyconanoparticles should not aggregate in the presence of avian influenza virus. A reassortant influenza virus, RG14 with HA and NA genes from an avian virus A/Vietnam/1194/2004 (H5N1), was added at increasing concentrations (from 0 to 3.1 µg/mL) to a solution of trivalent ligand 1:PEG (25:75) functionalized gold nanoparticles. Changes in the surface plasmon absorption band were monitored 30 min after addition of the virus. As shown in FIG. 3b, no changes in the surface plasmon absorption band of the functionalized gold nanoparticles were observed after addition of 3.1 µg/mL of the avian virus RG14. With a similar concentration of human influenza virus X31, the spectroscopic characteristics of the surface plasmon absorption band of the functionalized gold nanoparticles substantially changed following binding and aggregation of the glyconanoparticles (FIG. 2b). To further demonstrate that the synthesized glyconanoparticles bind specifically to human influenza, the concentration of avian influenza RG14 was increased to 6.8 µg/mL in a solution of functionalized gold nanoparticles. Negligible changes of the surface plasmon absorption band of the particles were observed (FIG. 12a). The avian virus was incubated with the nanoparticles for a period of 6 days, after which the UV-Vis extinction spectrum of the particles was measured. Only a small decrease in the extinction intensity was observed (FIG. 12b—see dotted line [••••••]) as compared to the change of the surface plasmon absorption band caused by the presence of the same concentration, and same incubation time, of human influenza virus X31 (FIG. 12b—see dashed line [---]). From these results it is apparent that the designed trivalent ligand 1:PEG (25:75) functionalized gold nanoparticles can readily distinguish between human and avian influenza virus strains.

In summary, we have achieved the synthesis of a thiolated trivalent α2,6-thio-linked sialic acid derivative to functionalize gold nanoparticles. The optimised glyconanoparticles consist of the thiolated trivalent α2,6-thio-linked sialic acid derivative and a thiolated PEG derivative self-assembled onto the gold surface in a 25:75 ratio. These glyconanoparticles were used for the plasmonic detection of influenza virus. The trivalent ligand 1:PEG (25:75) functionalized gold nanoparticles were used to detect the human influenza virus X31 (H3N2) within 30 min. Non-purified, influenza virus in allantoic fluid was successfully detected by the functionalized nanoparticles. A comparison between the trivalent and a monovalent α2,6-thio-linked sialic acid functionalized nanoparticles confirmed that more rapid results, with greater sensitivity, were achieved using the trivalent ligand for the detection of the X31 virus. Importantly, the trivalent ligand 1:PEG (25:75) functionalized gold nanoparticles were able to discriminate between human (α2,6 binding) and avian (α2,3 binding) influenza. Since the dominant strain of human influenza varies seasonally, and with the possible threat of influenza virus crossing between animal species and thereby potentially initiating a pandemic, the ability to distinguish between human and avian influenza virus strains is exceptionally important. The synthesis of a trivalent α2,6-thio-linked sialic acid derivative to functionalize gold nanoparticles provides an innovative bioassay for the specific recognition and detection of influenza virus strains in clinical samples.

References for Description and Example 1

[1] World Health Organisation—Fact sheet No 211 (2009) Influenza. http://www.who.int/mediacentre/en/.
[2] S. J. Gamblin, J. J. Skehel, *J. Biol. Chem.* 2010, 285, 28403-28409.
[3] a) S. G. Muthuri, P. R. Myles, S. Venkatesan, J. Leonardi-Bee, J. S. Nguyen-Van-Tam, *J. Infect. Dis.* 2013, 207, 553-563; b) WHO Global Influenza Surveillance Network, *Manual for the laboratory diagnosis and virological surveillance of influenza*, WHO Press, World Health Organization, Geneva, 2011.
[4] C. A. Mirkin, R. L. Letsinger, R. C. Mucic, J. J. Storhoff, *Nature* 1996, 382, 607-609.
[5] K. Saha, S. S. Agasti, C. Kim, X. Li, V. M. Rotello, *Chem. Rev.* 2012, 112, 2739-2779.
[6] M. Marradi, F. Chiodo, I. Garcia, S. Penadés, *Chem. Soc. Rev.* 2013, 42, 4728-4745.
[7] a) D. C. Hone, A. H. Haines, D. A. Russell, *Langmuir* 2003, 19, 7141-7144; b) C. L. Schofield, A. H. Haines, R. A. Field, D. A. Russell, *Langmuir* 2006, 22, 6707-6711; c) C. L. Schofield, B. Mukhopadhyay, S. M. Hardy, M. B. McDonnell, R. A. Field, D. A. Russell, *Analyst* 2008, 133, 626-634; d) A. J. Reynolds, A. H. Haines, D. A. Russell, *Langmuir* 2006, 22, 1156-1163; e) C. L. Schofield, R. A. Field, D. A. Russell, *Anal. Chem.* 2007, 79, 1356-1361.
[8] I. Papp, C. Sieben, K. Ludwig, M. Roskamp, C. Bottcher, S. Schlecht, A. Herrmann, R. Haag, *Small* 2010, 6, 2900-2906.
[9] M. Stanley, N. Cattle, J. McCauley, S. R. Martin, A. Rashid, R. A. Field, B. Carbain, H. Streicher, *Med Chem Comm* 2012, 3, 1373-1376.
[10] M. Sametband, S. Shukla, T. Meningher, S. Hirsh, E. Mendelson, R. Sarid, A. Gedanken, M. Mandelboim, *Med Chem Comm* 2011, 2, 421-423.
[11] K. V. Chakravarthy, A. C. Bonoiu, W. G. Davis, P. Ranjan, H. Ding, R. Hu, J. B. Bowzard, E. J. Bergey, J. M. Katz, P. R. Knight, S. Sambhara, P. N. Prasad, *Proc. Natl. Acad. Sci.* 2010, 107, 10172-10177.
[12] J. D. Driskell, C. A. Jones, S. M. Tompkins, R. A. Tripp, *Analyst* 2011, 136, 3083-3090.
[13] C. Lee, M. A. Gaston, A. A. Weiss, P. Zhang, *Biosens. Bioelectron.* 2013, 42, 236-241
[14] a) G. N. Rogers, B. L. D'Souza, *Virology* 1989, 173, 317-322; b) R. J. Connor, Y. Kawaoka, R. G. Webster, J. C. Paulson, *Virology* 1994, 205, 17-23.
[15] J. J. Skehel, D. C. Wiley, *Annu. Rev. Biochem.* 2000, 69, 531-569.
[16] Y. P. Lin, X. Xiong, S. A. Wharton, S. R. Martin, P. J. Coombs, S. G. Vachieri, E. Christodoulou, P. A. Walker, J. Liu, J. J. Skehel, S. J. Gamblin, A. J. Hay, R. S. Daniels, J. W. McCauley, *Proc. Natl. Acad. Sci.* 2012, 109, 21474-21479.
[17] a) M. Meldal, C. W. Tornøe, *Chem. Rev.* 2008, 108, 2952-3015; b) V. Aragão-Leoneti, V. L. Campo, A. S. Gomes, R. A. Field, I. Carvalho, *Tetrahedron* 2010, 66, 9475-9492.
[18] R. R. Kale, H. Mukundan, D. N. Price, J. F. Harris, D. M. Lewallen, B. I. Swanson, J. G. Schmidt, S. S. Iyer, *J. Am. Chem. Soc.* 2008, 130, 8169-8171.
[19] C. Grandjean, A. Boutonnier, C. Guerreiro, J.-M. Fournier, L. A. Mulard, *J. Org. Chem.* 2005, 70, 7123-7132.
[20] A. Hasegawa, J. Nakamura, M. Kiso, *J. Carbohydr. Chem.* 1986, 5, 11-19.
[21] H. Driguez, J. Thiem, in *Glycoscience Synthesis of Oligosaccharides and Glycoconjugates, Vol.* 186 (Eds.: H. Driguez, J. Thiem), 1997, pp. 85-116.
[22] a) C. W. Tornøe, C. Christensen, M. Meldal, *J. Org. Chem.* 2002, 67, 3057-3064; b) H. C. Kolb, M. G. Finn, K. B. Sharpless, *Angew. Chem., Int. Ed.* 2001, 40, 2004-2021.
[23] Y. M. Chabre, C. Contino-Pépin, V. Placide, T. C. Shiao, R. Roy, *J. Org. Chem.* 2008, 73, 5602-5605.
[24] B. V. Enüstün, J. Turkevich, *J. Am. Chem. Soc.* 1963, 85, 3317-3328.
[25] S. M. Khersonsky, D. W. Jung, T. W. Kang, D. P. Walsh, H. S. Moon, H. Jo, E. M. Jacobson, V. Shetty, T. A. Neubert, Y. T. Chang, *J. Am. Chem. Soc.* 2003, 125, 11804-11805.
[26] R. Kuhn, P. Lutz, D. L. MacDonald, *Chem. Ber.* 1966, 99, 611-&.
[27] A. Hasegawa, J. Nakamura, M. Kiso, *J. Carbohydr. Chem.* 1986, 5, 11-19.
[28] Z. H. Gan, R. Roy, Can. *J. Chem.* 2002, 80, 908-916.
[29] S. Park, M. R. Lee, S. J. Pyo, I. Shin, *J. Am. Chem. Soc.* 2004, 126, 4812-4819.
[30] O. Blixt, T. Norberg, *J. Org. Chem.* 1998, 63, 2705-2710.
[31] J.-M. Beau, B. Vauzeilles, T. Skrydstrup., *Glycoscience: Chemistry and Chemical Biology, Vol.* 3, (Eds.: B. O. Fraiser-Reid, K. Tatsuta, J. Thiem), 2001, 2679.
[32] M. Sodeoka, G. Hirai, T. Watanabe, T. Miyagi, *Pure App. Chem.,* 2009, 81, 205-215.
[33] M. Vonitzstein, W. Y. Wu, G. B. Kock, M. S. Pegg, J. C. Dyason, B. Jin, T. V. Phan, M. L. Smythe, H. F. White, S. W. Oliver, P. M. Colman, J. N. Varghese, D. M. Ryan, J. M. Woods, R. C. Bethell, V. J. Hotham, J. M. Cameron C. R. Penn, *Nature,* 1993, 363, 418-423.
[34] M. Stanley, S. R. Martin, M. Birge, B. Carbain, H. Streicher *Organic and Biomolecular Chemistry,* 2011, 9, 5625-5629.

Example 2

Synthesis of Trivalent Ligand 1, PEG Ligand 2 and Monovalent Ligand 3

Synthesis of Trivalent Ligland 1, PEG Ligland 2 and Monovalent Ligland 3

General Methods

Commercial reagents were obtained from Acros, Aldrich, Alfa Aesar and Fluka and used without further purification. N-Boc aminopentanoic acid (valeric acid) was purchased from Sigma Aldrich. TLC was performed on precoated silica plates (Merck 60 F254, 0.25 mm) containing a fluorescence indicator. Compounds were visualised under UV (254 nm) and by heating after dipping the TLC plate in a solution of 5% $H_2SO_4$ in ethanol, in a solution of ninhydrin (200 mg) in butanol (95 mL) and acetic acid (10%, 5 mL) or in 15% aqueous sulfuric acid saturated with cerium(IV) sulfate. Gel chromatography was performed on TSK HW4OS gel using a XK16/40 column. Flash column chromatography was performed on silica gel (Biotage KP-SIL 60A, 40-63 µm). Standard column chromatography was performed on silica gel (Fluka 60, 63-200 µm). NMR spectra were recorded on a Bruker spectrometer: $^1$H NMR spectra recorded at 400 MHz were referenced to $\delta_H$ 7.26 for CDCl$_3$ or $\delta_H$ 3.34 for CD$_3$OD; $^{13}$C NMR spectra recorded at 100 MHz were referenced to $\delta_C$ 77.0 for CDCl$_3$ or $\delta_C$ 49.05 for CD$_3$OD. Chemical shifts of NMR signals recorded in D$_2$O are reported with respect to the methyl resonance of internal acetone at $\delta_H$ 2.22 ppm and $\delta_C$ 30.89 ppm, respectively. Assignments were made with the aid of COSY and HSQC experiments. Multiplicity of signals in $^{13}$C NMR spectra was determined from HSQC spectra.

Synthesis of 3-Aminopropyl 2,3,4,6-tetra-O-acetyl-β-D-galactopyranoside

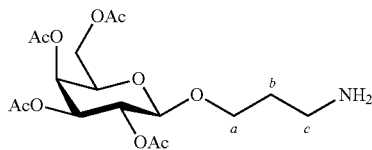

3-Azidopropyl 2,3,4,6-tetra-O-acetyl-β-D-galactopyranoside 4[1] (6.5 g, 15.1 mmol) and 10% Pd—C (200 mg) in ethyl acetate (EtOAc, 50 mL) were stirred under an atmosphere of hydrogen for 6 h, at which point TLC showed a complete conversion to a slower moving product ($R_f$=0.1, dichloromethane/methanol 3:1). The catalyst was removed by filtration of the suspension through a plug of Celite, which was washed with ethyl acetate and the combined filtrate was concentrated in vacuo to yield a colorless oil. The residue was subjected to column chromatography on silica gel (dichloromethane/methanol, stepwise gradient 10:1, 5:1) to give the corresponding aminopropyl glycoside (5.8 g, 95%). $^1$H NMR (CDCl$_3$): δ=6.04 (bt, 1H, NH), 5.41 (dd, 1H, H4, $^3J_{3,4}$=3.4 Hz, $^3J_{4,5}$=1.1 Hz), 5.20 (dd, 1H, H2, $^3J_{1,2}$=7.9 Hz, $^3J_{2,3}$=10.4 Hz), 5.04 (dd, 1H, H3, $^3J_{2,3}$=10.4 Hz, $^3J_{3,4}$=3.4 Hz), 4.45 (d, 1H, H1, $^3J_{1,2}$=7.9 Hz), 4.08-4.22 (m, 2H, H6), 4.00 (m, 1H, Ha), 3.92 (m, 1H, H5, $^3J_{4,5}$=1.1 Hz, $^3J_{5,6}$=6.6 Hz), 3.58 (m, 1H, Ha), 3.47-3.38 (m, 1H, Hc), 3.34-3.20 (m, 1H, Hc), 2.17, 2.08, 2.06, 1.99 (4s, 12H, CH$_3$CO), 1.92-1.72 (m, 2H, Hb); $^{13}$C NMR (CDCl$_3$) from HSQC: δ=102.2 (d, 1C, H1), 70.9, (d, 1C, C5), 70.6 (d, 1C, C3), 69.2 (t, 1C, Ca), 68.8 (d, 1C, C2), 66.9 (d, 1C, C4), 61.2 (t, 1C, C6), 37.7 (t, 1C, Cc), 29.1 (t, 1C, Cb), 20.7 (4×q, 3C, 4×CH$_3$CO—); m/z (MALDI$^+$) 405.90 [M+H]$^+$; HR-MS calcd for C$_{17}$H$_{28}$NO$_{10}$$^+$ [M+H]$^+$ 406.1708, found 406.1707.

Synthesis of 3-(N-Azidopentyloxycarbonyl)aminopropyl 2,3,4,6-tetra-O-acetyl-β-D-galactopyranoside

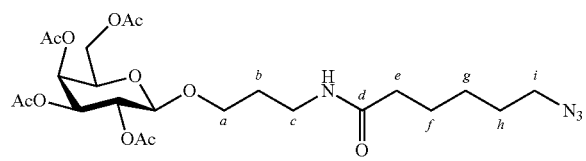

To a solution of 3-Aminopropyl 2,3,4,6-tetra-O-acetyl-β-D-galactopyranoside (5.5 g, 13.5 mmol) and 6-azidohexanoic acid NHS ester[2] (3.4 g, 13.5 mmol) in dry dichloromethane (CH$_2$Cl$_2$, 50 mL) was added triethylamine (Et$_3$N, 4.1 mL, 30 mmol) and the reaction mixture was stirred at room temperature for 3 h, at which point TLC showed the reaction to be complete (product $R_f$=0.6, ethyl acetate). The solvent was removed in vacuo and the resulting residue was purified by silica column chromatography (stepwise gradient, ethyl acetate/hexane 50:50, 100:0) to give the corresponding amide as a syrup (5.0 g, 68%). $^1$H NMR (CDCl$_3$): δ=5.94 (s, 1H, 5.41 (d, $J_{3,4}$=3.5 Hz, 1H, H-4), 5.20 (dd, $J_{1,2}$=8.0 Hz, $J_{2,3}$=10.5 Hz, 1H, H-2), 5.04 (dd, $J_{2,3}$=10.5 Hz, $J_{3,4}$=3.5 Hz, 1H, H-3), 4.45 (d, $J_{1,2}$=8.0 Hz, 1H, H-1), 4.16 (m, 2H, H6a, H6b), 4.00 (m, 1H, OCHHCH$_2$CH$_2$NH—), 3.92 (t, J 6.6 Hz, 1H, H-5), 3.58 (m, 1H, H—OCHHCH$_2$CH$_2$NH—), 3.45 (m, 1H, OCH$_2$CH$_2$CHHNH—), 3.28 (m, 3H, OCH$_2$CH$_2$CHHNH, NHCO(CH$_2$)$_4$CH$_2$N$_3$), 2.21 (m, 2H, NHCOCH$_2$(CH$_2$)$_4$N$_3$), 2.17, 2.08, 2.06, 2.00 (4s, each 3H, 4×COCH$_3$), 1.78 (m, 2H, OCH$_2$CH$_2$CH$_2$NH—), 1.51 (m, 4H, NHCOCH$_2$CH$_2$(CH$_2$)$_3$N$_3$, NHCO(CH$_2$)$_3$CH$_2$CH$_2$N$_3$), 1.43 (m, 2H, NHCO(CH$_2$)$_2$CH$_2$(CH$_2$)$_2$N$_3$); $^{13}$C NMR (CDCl$_3$): δ=172.84, 170.39, 170.19, 170.08, 169.93 (CO.(CH$_2$)$_5$N$_3$, 4×COCH$_3$), 101.42 (C-1), 70.82 (C-3), 70.64 (C-5), 69.32 (C-2), 68.92 (C-4), 66.98 (OCH$_2$(CH$_2$)$_2$NH—), 61.20 (C-6), 51.29 (NHCO(CH$_2$)$_4$CH$_2$N$_3$), 37.55 (NHCOCH$_2$(CH$_2$)$_4$N$_3$), 36.24 (O(CH$_2$)$_2$CH$_2$NH—), 29.30, 28.63, 26.41, 25.22 (OCH$_2$CH$_2$CH$_2$NH—, NHCOCH$_2$CH$_2$CH$_2$CH$_2$CH$_2$N$_3$), 20.83, 20.68, 20.57 (4×COCH$_3$); m/z (MALDI$^+$) 567.14 [M+Na]$^+$; HR-MS calcd for C$_{23}$H$_{36}$N$_4$NaO$_{11}$$^+$ [M+Na]$^+$ 567.2273, found 567.2262.

Synthesis of 3-(N-Azidopentyloxycarbonyl)aminopropyl 2,3,4-tri-O-acetyl-β-D-galactopyranoside (5)

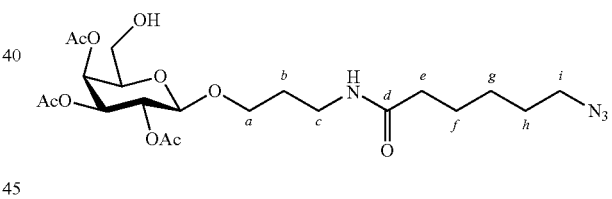

To a solution of 3-(N-Azidopentyloxycarbonyl)aminopropyl 2,3,4,6-tetra-O-acetyl-β-D-galactopyranoside (3.0 g, 5.5 mmol) in dry methanol (20 mL) was added 1 M sodium methoxide-methanol (NaOMe-MeOH, 0.25 mL) and the reaction was stirred at room temperature for 1 h. The mixture was then neutralized with Amberlite IR 120 (H$^+$) resin, the solution filtered and the filtrate concentrated in vacuo to a gum. TLC (ethyl acetate) indicated absence of starting material. The residue was taken up in dimethylformamide (DMF, 10 mL), the solution was cooled to 0° C. and tert-butyldimethylsilyl chloride (TBDMS-Cl, 1.1 g, 7.5 mmol) was added. The reaction mixture was stirred at room temperature for 4 h after which the DMF was removed in vacuo. The residual oil was taken up in a mixture of pyridine (Pyr, 10 mL) and acetic anhydride (Ac$_2$O, 10 mL) and the reaction mixture was stirred at room temperature overnight. Solvents were then removed in vacuo, the resulting residue was taken up in CH$_2$Cl$_2$ (50 mL), washed with water and the organic extract was dried (MgSO$_4$) and concentrated in vacuo to give the acetylated TBDMS ether, [$R_f$=0.6 (ethyl acetate/hexane 3:1)]. This material was dissolved in 10% trifluoroacetic acid (TFA) in 80% aqueous acetic (aq. AcOH)

mixture (10 mL), allowed to stand at room temperature for 1 h until TLC showed the complete disappearance of starting material (product TLC: $R_f$=0.3, ethyl acetate) and solvents were removed in vacuo. The residue was subjected to column chromatography on silica (ethyl acetate/hexane, stepwise gradient 5:1, 3:1, 1:0) to give primary alcohol 5 as a syrup (1.8 g, 65% over 4 steps). $^1$H NMR (CDCl$_3$): δ=6.12 (bs, 1H, NH), 5.26 (dd, 1H, H2, $^3J_{1,2}$=7.9 Hz, $^3J_{2,3}$=10.3 Hz), 4.97 (dd, 1H, H3, $^3J_{2,3}$=10.3 Hz, $^3J_{3,4}$=3.2 Hz), 4.43 (d, 1H, H1, $^3J_{1,2}$=7.9 Hz), 4.3 (m, 2H, H6), 4.06 (d, 1H, H4, $^3J_{3,4}$=3.2 Hz), 3.98 (m, 1H, Ha), 3.66-3.53 (m, 1H, Ha), 3.49-3.29 (m, 2H, Hc), 3.28 (t, 2H, Hi, $^3J_{h,i}$=6.8 Hz), 2.22 (t, 2H, He, $^3J_{e,f}$=7.5 Hz), 2.09, 2.07, 2.05 (3s, 9H, CH$_3$C(O)), 1.86-1.73 (m, 2H, Hb), 1.71-1.59 (m, 4H, Hf, Hh), 1.45-1.37 (m, 2H, Hg); $^{13}$C NMR (CDCl$_3$): δ=173.2, 170.9, 171.1, 171.0 (4×s, 4C, 3×CH$_3$CO—, Cd), 101.2 (d, 1C, H1), 72.9 (d, 1C, C3), 69.1 (dt, 3C, C2, Ca), 61.9 (t, 1C, C6), 51.1 (t, 1C, Ci), 37.6 (t, 1C, Cc), 36.2 (t, 1C, Ce), 29.1 (t, 1C, Cb), 28.4 (t, 1C, Cf), 26.3 (t, 1C, Cg), 25.2 (t, 1C, Ch), 20.8 (3×q, 3C, 3×CH$_3$C(O)); m/z (MALDI$^+$) 525.01 [M+Na]$^+$; HR-MS calcd for $C_{21}H_{34}N_4NaO_{10}^+$ [M+Na]$^+$ 525.2167, found 525.2163.

Synthesis of 3-(N-Azidopentyloxycarbonyl)amino-propyl 2,3,4-tri-O-acetyl-6-O-trifluoromethanesulfo-nyl-β-D-galactopyranoside (6)

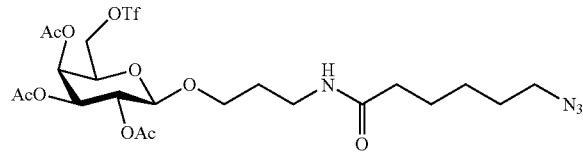

To a stirred solution of primary alcohol 5 (0.2 g, 0.4 mmol) in dry CH$_2$Cl$_2$ (10 mL) at 0° C. under nitrogen was added pyridine (126 µL, 1.5 mmol), followed by triflic anhydride (Tf$_2$O, 140 µL, 1 mmol). The reaction was stirred at 0° C. for 30 min when TLC showed complete conversion to product ($R_f$=0.7, ethyl acetate). CH$_2$Cl$_2$ (25 mL) was added, the organic solution was washed with 1 M HCl (25 mL), dried (MgSO$_4$) and concentrated in vacuo to approximately 10 mL. The resulting solution was applied to a silica column (1 cm×2 cm) and the product was washed through with ethyl acetate. The eluted fraction was mixed with DMF (2 mL) and the ethyl acetate removed in vacuo to leave the product 6 in a DMF solution for subsequent use. [NB—triflate 6 rapidly decomposes on concentration to dryness].

Synthesis of 3-(N-Azidopentyloxycarbonyl)amino-propyl S-(methyl 5-acetamido-3,5-dideoxy-D-glycero-α-D-galacto-2-nonulopyranosylonate)-(2-6)-6-deoxyl-6-thio-β-D-galactopyranoside (8)

To a stirred solution of known per-N, O-acetylated sialic acid thioacetate 7[3] (0.15 g, 0.3 mmol) in DMF (2 mL) at 0° C. under nitrogen was added diethylamine (Et$_2$NH, 0.5 mL, 19 mmol). After 15 min a solution of triflate 6 in DMF (vide supra) was added at 0° C. and the reaction was stirred for 2 h. DMF was then removed in vacuo, the resulting residue was taken up in CH$_2$Cl$_2$ (25 mL), washed with water, dried (MgSO$_4$) and concentrated to dryness. The residue was subjected to column chromatography on silica (stepwise gradient ethyl acetate, ethyl acetate/methanol 95:5) to give the acetylated thioglycoside intermediate as a glass. $R_f$=0.3 (ethyl acetate/methanol 95:5); m/z (MALDI$^+$) 1014.31 [M+Na]$^+$, calcd for $C_{41}H_{61}N_5NaO_{21}S$ [M+Na]$^+$=1014.36. To a solution of the acetylated intermediate (0.12 g, 120 µmol) in dry methanol (2 mL) was added 1 M sodium methoxide-methanol (50 µL) and the reaction was stirred at room temperature for 1 h. The reaction mixture was neutralized with Amberlite IR 120 (H$^+$) resin, the solution was filtered and the filtrate was concentrated in vacuo to a solid. This material was purified by TSK gel chromatography (water, flow rate 0.5 mL/min) to give de-O-acetylated azide 8 as a white solid (40 mg, 25% over 3 steps). $^1$H NMR (D$_2$O): δ=4.27 (d, 1H, H1', $^3J_{1,2}$=7.9 Hz), 3.89 (d, 1H, H4', $^3J_{3',4'}$=3.4 Hz, $^3J_{4',5'}$=1.1 Hz), 4.84-3.60 (m, 7H, H4, H6', H7, H8, Ha), 3.81 (s, 3H, CH$_3$CO), 3.54 (dd, 2H, H3', $^3J_{2',3'}$=10.0 Hz, $^3J_{3',4'}$=3.4 Hz), 3.48 (dd, 1H, H5', $^3J_{4',5'}$=1.1 Hz, $^3J_{5',6'}$=8.7 Hz), 3.40 (dd, 1H, H2', $^3J_{1',2'}$=7.9 Hz, $^3J_{2',3'}$=10.0 Hz), 3.26 (t, 2H, Hi, $^3J_{h,i}$=6.8 Hz), 3.21 (m, 2H, Hc), 3.0-2.83 (m, 2H, H9), 2.76 (dd, 2H, H3$_{eq}$, $^2J_{3ax,3eq}$=12.8 Hz, $^3J_{3eq,4}$=4.7 Hz), 2.22 (t, 2H, He, $^3J_{e,f}$=7.3 Hz), 1.96 (s, 3H, CH$_3$CO.NH), 1.80 (m, 1H, H3$_{ax}$), 1.70 (m, 2H, Hb), 1.59-1.44 (m, 4H, Hf, Hh), 1.42-1.26 (m, 2H, Hg); $^{13}$C NMR (D$_2$O): δ=176.8, 174.9, 171.0 (3s, 4C, CH$_3$C(O)O, C2, CH$_3$C(O)NH), Cd), 102.8 (d, 1C, H1'), 75.0, 73.8 (dd, 2C, C7, C8), 72.8 (d, 1C, C3'), 70.4 (d, 1C, C2'), 68.9 (d, 1C, C2, C4'), 68.0 (d, 1C, C5'), 67.7 (t, 1C, Ca), 67.5 (d, 1C, C4), 63.0 (t, 1C, C6'), 51.5 (q, 1C, CH$_3$C(O)O), 51.1 (t, 1C, Ci), 39.9 (t, 1C, C3), 36.1 (t, 1C, Cc), 35.6 (t, 1C, Ce), 29.0 (t, 1C, C9), 28.4 (t, 1C, Cb), 27.6 (t, 1C, Cf), 25.3 (t, 1C, Cg), 24.9 (t, 1C, Ch), 21.9 (q, 1C, CH$_3$CONH); m/z (MALDI$^+$) 720.16 [M+Na]$^+$, HR-MS calcd for $C_{27}H_{47}N_5NaO_{14}S$ [M+Na]$^+$ 720.2737, found 720.2740.

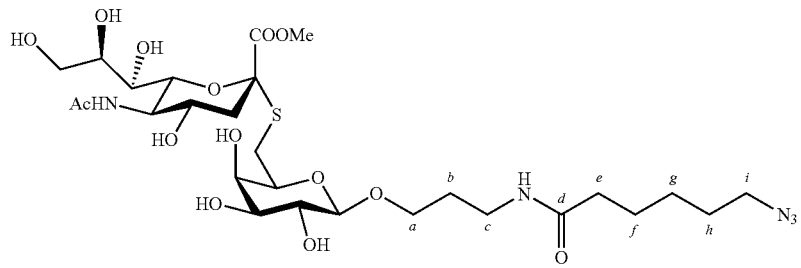

Synthesis of N-(tert-Butyloxycarbonyl)-N-(butanoyl)tris[(propargyloxy)methyl]aminomethane (9)

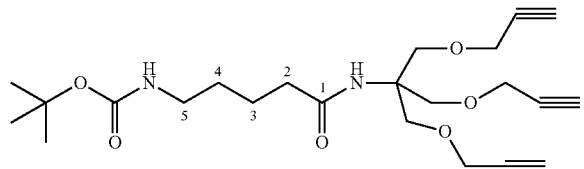

Known tri-O-propargyl-trishydroxymethylaminomethane[4] (0.15 g, 0.5 mmol) was dissolved in 80% aqueous trifluoroacetic acid (1 mL) and the solution allowed to stand at room temperature for 15 min after which the solvents were removed in vacuo. The residue was co-evaporated with ethanol and then toluene to give a yellow oil (0.1 g). This oil was taken up in dry DMF (0.5 mL) and added to a mixture of commercial N-Boc aminopentanoic acid (86 mg, 0.4 mmol), HATU (2-(1H-7-Azabenzotriazol-1-yl)-1,1,3,3-tetramethyl uronium hexafluorophosphate) (0.2 g, 0.5 mmol), N-methylmorpholine (0.1 g, 1 mmol) in DMF (1 mL). The reaction was stirred at room temperature overnight, the DMF removed in vacuo, the resulting residue was taken up in $CH_2Cl_2$ (25 mL), washed with water, dried ($MgSO_4$) and concentrated to dryness. The residue was purified by column chromatography on silica (stepwise gradient, ethyl acetate/hexane 5:95, 25:75, 40:60) to yield compound 9 as a syrup (0.14 g, 78%). $R_f$ 0.7 (ethyl acetate/hexane 1:1). $^1$H NMR ($CDCl_3$): δ=5.71 (brs, 1H, NH), 4.65 (brs, 1H, NH), 4.15 (s, 6H, 3×$OCH_2C\equiv CH$), 3.84 (s, 6H, $NHC(CH_2O)_3$—), 3.13 (m, 2H, $NHCH_2$—), 2.44 (s, 3H, 3×$OCH_2C\equiv CH$), 2.19 (t, $J_{HH}$=7.2 Hz, 2H, —$CH_2CONH$—), 1.65 (m, 2H, —$NHCH_2CH_2CH_2$—), 1.52 (m, 2H, —$NHCH_2CH_2CH_2$—), 1.48 (s, 9H, 3×$CCH3$); m/z (MALDI$^+$) 435.04 [M+H]$^+$; HR-MS calcd for $C_{23}H_{35}N_2O_6^+$ [M+H]$^+$ 435.2490, found 435.2490.

Synthesis of N-Boc-Protected Trivalent Methyl Ester (10)

To a stirred solution of azide 8 (10 mg, 14 μmol) and tri-propargyl ether 9 (2 mg, 4.6 μmol) in tert-butanol/water 1:1 (tBuOH/$H_2O$, 2 mL) was added premixed aqueous 1 M copper sulphate ($CuSO_4$, 1 μL, 1 μmol) and 1 M sodium ascorbate (NaAsc, 2 μL, 2 μmol). The reaction mixture was stirred at 50° C. for 2 h and solvents were removed in vacuo. The resulting residue was taken up in water (0.5 mL), filtered through a 0.2 μm syringe filter and the solution was applied to a TSK gel column (water, 0.5 mL/min). The tri-clicked product 10 was obtained as a white solid (5 mg, 43%). $^1$H NMR (600 MHz; $D_2O$): δ=7.63 (s, 3H, CHNN), 4.09 (t, 6H, Hi, $^3J_{h,i}$=6.7 Hz), 3.99 (d, 3H, H1', $^3J_{1',2}$=7.9 Hz), 3.64 (d, 3H, H4', $^3J_{3',4'}$=3.4 Hz), 3.60-3.30 (m, 21H, H4, H7, H8, H6', Ha), 3.54 (s, 9H, $CH_3CO$—), 3.29 (dd, 6H, H3', $^3J_{1',2}$=9.8 Hz, $^3J_{3,4}$=3.4 Hz), 3.23 (d, 3H, H6, $^3J_{6,7}$=9.0 Hz), 3.16 (dd, 3H, H2', $^3J_{1',2}$=7.9 Hz, $^3J_{2',3}$=9.8 Hz), 2.94 (m, 6H, Hc), 2.6-2.7 (m, 6H, H9), 2.67 (t, 2H, Ht, $^3J_{s,t}$=6.7 Hz), 2.48 (dd, 6H, H3$_{eq}$, $^2J_{3e,3a}$=12.8 Hz, $^3J_{3e,4}$=4.5 Hz), 1.89 (t, 6H, He, $^3J_{e,f}$=6.7 Hz), 1.85 (t, 2H, Hq, $^3J_{s,t}$=7.2 Hz), 1.71 (s, 3H, $CH_3CO$—), 1.56-1.53 (2×m, 9H, H3$_{ax}$, Hh), 1.55 (m, 3H), 1.47 (m, 6H, Hb), 1.28 (m, 6H, Hf), 1.17 (m, 2H, Hq), 1.07 (m, 2H, Hs), 1.07 (m, 6H, Hg); $^{13}$C NMR ($D_2O$): δ=176.4, 174.9, 174.0, 171.0 (4×s, 8C, $CH_3CO$—, Cd, Cp, Cu), 143.9 (s, 3C, Ck), 124.8 (d, 3C, Cj), 102.9 (d, 3C, C1'), 94.0 (s, 3C, C2), 83.1 (s, 1C, Cv), 73.7 (d, 3C, C7 or C8), 72.7 (d, 3C, C3'), 70.9 (d, 3C, C4), 70.4 (d, 3C, C2'), 69.0 (2×d, 6C, C2, C4'), 68.1 (d, 3C, C6), 67.7 (t, 3C, Ca), 67.6 (d, 3C, C8 or C7), 59.6 (2×t, 6C, C6', Cl), 53.6 (q, 3C, $CH_3C(O)O$), 50.2 (t, 3C, Ci), 40.0 (t, 3C, C3), 39.4 (t, 1C, Ht), 36.1 (t, 3C, Cc), 35.7 (t, 1C, Cq), 35.5 (t, 3C, Ce), 29.1 (2×t, 6C, C9, Ch), 28.4 (2×t, 4C, Cb, Cs), 25.0 (t, 3C, Cg), 24.7 (t, 3C, Cf), 22.0 (t, 1C, Cr); m/z (MALDI$^+$) 2591.19 [M+Cu]$^+$, calcd for $C_{104}CuH_{175}N_{17}O_{48}6$ [M+Cu]$^+$=2591.33.

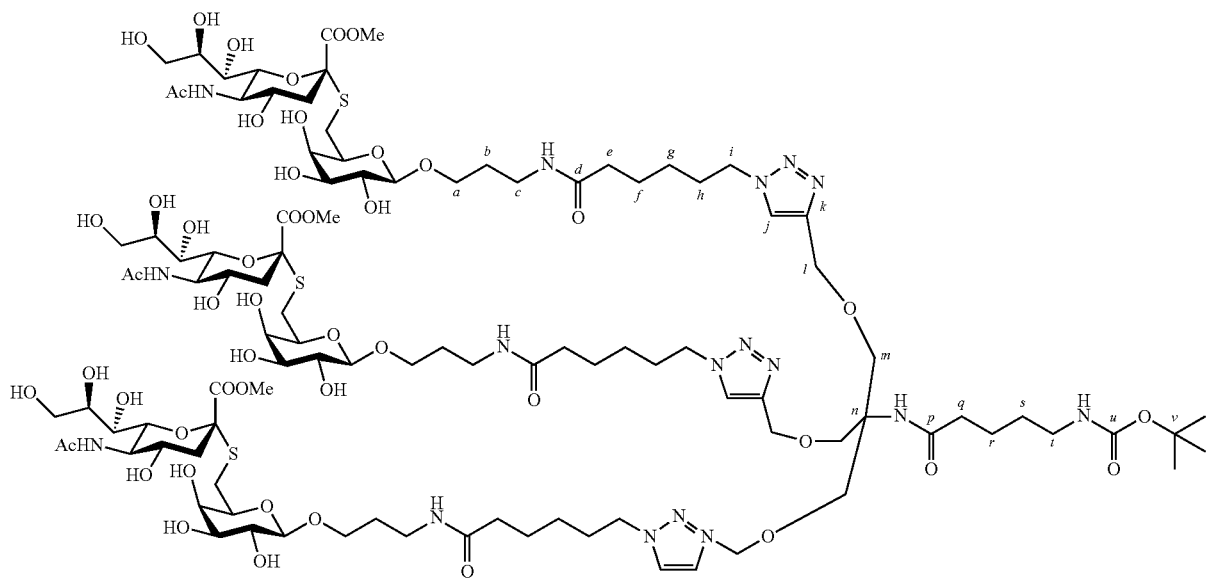

Synthesis of the Deprotected Mercaptobutyrate Derivative 1 (Trivalent Ligand 1)

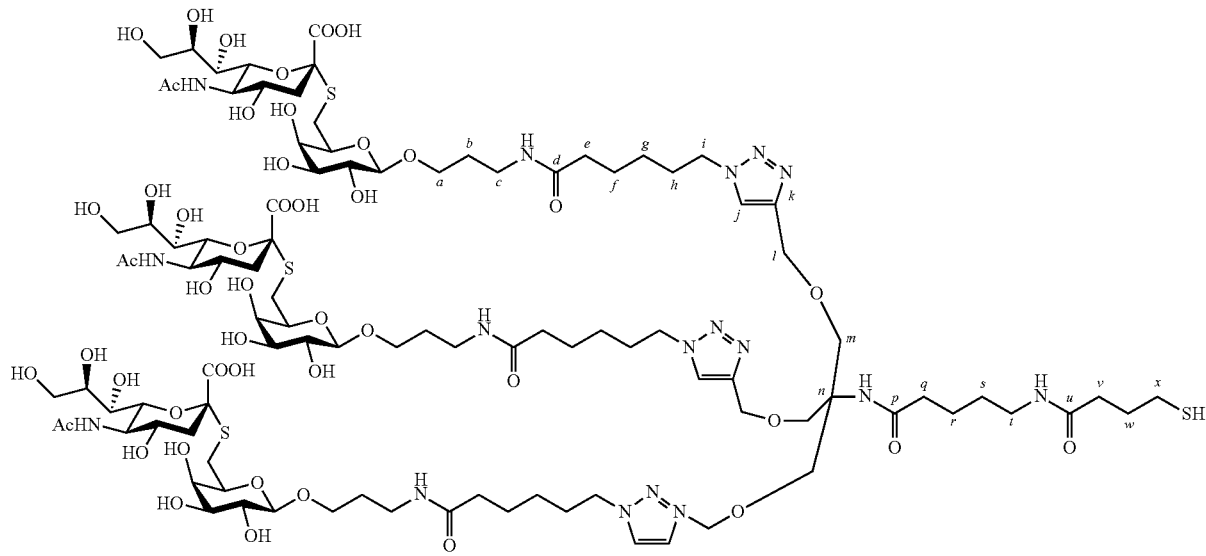

To a solution of N-Boc-protected trivalent methyl ester 10 (15 mg, 6 μmol) in water (1 mL) was added 1 M sodium hydroxide (NaOH, 10 μL) and the reaction was allowed to stand at room temperature for 12 h. The solution was neutralized with Amberlite IR-120 (H$^+$), filtered and freeze dried to give a white solid which was treated with 80% aqueous trifluoroacetic acid (100 μL) for 15 min. The solvent was evaporated in vacuo and the residue was taken up in 0.5 M sodium bicarbonate/ethanol 1.5:1 (2 mL). To this solution was added α-thiobutyrolactone (125 μL, 1.4 mmol) and dithiothreitol (DTT) (0.1 g, 0.7 mmol) and the reaction was heated at 50° C. for 2 h. The solvents were removed in vacuo, the resulting residue was taken up in water (0.5 mL), filtered through a 0.2 μm syringe filter and chromatographed on TSK gel (water, 0.5 mL/min) to yield the product 1 as a white solid (6 mg, 41% over 3 steps). $^1$H NMR (D$_2$O): δ=7.85 (s, 3H, CHNN), 4.48 (bs, 6H, HI), 4.33 (t, 6H, Hi, $^3J_{h,i}$=6.9 Hz), 4.26 (d, 3H, H1', $^3J_{1',2'}$=7.9 Hz), 3.93 (d, 3H, H4', $^3J_{3',4'}$=3.4 Hz), 3.39 (dd, 3H, H2', $^3J_{1',2'}$=7.9 Hz, $^3J_{2',3'}$=10.0 Hz), 3.18 (t, 6H, Hc, $^3J_{b,c}$=6.6 Hz), 2.87 (dd, 6H, H9), 2.73 (dd, 3H, H3$_{eq}$, $^2J_{3e,3a}$=12.2 Hz, $^3J_{3e,4}$=4.5 Hz), 2.60, 2.38, (2×t, 4H, Hq-Ht or Hv-x), 2.14 (t, 6H, He, $^3J_{e,f}$=7.6 Hz), 1.85-1.77 (m, 6H, Hh), 1.71 (m, 6H, Hb), 1.71-1.65 (m, 3H, H3$_{ax}$), 1.52 (m, 6H, Hf), 1.22-1.13 (m, 6H, Hg); $^{13}$C NMR (D$_2$O): δ=125.6 (d, 3C, CHNN), 102.5 (d, 3C, C1'), 70.4 (d, 3C, C2'), 68.7 (d, 3C, C4'), 63.2 (t, 3C, Cl), 49.9 (t, 3C, Ci), 36.3 (t, 3C, Cc), 35.3 (t, 3C, Ce), 29.2 (t, 3C, C9), 28.7 (t, 3C, Ch), 28.2 (t, 3C, Cb), 24.8 (t, 3C, Cg), 24.5 (t, 3C, Cf); m/z (MALDI$^+$) 2527.78 [M+K]$^+$, calcd for C$_{100}$H$_{168}$KN$_{17}$O$_{47}$ [M+K]$^+$=2527.85.

Synthesis of PEG Ligand 2

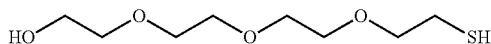 [SMILES: OCCOCCOCCOCCS]

The S-acetyl derivative of PEG ligand 2, purchased from Quanta Biodesign, was deacetylated with catalytic methoxide immediately prior to use.

Synthesis of t-butyl 2-(2-(2-(2-iodoacetamido)ethoxy)ethoxy)ethylcarbamate (12)

Iodoacetic anhydride (555 mg, 1.57 mmol) was dissolved in absolute diethylether (10 ml) and the solution was added to a stirred solution of t-butyl 2-(2-(2-aminoethoxy)ethoxy)ethylcarbamate (11) (299.6 mg, 1.21 mmol) in absolute diethylether (10 ml) under nitrogen atmosphere and with exclusion of light. The mixture was allowed to stir for 60 min at room temperature and the formation of product was followed by TLC (R$_f$=0.67, ethyl acetate/methanol 20:1). The volatiles were evaporated in vacuo and the residue was subjected to column chromatography on silica gel (first ethyl acetate then ethyl acetate/methanol 20:1) to give pure 12 (353.5 mg, 70%) as a pale yellow oil. $^1$H NMR (400 MHz; CDCl$_3$): δ=8.09 and 6.77 (2 bs, 1H, C—N rotamers NHC(O)CH$_2$), 5.55 and 5.01 (2 bs, 1H, C—N rotamers NHC(O)O), 3.66 (s, 2H, H$_2$1), 3.57 (bs, 4H, H$_2$5, H$_2$6), 3.51 (t, 4H, $^3J_{3,4}$=$^3J_{7,8}$=4.4 Hz, H$_2$4, H$_2$7), 3.43-3.39 (m, 2H, H$_2$3), 3.29-3.22 (m, 2H, H$_2$8), 1.40 (s, 9H, (CH$_3$)$_3$CO); $^{13}$C NMR (100 MHz; CDCl$_3$): δ=167.6 (s, 1C, C2), 156.3 (s, 1C, C9), 79.5 (s, 1C, (CH$_3$)$_3$CO), 70.7, 70.5, 70.4, 69.6 (4×t, 4C, C4, C5, C6, C7), 40.6 (t, 1C, C8), 40.4 (t, 1C, C3), 28.7 (3×q, 3C, (CH$_3$)$_3$CO), −0.3 (t, 1C, C1); m/z (CI$^+$) 434 ([M+NH$_4$]$^+$, 12%), 417 ([M+H]$^+$, 68), 217 (100); HR-MS calcd for C$_{13}$H$_{26}$IN$_2$O$_5{}^+$ [M+H]$^+$ 417.0881, found 417.0882.

Synthesis of methyl (3',12'-diaza-15',15'-dimethyl-6',9'-dioxa-2',13'-dioxohexadecyl) 5-acetamido-4,7,8,9-tetra-O-acetyl-3,5-dideoxy-2-thio-D-glycero-α-D-galacto-2-nonulopyranosidonate (15)

To a solution of methyl 5-acetamido-4,7,8,9-tetra-O-acetyl-2-S-acetyl-3,5-dideoxy-2-thio-D-glycero-α-D-galacto-2-nonulopyranosidonate (13) (267 mg, 486 μmol) in absolute methanol (12.3 ml) cooled to −40° C. was added a 1M methanolic solution of MeONa (437 μl, 437 μmol) under nitrogen atmosphere. The mixture was stirred for 30 min at −40° C. and then neutralised with Amberlite IR-120 H$^+$ resin with stirring for 15 min at −40° C. The mixture was filtered and the filtrate was evaporated in vacuo to give crude methyl 5-acetamido-4,7,8,9-tetra-O-acetyl-3,5-dideoxy-2-thio-D-glycero-α-D-galacto-2-nonulopyranosidonate 14. The residue was dissolved in dichloromethane (15 ml) and the resulting solution was added to a solution of the iodoacetamide 12 (240 mg, 577 µmol) and N,N-diisopropylethylamine (254 µl, 1457 µmol) in dichloromethane (15 ml). The mixture was stirred for 12 hrs at room temperature and the reaction was monitored by TLC. The mixture was diluted with dichloromethane (30 ml) and washed with water (10 ml). The organic layer was dried over MgSO$_4$, filtered, evaporated and the residue was subjected to column chromatography on silica gel (7 g, ethyl acetate/hexane 1:10, then pure ethyl acetate, then pure dichloromethane to elute unreacted iodoacetamide 12 followed by stepwise gradient of dichloromethane/methanol 40:1, 30:1 and 20:1) to give pure 15 (251.2 mg, 65% over 2 steps). $R_f$=0.58 (chlorofom/methanol 10:1); $[\alpha]_D^{25}$+8.8 (c=0.49, CHCl$_3$); $^1$H NMR (400 MHz; CDCl$_3$): δ=6.95 and 6.79 (bs, 1H, C—N rotamers NHC(O)CH$_2$), 5.39 (bs, 1H, H7), 5.31-5.22 (m, 2H, H8, CH$_3$C(O)NH), 4.99 (bs, 1H, NHC(O)OtBu), 4.81 (ddd, 1H, $^3J_{4,5}$=$^3J_{4,3a}$=10.8 Hz, $^3J_{4,3e}$=4.2 Hz, H4), 4.21 (dd, 1H, $^2J_{9a,9b}$=12.4 Hz, $^3J_{9a,8}$=2.4 Hz, H9a), 4.01-3.96 (m, 2H, H5, H9b), 3.76-3.70 (m, 1H, H6), 3.70 (s, 3H, COOCH$_3$), 3.52-3.46 (m, 10H, H$_2$4', H$_2$5', H$_2$6', H$_2$7', H1'a, H3'a), 3.40-3.33 (m, 1H, H3'b), 3.26-3.22 (m, 3H, H1'b, H$_2$8'), 2.68 (dd, 1H, $^2J_{3e,3a}$=12.8 Hz, $^3J_{3e,4}$=4.2 Hz, H3e), 2.14, 2.09, 1.99, 1.97 (4×s, 12H, 4×CH$_3$C(O)O), 1.92-1.88 (m, 1H, H3a), 1.81 (s, 3H, CH$_3$C(O)NH), 1.38 (s, 9H, (CH$_3$)$_3$CO); $^{13}$C NMR (100 MHz; CDCl$_3$): δ=170.2, 169.9, 169.7, 169.2, 169.1, 167.6, 167.3 (7×s, 8C, C2', COOCH$_3$, 4×CH$_3$C(O)O, CH$_3$C(O)NH), 155.0 (s, 1C, C9'), 81.1 (s, 1C, C2), 78.2 (s, 1C, (CH$_3$)$_3$CO), 72.9 (d, 1C, C6), 69.2, 68.7 (2×t, 4C, C4', C5', C6', C7'), 68.4 (d, 1C, C4), 66.9 (d, 1C, C7), 65.9 (d, 1C, C8), 61.3 (t, 1C, C9), 52.2 (q, 1C, COOCH$_3$), 48.2 (d, 1C, C5), 39.3 (t, 1C, C8'), 38.6 (t, 1C, C3'), 36.4 (t, 1C, C3), 31.5 (t, 1C, C1'), 27.4 (q, 3C, (CH$_3$)$_3$CO), 22.2 (q, 1C, CH$_3$C(O)NH), 20.4, 19.9, 19.8 (3×q, 4C, 4×CH$_3$C(O)O); m/z (ESI$^+$) 818 ([M+Na]$^+$, 100%), 796 ([M+H]$^+$, 71), 696 (5); HR-MS calcd for C$_{33}$H$_{54}$N$_3$O$_{17}$S$^+$ [M+H]$^+$ 796.3168, found 796.3168.

Synthesis of 3',12'-diaza-6',9'-dioxa-2',13'-dioxo-17'-thiaheptadecyl 5-acetamido-3,5-dideoxy-2-thio-D-glycero-α-D-galacto-2-nonulopyranosidonic acid (monovalent ligand 3)

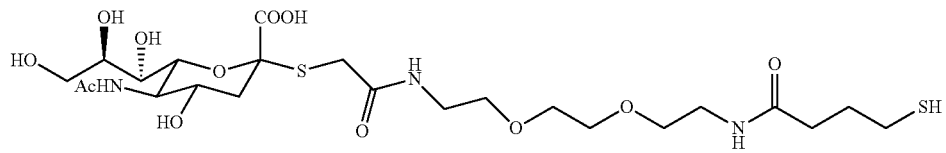 [SMILES: CC(=O)NC1C(O)CC(SCC(=O)NCCOCCOCCNC(=O)CCCS)(C(=O)O)OC1[C@H](O)[C@H](O)CO]

Thioglycoside 15 (178 mg, 224 µmol) was dissolved in absolute methanol (8.3 ml) and treated with 0.5 N NaOMe in methanol (966 µl, 484 µmol). After stirring for 1 hr at room temperature (TLC monitoring, product $R_f$=0.08 (chloroform/methanol 10:1)), the solvent was removed in vacuo and then 1 N NaOH (1.72 ml, 1.72 mmol) was added to the residue. After stirring for 1.5 hr, a 1:1 mixture of glacial acetic acid/water (1.6 ml) was added and then the volatiles were evaporated in vacuo. The residue was dissolved in dichloromethane (4.2 ml) and treated with trifluoroacetic acid (4.2 ml) at room temperature. After 3 h, the reaction mixture was concentrated to give the crude TFA salt of amine that was used without further purification. The crude amine (~115 mg, ~224 µmol) was dissolved in a mixture of 0.5 M sodium bicarbonate (10.3 ml, pH~9.0) and ethanol (8.2 ml) and then dithiothreitol (173 mg, 1.12 mmol) and γ-thiobutyrolactone (194 µl, 2.24 mmol) were added. The mixture was stirred overnight at 50° C. under nitrogen atmosphere. Using 1M HCl the pH of the mixture was adjusted to 6.0. The mixture was concentrated in vacuo at 37° C. and the residue was freeze-dried. The residue was taken into methanol and filtered. The filtrate was evaporated and the residue was purified using column chromatography on silica gel (6 g, sample applied in methanol, chloroform/methanol 2:1, then chloroform/methanol/water 55:45:10) to give pure 3 (116 mg, 84% over 4 steps). The compound was stored neat at −20° C. under nitrogen atmosphere. $R_f$=0.58 (ethyl acetate/methanol/acetic acid/water 3:3:3:1); $^1$H NMR (400 MHz; D$_2$O): δ=3.85-3.79 (m, 2H, H5, H9a), 3.71-3.61 (m, 11H, H4, H8, H9b, H$_2$4', H$_2$5', H$_2$6', H$_2$7'), 3.59-3.53 (m, 2H, H6, H7), 3.49-3.41 (m, 6H, H$_2$1', H$_2$3', H$_2$8'), 2.79 (dd, 1H, $^2J_{3e,3a}$=12.4 Hz, $^3J_{3e,4}$=4.8 Hz, H3e), 2.56-2.52 (m, 2H, H$_2$12'), 2.39-34 (m, 2H, H$_2$10'), 2.01 (s, 3H, CH$_3$C(O)NH), 1.92-1.76 (m, 3H, H3a, H$_2$11'); $^{13}$C NMR (100 MHz; CDCl$_3$): δ=176.8, 175.6, 174.2, 172.5 (4×s, 4C, CH$_3$C(O)NH, C1, C2', C9'), 86.1 (s, 1C, C2), 75.5 (d, 1C, C6), 72.4 (d, 1C, C8), 70.1, 70.0, 69.4, 69.3 (4×t, 4C, C4', C5', C6', C7'), 69.1 (d, 1C, C4), 68.7 (d, 1C, C7), 63.2 (t, 1C, C9), 52.2 (d, 1C, C5), 41.1 (t, 1C, C3), 39.9, 39.5 (2×t, 2C, C3', C8'), 35.0 (t, 1C, C10'), 33.8 (t, 1C, C1'), 30.1 (t, 1C, C11'), 23.7 (t, 1C, C12'), 22.6 (q, 1C, CH$_3$C(O)NH); m/z (ESI$^+$) 660 ([M−H+2Na]$^+$, 100%), 638 ([M+Na]$^+$, 21); m/z (ESI$^-$) 614 ([M−H]$^+$, 100%); HR-MS calcd for C$_{23}$H$_{41}$N$_3$NaO$_{12}$S$_2^+$ [M+Na]$^+$ 638.2024, found 638.2028.

Synthesis of Citrate Coated Gold Nanoparticles, Functionalized Gold Nanoparticles and Virus Detection Reagents All reagents were of analytical grade, used as received and purchased from Sigma-Aldrich (UK) unless specified. Millex GP syringe driven filter units (0.22 µm) and Amicon Ultra-4 centrifugal filter units (10,000 MW cut-off) were purchased from Millipore Corporation, USA. Inactivated viruses: X31 and RG14 and allantoic fluid (AF) virus X31 were provided by the WHO Collaborating Centre for Reference and Research on Influenza, Division of Virology, National Institute of Medical Research, UK.

Instrumental Methods

UV-Visible spectra were recorded using a Perkin Elmer Lambda 25 UV-Vis spectrometer at room temperature. Quartz cuvettes with a 1 cm path length were used. Transmission electron microscopy (TEM) images were obtained using a Jeol 2000EX transmission electron microscope, operating at 200 KV, by depositing samples on holey carbon film 300 mesh copper grids from Agar Scientific, UK.

Synthesis of Citrate Stabilized Gold Nanoparticles

Water soluble gold nanoparticles were prepared via the citrate reduction method reported by Enüstün and Turkevich.[5] Briefly, aqueous solutions of $HAuCl_4 \cdot 3H_2O$ (12.5 mg, 32 µmol, in 100 mL) and sodium citrate tribasic dihydrate (50 mg, 168 µmol, in 50 mL) were prepared and heated to 60° C. The sodium citrate solution was rapidly added to the gold solution while stirring vigorously. The temperature was increased to 85° C. and the solution was stirred for 2.5 h. A clear red gold nanoparticle solution was obtained that was cooled to room temperature and filtered through a Miller GP syringe driven filter unit (0.22 µm). The particle concentration in the citrate stabilized gold nanoparticles solution was approximately 3 nM.

Synthesis of Gold Nanoparticles Functionalized with Trivalent Ligand 1 and PEG Ligand 2 (Trivalent Ligand 1:PEG Functionalized Gold Nanoparticles)

Gold nanoparticles were functionalized with varying ratios of trivalent ligand 1 and PEG ligand 2. Varying molar ratios of trivalent ligand 1 and PEG based ligand 2 (Table 4) were added to aliquots of freshly prepared gold nanoparticles (17 mL) and stirred for 60 h at room temperature to ensure self-assembly of the ligands onto the gold surface. The nanoparticle solution was centrifuged using Amicon Ultra-4 centrifugal filter units (10,000 MW cut-off) in a Sorvall Legend RT centrifuge for 10 min at 4,000×g to remove the excess trivalent ligand 1 and PEG ligand 2. The centrifuged nanoparticles were resuspended in Tris buffer solution (17 mL, 10 mM, pH 7.6). The centrifugation process was repeated a total of two times.

TABLE 4

Molar ratios of trivalent ligand 1 and PEG ligand 2 added to the gold nanoparticles.

| % Trivalent ligand 1 | Quantity of trivalent ligand 1 added (nmol) | % PEG ligand 2 | Quantity of PEG ligand 2 added (nmol) |
| --- | --- | --- | --- |
| 50 | 15.1 | 50 | 15.1 |
| 25 | 7.6 | 75 | 22.6 |
| 10 | 3.0 | 90 | 27.2 |
| 5 | 1.5 | 95 | 28.7 |
| 2 | 0.6 | 98 | 29.6 |

Synthesis of Gold Nanoparticles Functionalized with Monovalent Ligand 3 and PEG Ligand 2 (Monovalent Ligand 3:PEG Functionalized Gold Nanoparticles)

Gold nanoparticles were functionalized with varying ratios of monovalent ligand 3 and PEG ligand 2. Varying molar ratios of monovalent ligand 3 and PEG based ligand 2 (Table 5) were added to aliquots of freshly prepared gold nanoparticles (17 mL) and stirred for 60 h at room temperature to ensure self-assembly of the ligands onto the gold surface. Excess ligands were removed as previously described for gold nanoparticles functionalized with trivalent ligand 1 and PEG ligand 2.

TABLE 5

Molar ratios of monovalent ligand 3 and PEG ligand 2 added to the gold nanoparticles.

| % Monovalent ligand 3 | Quantity of monovalent ligand 3 added (nmol) | % PEG ligand 2 | Quantity of PEG ligand 2 added (nmol) |
| --- | --- | --- | --- |
| 50 | 15.1 | 50 | 15.1 |
| 25 | 7.6 | 75 | 22.6 |
| 10 | 3.0 | 90 | 27.2 |
| 5 | 1.5 | 95 | 28.7 |
| 2 | 0.6 | 98 | 29.6 |

Synthesis of Gold Nanoparticles Functionalized with PEG Ligand 2 (PEG Functionalized Gold Nanoparticles)

PEG ligand 2 (30.2 nmol) was added to a freshly prepared citrate stabilized gold nanoparticles solution (17 mL). The solution was stirred for 60 h at room temperature to ensure self-assembly of the ligand onto the gold surface. Excess ligands were removed as previously described for gold nanoparticles functionalized with trivalent ligand 1 and PEG ligand 2.

Optimized Functionalization of Gold Nanoparticles for the Detection of Human Influenza Virus X31 virus (H3N2) (2.55 µg/mL) was added to a sample of each of the synthesized gold nanoparticles including: citrate coated gold nanoparticles; trivalent ligand 1:PEG functionalized gold nanoparticles (50:50, 25:75, 10:90, 5:95 and 2:98); and monovalent ligand 3:PEG functionalized gold nanoparticles (50:50, 25:75, 10:90, 5:95 and 2:98). The samples were stirred at room temperature and the UV-Vis spectrum was recorded before addition of the virus and 0, 15, 30, 60 and 240 min after addition of the virus.

Colorimetric Detection of X31 Virus Using Trivalent Ligand 1:PEG (25:75), Monovalent Ligand 3:PEG (25:75) and PEG Functionalized Gold Nanoparticles Increasing concentrations of X31 virus (from 0 to 3 µg/mL) were added to a sample of the functionalized gold nanoparticles. The UV-Vis spectrum of each functionalized gold nanoparticle solution was measured before addition of the virus and 30 min after addition of the corresponding virus concentration.

Colorimetric Detection of Influenza X31 Virus from Allantoic Fluid Using Trivalent Ligand 1:PEG (25:75) Functionalized Gold Nanoparticles Increasing volumes of X31 virus from allantoic fluid (AF) (from 0 to 43.1 µL) were added to a sample of trivalent ligand 1:PEG (25:75) functionalized gold nanoparticles (1000 µL). The UV-Vis spectrum of the sample was measured before addition of the AF X31 virus and 30 min after addition of the corresponding volume. As control experiment of effect of dilution, the same measurements were repeated although adding increasing volumes of Tris buffer (from 0 to 47.1 µL) to a sample of trivalent ligand 1:PEG (25:75) functionalized gold nanoparticles (1000 µL).

Colorimetric Detection of Avian RG14 Virus Using Trivalent Ligand 1:PEG (25:75) Functionalized Gold Nanoparticles Increasing concentrations of avian RG14 virus (H5N1) (from 0 to 6.8 µg/mL) were added to a sample of trivalent ligand 1:PEG (25:75) functionalized gold nanoparticles. The UV-Vis spectrum of the sample was measured before addition of the virus and 30 min after addition of each virus concentration.

Discrimination Between Human X31 (H3N2) and Avian RG14 (H5N1) Influenza Virus Using Trivalent Ligand 1:PEG (25:75) Functionalized Gold Nanoparticles Each virus (6.8 µg/mL) was added to a sample of trivalent ligand 1:PEG (25:75) functionalized gold nanoparticles. The UV-Vis spectrum of each sample was measured after stirring the samples for 6 days at room temperature.

References Example 2

[1] J. A. F. Joosten, V. Loimaranta, C. C. M. Appeldoorn, S. Haataja, F. A. El Maate, R. M. J. Liskamp, J. Finne, R. J. Pieters, *J. Med. Chem.* 2004, 47, 6499-6508.

[2] C. Grandjean, A. Boutonnier, C. Guerreiro, J.-M. Fournier, L. A. Mulard, *J. Org. Chem.* 2005, 70, 7123-7132.

[3] A. Hasegawa, J. Nakamura, M. Kiso, *J. Carbohydr. Chem.* 1986, 5, 11-19.

[4] Y. M. Chabre, C. Contino-Pépin, V. Placide, T. C. Shiao, R. Roy, *J. Org. Chem.* 2008, 73, 5602-5605.

[5] B. V. Enüstün, J. Turkevich, *J. Am. Chem. Soc.* 1963, 85, 3317-3328.

The invention claimed is:

1. A nanoparticle probe comprising a plurality of glycoconjugate ligands, each glycoconjugate ligand (GL) having a plurality of sialic-acid containing recognition groups (Y) coupled to the nanoparticle via a multivalent core (X), wherein the multivalent core (X) is a trivalent core, whereby there are 3 recognition groups per ligand, wherein the recognition groups on the bioconjugate specifically bind to the hemagglutinin on a target influenza virus, wherein the probe has at least one further type of ligand bound to the nanoparticle, wherein the further type of ligand is polyethylene glycol (PEG) which does not bind specifically to the target influenza virus and is used to modulate density of the glycoconjugate ligand on the surface of the nanoparticle to optimize binding and specificity, and wherein the molar ratio of glycoconjugate ligand: further ligand is between 10:90 and 90:10.

2. The nanoparticle probe of claim 1, wherein the or each recognition group terminates with the a-anomer of a sialic acid moiety, and the sialic acid moiety is bound to a monosaccharide through a 2,6 glycosidic bond or 2,3 glycosidic bond.

3. The nanoparticle probe of claim 2, wherein the target influenza virus is a human influenza virus or avian influenza virus.

4. The nanoparticle probe of claim 3, wherein the human influenza virus is an H3 virus.

5. The nanoparticle probe of claim 1, wherein the sialic acid moiety and monosaccharide are thio linked.

6. The nanoparticle probe of claim 1, wherein the monosaccharide is galactose.

7. The nanoparticle probe of claim 1, wherein the PEG is a thiolated PEG.

8. The nanoparticle probe of claim 1, wherein the molar ratio of glycoconjugate ligand: further ligand is between 15:85 and 35:65.

9. The nanoparticle probe of claim 8, wherein the molar ratio of glycoconjugate ligand: further ligand is between 20:80 and 30:70.

10. The nanoparticle probe of claim 9, wherein the molar ratio of glycoconjugate ligand: further ligand is about 25:75.

11. The nanoparticle probe of claim 1, wherein the nanoparticle is a gold nanoparticle, from about 10 to about 30 nm diameter.

12. The nanoparticle probe of claim 1, wherein each nanoparticle probe comprises a mean number of equal to, or at least, 5, 10, 25, 50 100 or 200 glycoconjugate ligand molecules per nanoparticle.

13. The nanoparticle probe of claim 1 wherein the glycoconjugate ligand (GL) is of the formula:

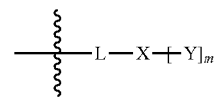

wherein:

Y is a sialic-acid containing recognition group;

m =3

X is a multivalent core moiety

L is a linking moiety which attaches the GL to the nanoparticle.

14. The nanoparticle probe of claim 13, wherein L =a thiolinkage.

15. The nanoparticle probe of claim 13, wherein group X comprises a multivalent carbon atom to which three Y recognition groups are linked via $X^L$ groups:

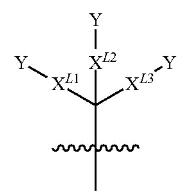

wherein $X^{L1}$, $X^{L2}$ and $X^{L3}$ are selected from $—CH_2—O—CH_2—$or $CH_2—S—CH_2—$.

16. The nanoparticle probe of claim 15, wherein the anomeric centre of the sialic acid moieties of the Y groups are separated from the multivalent carbon atom by 20 to 30 bond lengths or 1.5 to 3 nm.

17. The nanoparticle probe of claim 13, wherein X is a moiety of the following formula:

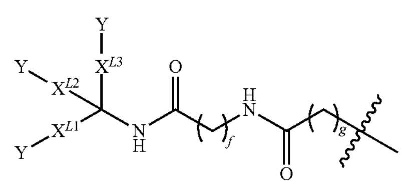

wherein f is 4 and g is 3, and wherein $X^{L1}$, $X^{L2}$ and $X^{L3}$ are $—CH_2—O—CH_2—$.

18. The nanoparticle probe of claim 13, wherein Y comprises a spacer moiety (Z) which connects the sialic acid containing moiety to the core group X, wherein Z comprises an alkylene or alkenylene group.

19. The nanoparticle probe of claim 18, wherein the alkylene or alkenylene group includes one or more amine, amide, ether, ester or thioester linkages.

20. The nanoparticle probe of claim 18, wherein the alkylene or alkenylene group is interrupted by one or more heteroatoms and/or aromatic rings.

21. The nanoparticle probe of claim 13, wherein Z comprises a triazole group and/or an amide.

22. The nanoparticle probe of claim 21, wherein Z is a moiety of the following formula:

d is 3 and e is 5.

23. The nanoparticle probe of claim 22, wherein Y has the following formula:

24. The nanoparticle probe of claim 23, wherein the glycoconjugate ligand compound has the following formula:

25. A method for specifically detecting a target influenza virus in a sample, the method comprising:
   (a) providing a nanoparticle probe as claimed in claim 1,
   (b) contacting the nanoparticle probe and the sample under conditions effective to specifically bind the hemagglutinin of the target influenza virus to the recognition groups, wherein said specific binding generates a detectable plasmonic signal; and
   (c) detecting the signal generated in step (b).

26. The method of claim 25, wherein said specific binding in step (b) causes aggregation of the nanoparticles, wherein said aggregation generates or contributes to the detectable plasmonic signal.

27. The method of claim 25, wherein the detectable signal is observable with the naked eye and is generated within 60, 50, 40, 30, 20, 10 or 5 mins.

28. The method of claim 25, wherein the sample is a human or animal sample.

29. The method of claim 28, wherein the human or animal sample comprises a sample selected from a swab or body fluid.

30. The method of claim 25, wherein the sample is an environmental sample.

31. The method of claim 25, wherein the nanoparticle probe is utilized in an aqueous suspension.

32. The method of claim 31, wherein the suspension comprises 0.1 to 7.0 nM of nanoparticle probe.

33. A kit comprising a nanoparticle probe of claim 1 with instructions for use for performing a method of specifically detecting a target influenza virus in a sample.

34. A method for preparing a nanoparticle probe, the method comprising the steps of:

(a) preparing a glycoconjugate ligand compound as defined in claim 13 by:
       (i) creating a sialic-acid containing recognition group (Y) for binding HA by attaching one or more monosaccharide units to a sialic acid;
       (ii) attaching three or more sialic-acid containing recognition groups (Y) to a core moiety (X) comprising a linking moiety (L);
   (b) attaching the glycoconjugate ligand compound to a nanoparticle, via a linker moiety (L).

* * * * *

UNITED STATES PATENT AND TRADEMARK OFFICE
CERTIFICATE OF CORRECTION

PATENT NO. : 10,174,069 B2
APPLICATION NO. : 14/906436
DATED : January 8, 2019
INVENTOR(S) : Field et al.

Page 1 of 1

It is certified that error appears in the above-identified patent and that said Letters Patent is hereby corrected as shown below:

On the Title Page

Item (72), Lines 4-5, the spelling of Inventor Altaba's name should be corrected as follows:
María José MARÍN ALTABA Signed and Sealed this
Thirteenth Day of August, 2019

Andrei Iancu
*Director of the United States Patent and Trademark Office*